(12) United States Patent
Tomita et al.

(10) Patent No.: US 12,722,024 B2
(45) Date of Patent: Sep. 1, 2026

(54) MONITORING APPARATUS FOR ROTATING GANTRY, MONITORING METHOD FOR ROTATING GANTRY, AND PARTICLE BEAM TREATMENT SYSTEM

(71) Applicants: TOSHIBA ENERGY SYSTEMS & SOLUTIONS CORPORATION, Kawasaki (JP); TOSHIBA PLANT SYSTEMS & SERVICES CORPORATION, Kawasaki (JP)

(72) Inventors: Kazuhito Tomita, Yokohama Kanagawa (JP); Yasuhiro Yuguchi, Yokohama Kanagawa (JP); Shinichi Takama, Yokohama Kanagawa (JP); Masato Misawa, Yokohama Kanagawa (JP); Kiyohiko Kitagawa, Yokohama Kanagawa (JP); Yoshishige Nobuoka, Sagamihara Kanagawa (JP); Michitaka Ishiwata, Yokohama Kanagawa (JP)

(73) Assignees: TOSHIBA ENERGY SYSTEMS & SOLUTIONS CORPORATION, Kawasaki (JP); TOSHIBA PLANT SYSTEMS & SERVICES CORPORATION, Kawasaki (JP)

( * ) Notice: Subject to any disclaimer, the term of this patent is extended or adjusted under 35 U.S.C. 154(b) by 274 days.

(21) Appl. No.: 18/419,720

(22) Filed: Jan. 23, 2024

(65) Prior Publication Data

US 2024/0157173 A1 May 16, 2024

Related U.S. Application Data

(63) Continuation of application No. PCT/JP2022/030843, filed on Aug. 15, 2022.

(30) Foreign Application Priority Data

Oct. 5, 2021 (JP) ................................ 2021-163943
Oct. 5, 2021 (JP) ................................ 2021-163944
(Continued)

(51) Int. Cl.
*A61N 5/10* (2006.01)
*A61N 5/00* (2006.01)

(52) U.S. Cl.
CPC ......... *A61N 5/1048* (2013.01); *A61N 5/1081* (2013.01); *A61N 2005/005* (2013.01);
(Continued)

(58) Field of Classification Search
None
See application file for complete search history.

(56) References Cited

U.S. PATENT DOCUMENTS 6,789,762 B1 * 9/2004 Schneider .......... B65H 54/2875 242/478.2
2006/0153330 A1 7/2006 Wong et al.
(Continued)

FOREIGN PATENT DOCUMENTS

JP H10-330037 A 12/1998
JP 2001-251748 A 9/2001
(Continued)

OTHER PUBLICATIONS

JP Notice of Reasons for Refusal JP Appl. Ser. No. 2021-163943 dated Aug. 5, 2025 (10 pages).
(Continued)

*Primary Examiner* — Marcus H Taningco
(74) *Attorney, Agent, or Firm* — Foley & Lardner LLP

(57) ABSTRACT

According to one embodiment, a monitoring apparatus for a rotating gantry comprising: a rotating gantry that supports
(Continued)

both an irradiation nozzle configured to radiate a particle beam and a transport unit configured to transport the particle beam to the irradiation nozzle and rotates around a horizontal axis directed in a horizontal direction; a plurality of cables, each of which is connected at one end to the rotating gantry and is connected at another end to a stationary device; a spool that is provided on the rotating gantry and performs winding or unwinding of the plurality of cables; and a monitoring unit that monitors a state of the plurality of cables in the spool.

11 Claims, 40 Drawing Sheets

(30) Foreign Application Priority Data

Oct. 5, 2021 (JP) ................................. 2021-163945
Oct. 5, 2021 (JP) ................................. 2021-163946

(52) U.S. Cl.
CPC ................. *A61N 2005/1074* (2013.01); *A61N 2005/1092* (2013.01)

(56) References Cited

U.S. PATENT DOCUMENTS

2012/0280150 A1* 11/2012 Jongen .................... G21K 5/04 250/492.3
2015/0224341 A1* 8/2015 Vahala .................. A61B 5/055 600/411
2019/0090830 A1* 3/2019 Gao ...................... A61B 6/035

FOREIGN PATENT DOCUMENTS

| | | | |
|---|---|---|---|
| JP | 2002-350112 | A | 12/2002 |
| JP | 2008-067908 | A | 3/2008 |
| JP | 2011-112435 | A | 6/2011 |
| JP | 2014-147451 | A | 8/2014 |
| JP | 2014-158971 | A | 9/2014 |
| JP | 2017-127434 | A | 7/2017 |
| KR | 10-2009-0117496 | | 11/2009 |

OTHER PUBLICATIONS

International Search Report with English Translation of International Patent Application No. PCT/JP2022/030843 dated Sep. 20, 2022 (8 pages).

* cited by examiner 22
23
26
27
28
29
Y
Z
X 22
26
56
27
23
X
Y
Z

MONITORING APPARATUS FOR ROTATING GANTRY, MONITORING METHOD FOR ROTATING GANTRY, AND PARTICLE BEAM TREATMENT SYSTEM

CROSS-REFERENCE TO RELATED APPLICATIONS

This application is a Continuation Application of No. PCT/JP2022/030843, filed on Aug. 15, 2022, and the PCT application is based upon and claims the benefit of priority from Japanese Patent Applications No. 2021-163943, No. 2021-163944, No. 2021-163945 and No. 2021-163946, filed on Oct. 5, 2021, the entire contents of which are incorporated herein by reference.

TECHNICAL FIELD

Embodiments of the present invention relate to a technique for monitoring a rotating gantry.

BACKGROUND

When a treatment table of a rotating gantry is used in a particle beam treatment system, particle beams can be radiated in a state where a patient remains stationary, and thus, the burden on the patient can be reduced as compared with a case of using a fixed treatment table. However, the rotating gantry includes many devices inside, and these devices rotate together with the rotating gantry. Hence, the rotating gantry needs to be connected to stationary external devices by using many cables that are necessary for electric power, control, and communication. In the rotating gantry, cables are wound or unwound onto/from a spool each time the rotating gantry rotates.

However, when a large number of cables are provided, the cables are irregularly wound in some cases. If the cables are irregularly wound, external force is applied to the cables, which may cause damage or breakage of the cables and resultantly lead to interruption of treatment or damage to the devices.

PRIOR ART DOCUMENT

Patent Document

[Patent Document 1] JP 2014-147451 A
[Patent Document 2] JP H10-330037 A
[Patent Document 3] JP 2014-158971 A
[Patent Document 4] JP 2001-251748 A
[Patent Document 5] JP 2008-067908 A

Problem to be Solved by Invention

An object of the present invention is to provide a rotating-gantry monitoring technique by which a winding state of cables can be monitored.

DETAILED DESCRIPTION

In one embodiment of the present invention, a monitoring apparatus for a rotating gantry comprising: a rotating gantry that supports both an irradiation nozzle configured to radiate a particle beam and a transport unit configured to transport the particle beam to the irradiation nozzle and rotates around a horizontal axis directed in a horizontal direction; a plurality of cables, each of which is connected at one end to the rotating gantry and is connected at another end to a stationary device; a spool that is provided on the rotating gantry and performs winding or unwinding of the plurality of cables; and a monitoring unit that monitors a state of the plurality of cables in the spool.

According to embodiments of the present invention, it is possible to provide a rotating-gantry monitoring technique by which a winding state of cables can be monitored.

First Embodiment

Hereinbelow, a description will be given of embodiments of a particle beam treatment system and a rotating gantry in detail by referring to the accompanying drawings. First, the first embodiment will be described by using FIG. 1 to FIG. 11. In the following description, the left side of the sheet of each of FIG. 2, FIG. 3, FIG. 6, FIG. 7, and FIG. 8 is assumed to be the front side of the rotating gantry, and the right side of the sheet of each of these figures is assumed to be the back side (i.e., the rear side) of the rotating gantry. In each figure, the axial direction of the rotating gantry is assumed to be the Z-axis direction in the orthogonal coordinate system, the vertical direction (i.e., the up-and-down direction) orthogonal to this Z-axis direction is assumed to be the Y-axis direction, and the horizontal direction orthogonal to both the Z-axis and the Y-axis is assumed to be the X-axis direction. Note that the X-axis direction and the Y-axis direction are sometimes referred to as the radial direction of the rotating gantry. Furthermore, the direction of rotating around the axis along the outer circumferential surface of the rotating gantry is sometimes referred to as the circumferential direction.

Figure 1:
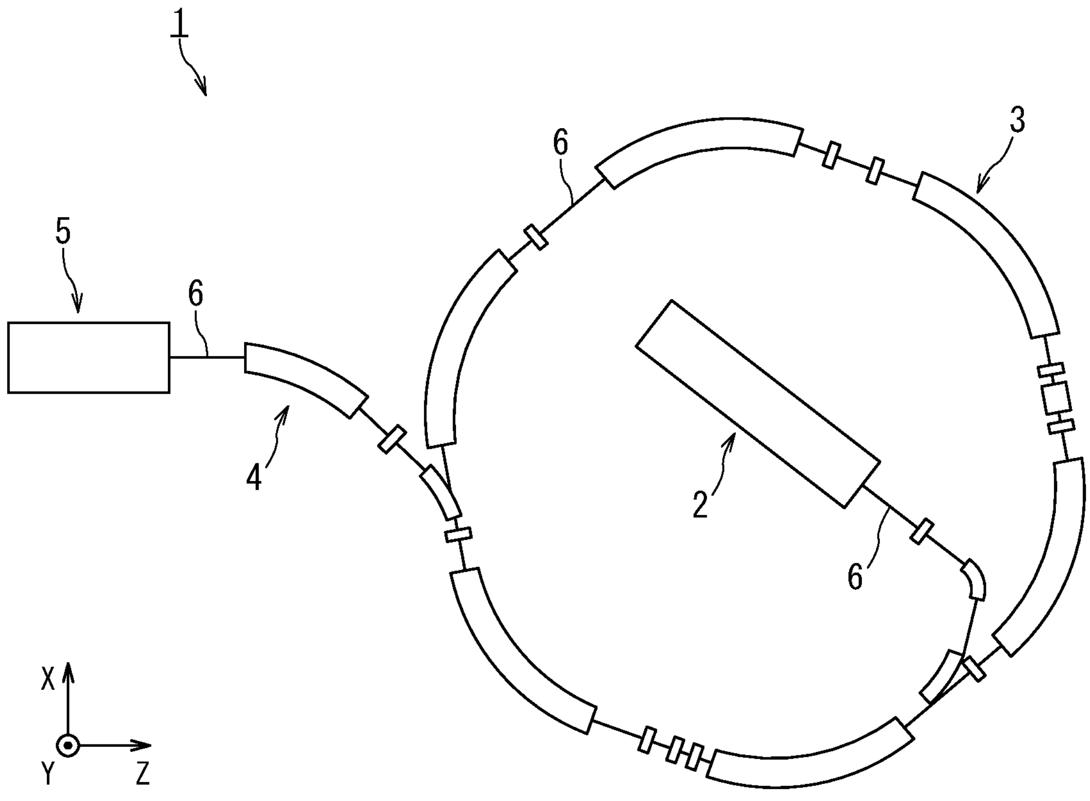
FIG. 1 is a plan view illustrating an overall configuration of a particle beam treatment system according to the first embodiment.

The reference sign 1 in FIG. 1 denotes the particle beam treatment system according to the first embodiment. In this particle beam treatment system 1, treatment is performed by irradiating a diseased tissue (cancer) of a patient as a target with particle beams such as carbon ions.

A radiation therapy technique with the use of the particle beam treatment system 1 is also referred to as a heavy ion beam cancer treatment technique. This technique is said to be able to damage a cancerous lesion (i.e., focus of disease) and minimize the damage to normal cells by pinpointing the cancerous lesion with carbon ions. Note that the particle beams are defined as radioactive rays heavier than electrons, and include proton beams and heavy ion beams, for example. Of these particle beams, heavy ion beams are defined as radioactive rays heavier than helium atoms.

As compared with the conventional cancer treatment using X-rays, gamma rays, or proton beams, the cancer treatment using heavy ion beams has characteristics that: (i) the ability to kill the cancerous lesion is higher; and (ii) the radiation dose is weak on the surface of the body of the patient so as to peak at the cancerous lesion. Thus, the number of irradiations and side effects can be reduced, and the treatment period can be shortened.

As shown in FIG. 1, the particle beam treatment system 1 includes a beam generator 2, a circular accelerator 3, a beam transport line 4, and a rotating gantry 5.

Figure 2:
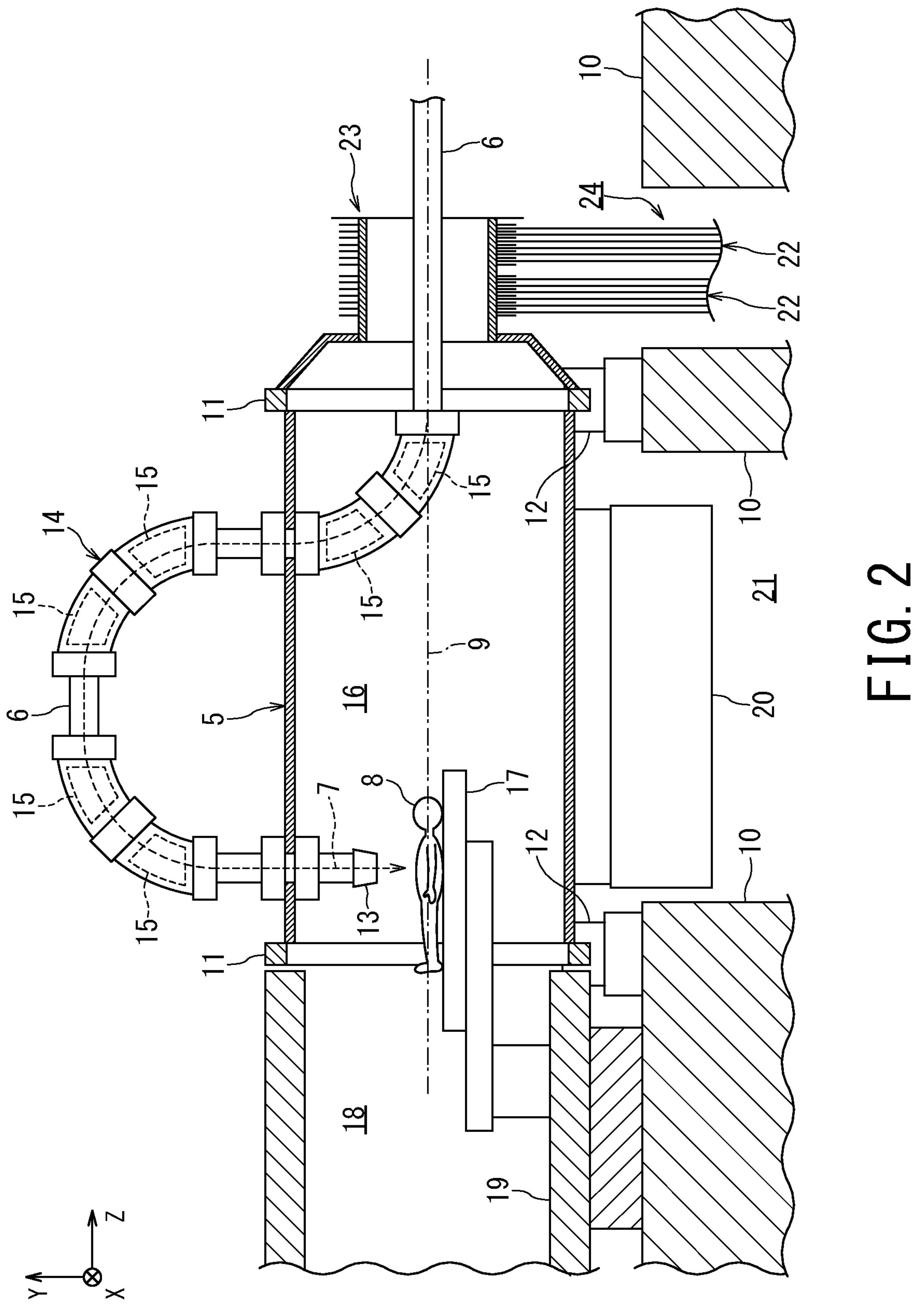
FIG. 2 is a side view illustrating a rotating gantry according to the first embodiment.

The beam generator 2 has an ion source of carbon ions, which are charged particles, and uses these carbon ions to generate a particle beam 7 (FIG. 2). The circular accelerator 3 has a ring shape in a plan view, and accelerates the particle beam 7 generated by the beam generator 2. The beam transport line 4 transports the particle beam 7 accelerated by the circular accelerator 3 to the rotating gantry 5. A patient 8 (FIG. 2) to be irradiated with the particle beam 7 is placed in the rotating gantry 5.

In this particle beam treatment system 1, first, the particle beam 7 of carbon ions generated by the beam generator 2 is inputted from the beam generator 2 to the circular accelerator 3. This particle beam 7 is accelerated to approximately 70% of the speed of light while orbiting the circular accelerator 3 approximately one million times. Thereafter, this particle beam 7 is guided to the rotating gantry 5 via the beam transport line 4.

The beam generator 2, the circular accelerator 3, and the beam transport line 4 are provided with vacuum ducts 6 (beam pipes), inside of which is vacuumized. The particle beam 7 passes the inside of the vacuum ducts 6. The vacuum ducts 6 of the beam generator 2, the circular accelerator 3, and the beam transport line 4 are integrated so as to form a transport path that guides the particle beam 7 to the rotating gantry 5. In other words, the vacuum ducts 6 are closed continuous space with a sufficient degree of vacuum to allow the particle beam 7 to pass through.

As shown in the cross-sectional view of FIG. 2, the rotating gantry 5 is an apparatus in a cylindrical shape. This rotating gantry 5 is installed in such a manner that the axis 9 of its cylindrical body is directed in the horizontal direction. The rotating gantry 5 can rotate around this horizontal axis 9.

The rotating gantry 5 is supported by a structure 10 of a building constituting a treatment facility in which the particle beam treatment system 1 is installed. For example, end rings 11 are fixed to the front portion and the rear portion of the main body of the rotating gantry 5. Below these end rings 11, rotary drivers 12 are provided. The rotary drivers 12 rotatably support the end rings 11 and include drive motors. These rotary drivers 12 are supported by the structure 10. The driving force of the rotary drivers 12 is applied to the rotating gantry 5 through the end rings 11, and thereby, the rotating gantry 5 is rotated around the horizontal axis 9.

The rotating gantry 5 is provided with the vacuum ducts 6 extending from the beam transport line 4 (FIG. 1). The vacuum ducts 6 are first guided from the rear side of the rotating gantry 5 into the inside along the horizontal axis 9. Further, the vacuum ducts 6 once extend outward from the outer circumferential surface of the rotating gantry 5, and then again extend toward the inside of the rotating gantry 5. The tip of the vacuum ducts 6 extends to a position close to the patient 8.

Of the vacuum ducts 6, the portion along the horizontal axis 9 of the rotating gantry 5 is provided with a predetermined rotation mechanism, which is not particularly illustrated. Of the vacuum ducts 6, the portion outside this rotating mechanism is stationary, and the portion inside this rotating mechanism rotates together with the rotation of the rotating gantry 5.

In addition, the rotating gantry 5 includes: an irradiation nozzle 13 configured to irradiate the patient 8 with the particle beam 7; and a transport unit 14 (or transport apparatus 14) configured to transport the particle beam 7 to the irradiation nozzle 13. In other words, the irradiation nozzle 13 and the transport unit 14 are supported by the rotating gantry 5.

Further, the transport unit 14 includes superconducting electromagnets 15 configured to generate a magnetic field that forms a path for transporting the particle beam 7. These superconducting electromagnets 15 are bending electromagnets configured to change the traveling direction of the particle beam 7 along the vacuum ducts 6 or quadrupole electromagnets configured to control convergence and divergence of the particle beam 7, for example.

The irradiation nozzle 13 is provided at the tip of the vacuum ducts 6 and radiates the particle beam 7 guided by the transport unit 14 toward the patient 8. The irradiation nozzle 13 is fixed to the inner circumferential surface of the rotating gantry 5. Note that the particle beam 7 is radiated from the irradiation nozzle 13 in the direction perpendicular to the horizontal axis 9.

Inside the rotating gantry 5, a treatment space 16 for performing particle beam therapy is provided. The patient 8 is placed on a treatment table 17 provided in this treatment space 16. This treatment table 17 can be moved with the patient 8 placed thereon. Positioning can be performed by moving this treatment table 17 in such a manner that the patient 8 on this treatment table 17 is moved to the irradiation position of the particle beam 7. Thus, the particle beam 7 can be radiated to an appropriate site such as the diseased tissue of the patient 8.

The patient 8 is placed at the position of the horizontal axis 9, and the irradiation nozzle 13 can be rotated around the stationary patient 8 by rotating the rotating gantry 5. For example, the irradiation nozzle 13 can be rotated around the patient 8 (i.e., around the horizontal axis 9) clockwise or counterclockwise in increments of 180° when viewed from the back. The particle beam 7 can be radiated from any direction around the patient 8. In other words, the rotating gantry 5 is an apparatus that can change the irradiation direction of the particle beam 7 guided by the beam transport line 4 with respect to the patient 8. Thus, the particle beam 7 can be radiated from the appropriate direction to the lesion site with higher precision while reducing the burden on the patient 8.

The particle beam 7 loses its kinetic energy at the time of passing through the body of the patient 8 so as to decrease its velocity and receive a resistance that is approximately inversely proportional to the square of the velocity, and stops rapidly when it decreases to a certain velocity. The stopping point of the particle beam 7 is referred to as the Bragg peak at which high energy is emitted. The particle beam treatment system 1 matches this Bragg peak with the position of the lesion tissue (i.e., affected part) of the patient 8, and thus, can kill only the lesion tissue while suppressing the damage to normal tissues.

The treatment space 16 provided inside the rotating gantry 5 is formed so as to be integrated with a treatment room 18 that is located on the front side of the rotating gantry 5. Note that the treatment table 17 is fixed to a floor 19 of the stationary treatment room 18. In other words, it is configured in such a manner that the position of the treatment table 17 does not change regardless of the rotation of the rotating gantry 5 and the irradiation nozzle 13.

Of the outer circumferential surface of the rotating gantry 5, on the opposite side of the portion where the transport unit 14 is provided, a counterweight 20 is fixed. This counterweight 20 is provided in order to maintain balance with the transport unit 14 around the rotating gantry 5. In other words, the weight of the counterweight 20 is set so as to correspond to the weight of the transport unit 14. In addition, a weight pit 21 formed in a concave shape in the structure 10 is provided below the rotating gantry 5 in such a manner that the counterweight 20 can pass through the weight pit 21 along with the rotation of the rotating gantry 5.

Further, a plurality of cables 22 are led from the outside to the rotating gantry 5. These cables 22 include power supply cables, signal lines, and flexible coolant hoses, for example. These cables 22 are provided in order to supply electric power and transmit control signals to specific devices installed in the rotating gantry 5. These cables 22 include flexible hoses that supply a coolant to the superconducting electromagnets 15 included in the transport unit 14.

At the rear of the rotating gantry 5, a spool 23 is provided. The spool 23 winds or unwinds the cables 22 along with the rotation of the rotating gantry 5. The axis of the spool 23 coincides with the horizontal axis 9 of the rotating gantry 5.

Below the spool 23, a cable pit 24 formed in a concave shape in the structure 10 is provided. In the cable pit 24, the cables 22 hanging down from the spool 23 can be disposed. The width dimension of the cable pit 24 in the X-axis direction is set to be larger than the diameter of the spool 23.

Figure 3:
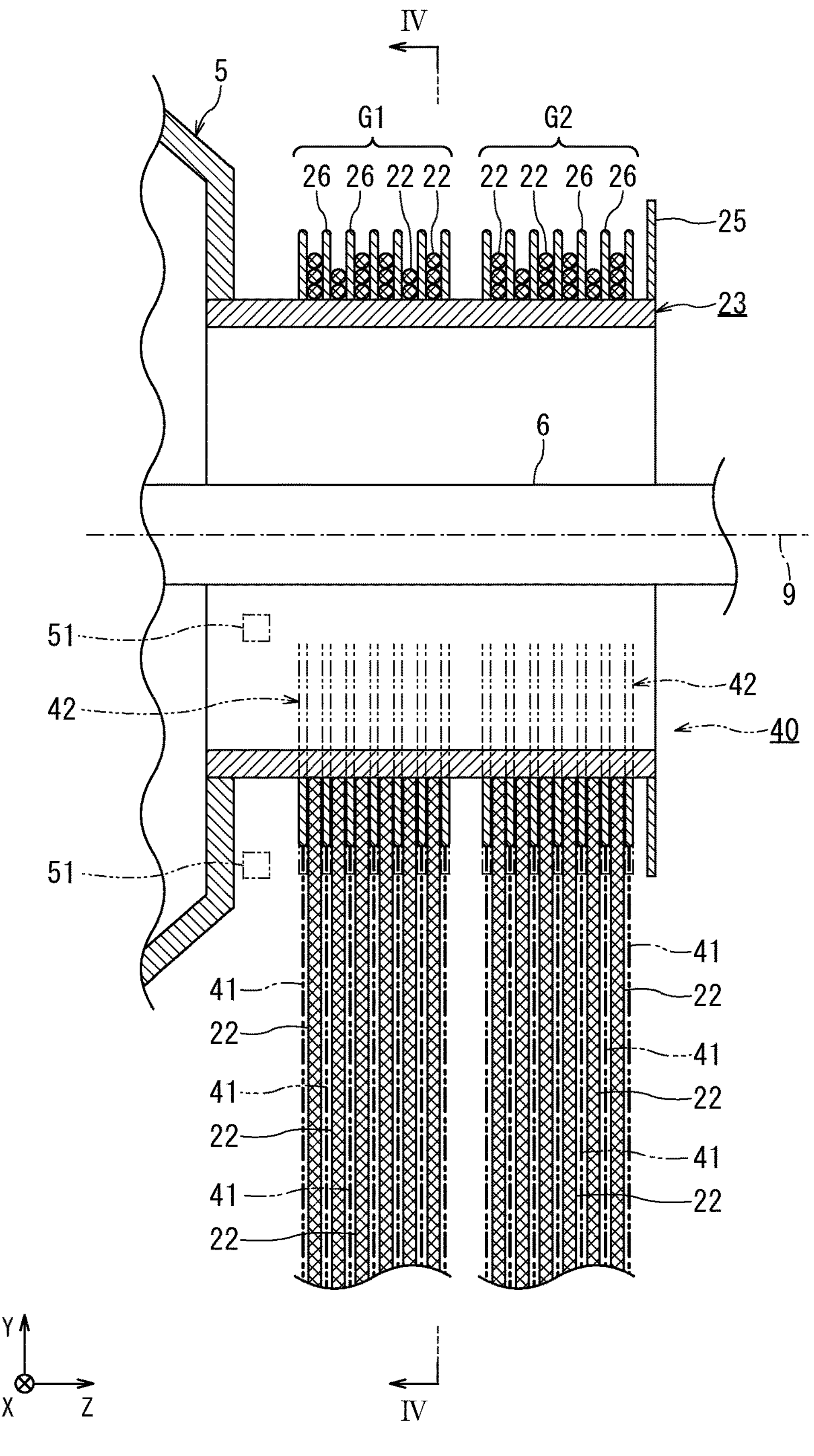
FIG. 3 is a side view illustrating a spool of the rotating gantry according to the first embodiment.

As shown in the cross-sectional view of FIG. 3, the spool 23 is provided so as to protrude rearward from the rear portion of the rotating gantry 5. This spool 23 is a cylindrical portion, and is formed to have a smaller diameter than the diameter of the main body of the rotating gantry 5. This spool 23 includes one disk-shaped flange 25, a plurality of disk-shaped brim disks 26, and a plurality of concave lanes 27 (FIG. 7) that hold the cables 22.

The flange 25 is provided at the rear end of the spool 23. The plurality of brim disks 26 are arranged side by side in the axial direction (i.e., in the Z-axis direction) between the flange 25 and the rotating gantry 5. These brim disks 26 are formed to have a smaller diameter than the diameter of the flange 25. In addition, the rear brim disks 26, which are closest to the flange 25, are located at a distance from the flange 25. The plurality of lanes 27 (FIG. 7) are formed between the respective brim disks 26.

Figure 7:
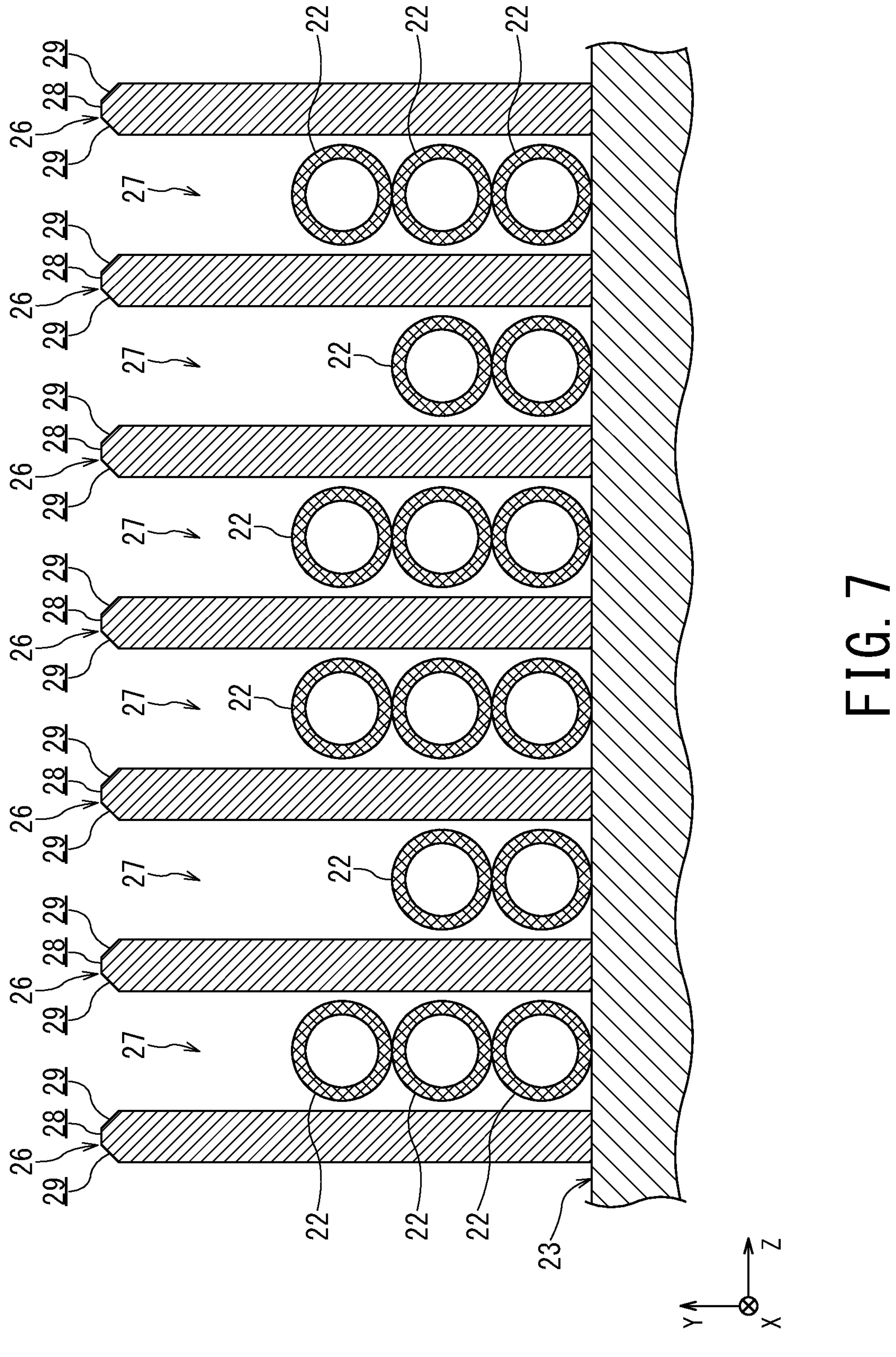
FIG. 7 is a side view illustrating brim disks according to the first embodiment.

As shown in the cross-sectional view of FIG. 7, each lane 27 accommodates a plurality of cables 22. For example, one lane 27 accommodates two or three cables 22. Note that the number of cables 22 to be accommodated per one lane 27 may be four or more.

Figure 6:
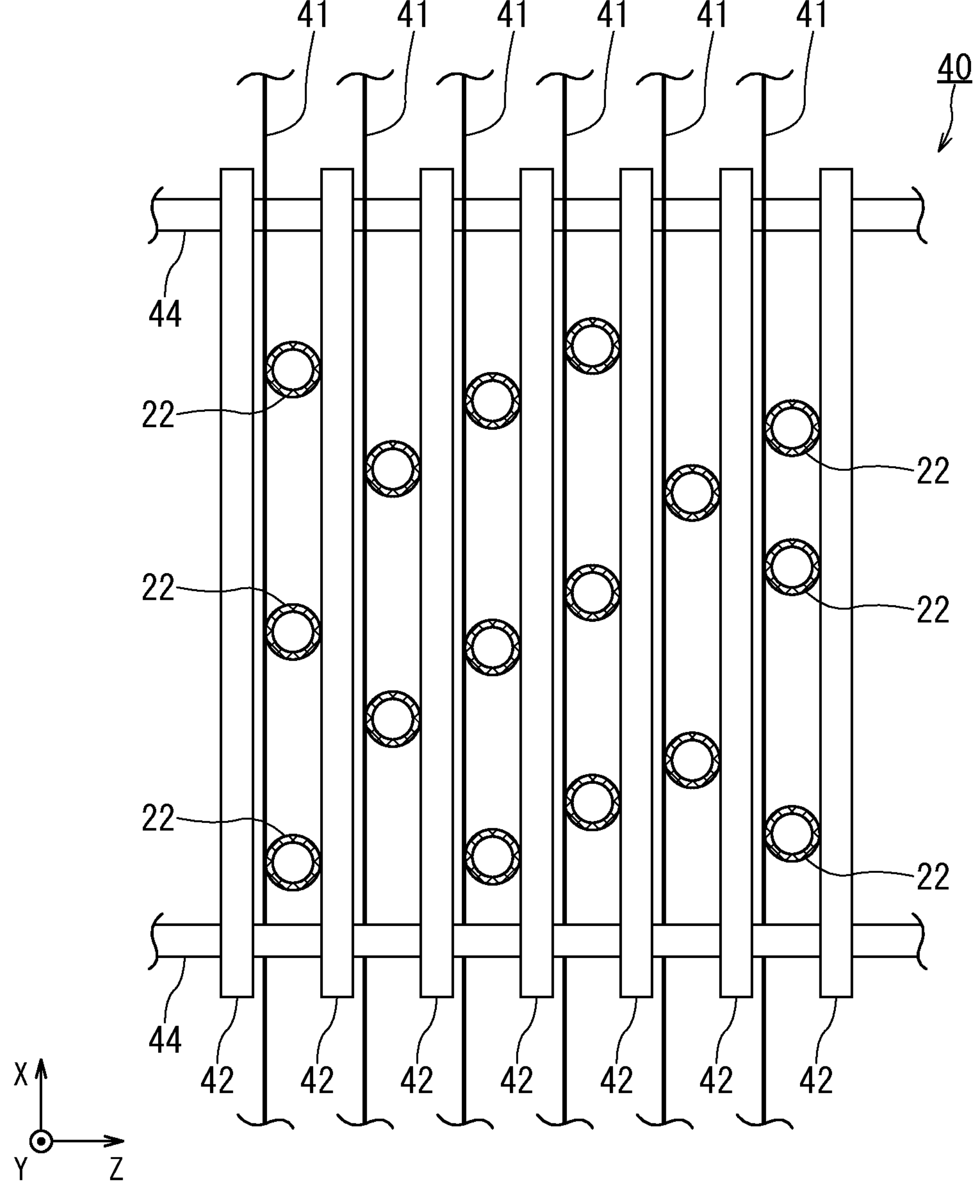
FIG. 6 is a plan view illustrating straightening wires and the straightening plates according to the first embodiment.

When the cables 22 are wound in the circumferential direction of the spool 23, the plurality of cables 22 are arranged in line in the axial direction (i.e., in the Z-axis direction) of the spool 23 and in line in the radial direction (i.e., in the X-axis direction and the Y-axis direction) of the spool 23 in accordance with the arrangement of the brim disks 26 and the lanes 27. In addition (as shown in FIG. 6), when the plurality of cables 22 hang down from the spool 23, the cables 22 are arranged in line in the axial direction (i.e., in the Z-axis direction) of the spool 23 and in line in the horizontal direction (i.e., in the X-axis direction).

Note that the width of each lane 27 may be different depending on the number of the cables 22 to be accommodated or thickness of each cable 22. In addition, a plurality of cables 22 of different types or different thicknesses may be accommodated in one lane 27.

On the circumferential surface 28 of each brim disk 26, both corners are cut out to form chamfered portions 29 (i.e., bevels 29). In other words, the chamfered portions 29 are formed around the periphery of the brim disks 26. In this configuration, when the cables 22 are accommodated in the lanes 27, the cables 22 are less likely to be caught on the brim disks 26, thereby, the friction or tension on the cables 22 being caught on the brim disks 26 can be reduced, and consequently, the cables 22 are prevented from being irregularly wound.

For example, the chamfered portions 29 are inclined surfaces that are inclined at approximately 45° with respect to the protruding direction of the brim disks 26. Since these chamfered portions 29 are provided, the inlet width of each lane 27 is widened so as to allow the cables 22 to be smoothly accommodated in the lanes 27.

Even when the chamfered portions 29 are provided, part of the circumferential surface 28 of each brim disk 26 remains. For example, the circumferential surface 28 of the tip of each brim disk 26 remains. This structure can prevent the cables 22 from being cut or being worn out even if the cables 22 are get caught on the brim disk 26.

Figure 4:
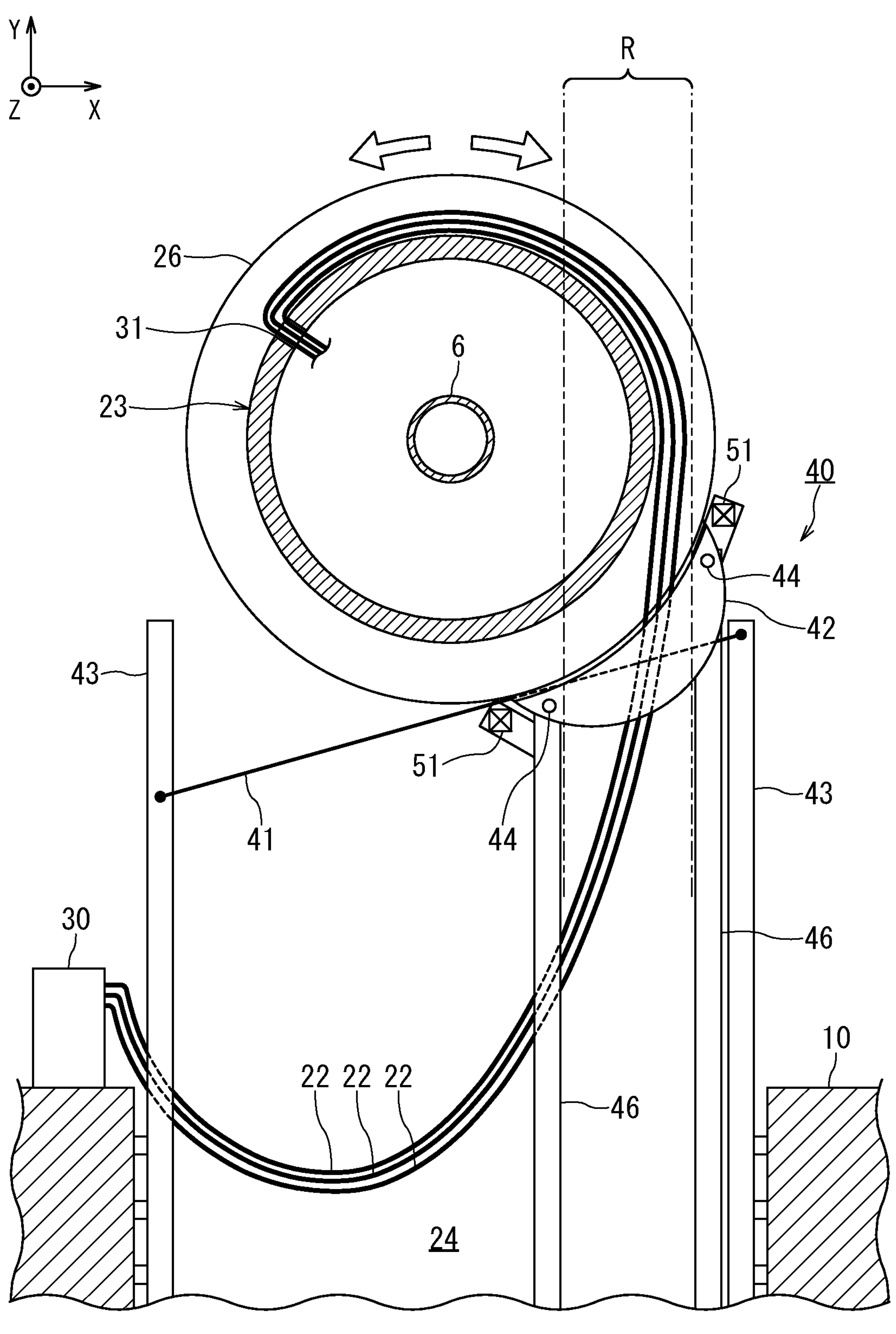
FIG. 4 is a rear view of the rotating gantry corresponding to the cross-section taken along the line IV-IV of FIG. 3.

As shown in FIG. 4, each cable 22 is connected at one end to the spool 23 of the rotating gantry 5, and is connected at the opposite end to a stationary fixing device 30. The fixing device 30 is fixed to the structure 10, for example. The plurality of cables 22 are composed of power lines for supplying electric power, signal lines for transmitting control signals, and flexible hoses for supplying the coolant, for example. The fixing device 30 is composed of a power supply, a terminal block, and a coolant supply pump, for example. Although FIG. 4 is a rear view of the rotating gantry 5, for the sake of facilitating understanding, respective illustrations of the main body of the rotating gantry 5, the rotary drivers 12, and the transport unit 14 are omitted in FIG. 4.

One end of each cable 22 is introduced into the rotating gantry 5 through a penetration portion 31 formed in the spool 23. The cables 22 are connected to the devices such as the superconducting electromagnets 15 (FIG. 2) installed in the rotating gantry 5. Note that one end of each cable 22 is fixed to the penetration portion 31. Each cable 22 is wound in the circumferential direction from the fixed penetration portion 31 along the outer periphery of the spool 23.

In the first embodiment, a description will be given of the case where the cables 22 are flexible hoses. Each flexible hose is hollow inside (FIG. 7) and is provided in order to supply the coolant such as liquid helium and liquid nitrogen to the superconducting electromagnets 15 (FIG. 2). Each flexible hose is configured as a pressure-resistant hose in which metal wires are woven to increase its pressure resistance, and can supply the coolant at a predetermined pressure.

As shown in FIG. 3 and FIG. 4, the plurality of cables 22 are divided or classified into a first group G1 and a second group G2. This division or classification of the cables 22 into the first group G1 and the second group G2 may be performed depending on the type of the cables 22 or depending on the connection destinations of the cables 22. Both the plurality of brim disks 26 for winding the plurality of cables 22 of the first group G1 and the other plurality of brim disks for winding the plurality of cables 22 of the second group G2 are provided so as to match the above-described division.

The cables 22 of the first group G1 are different in winding direction around the spool 23 from the cables 22 of the second group G2. For example, when the rotating gantry 5 rotates counterclockwise in a rear view, the cables 22 of the first group G1 are wound onto the spool 23, whereas the cables 22 of the second group G2 are unwound from the spool 23. Conversely, when the rotating gantry 5 rotates clockwise, the cables 22 of the first group G1 are unwound from the spool 23, whereas the cables 22 of the second group G2 are wound onto the spool 23.

In FIG. 4, for the sake of facilitating understanding, only the cables 22 of the first group G1 are illustrated and the cables 22 of the second group G2 are omitted. In the actual rear view, the cables 22 of the first group G1 and the cables 22 of the second group G2 hanging down from the spool 23 appear to intersect each other at the cable pit 24.

The particle beam treatment system 1 according to the first embodiment is provided with a cable straightening apparatus 40 (or cable disentangling apparatus 40) for the rotating gantry 5. In the following, though the verb "straighten" is mainly used to mean disentangling or untwisting a plurality of cables or making the winding state of the cables more regular in order to prevent these cables from crossing or entangling each other. The cable straightening apparatus 40 includes a plurality of straightening wires 41 and a plurality of straightening plates 42. The cables 22 pass between the straightening wires 41 and between the straightening plates 42. This cable straightening apparatus 40 is provided in order to straighten the plurality of cables 22, prevent the cables 22 from being irregularly wound, and suppress wear of the cables 22.

The straightening wires 41 and the straightening plates 42 can be classified into those for straightening the cables 22 of the first group G1 and the rest for straightening the cables 22 of the second group G2. In order to avoid complicated illustration in terms of promoting understanding, FIG. 4 illustrates only the straightening wires 41 and the straightening plates 42 for the first group G1, and illustration of the straightening wires 41 and the straightening plates 42 for the second group G2 is omitted in FIG. 4. The straightening wires 41 and straightening plates 42 of the first group G1 have the same configuration as the straightening wires 41 and straightening plates 42 of the second group G2, and both are arranged to be bilaterally symmetrical with respect to the rotating gantry 5. For example, when viewed from the rear, the straightening wires 41 of the first group G1 and the straightening wires 41 of the second group G2 appear to be strung so as to intersect each other in an X-shape.

The plurality of straightening wires 41 are laid or bridged laterally below the spool 23 and are provided in a stationary state. These straightening wires 41 are provided in order to partition or separate the plurality of cables 22 hanging down from the spool 23. This structure can prevent the cables 22 from being irregularly wound or being entangled with each other, and thus, can suppress wear of the cables 22. For example, the straightening wires 41 bend, and thus, wear of the cables 22 can be suppressed.

Each of the straightening wires 41 is provided at a position corresponding to each of the brim disks 26 and arranged in the direction in which the brim disks 26 are arranged. In this manner, the plurality of cables 22 arranged in the axial direction can be partitioned.

For example, the plurality of straightening wires 41 are strung in parallel with each other as shown in FIG. 6. The cables 22 are arranged between the respective straightening wires 41. The arrangement of the respective straightening wires 41 is set so as to match the arrangement of the brim disks 26. In other words, each bundle of the cables 22 disposed between the straightening wires 41 corresponds to the bundle of the cables 22 to be accommodated in one lane 27. At the time of winding or unwinding the cables 22, the cables 22 are partitioned along the straightening wires 41. In this configuration, contact between the cables 22 is suppressed, the friction or tension on the cables 22 to be caused by the contact is reduced, thereby, swinging of the cables 22 is suppressed, and consequently, the cables 22 are prevented from being irregularly wound.

As shown in FIG. 4, wire mounts 43 extending upward from the bottom surface of the cable pit 24 are fixed to the structure 10 in which the cable pit 24 is formed. For example, a pair of left and right wire mounts 43 spaced apart in the X-axis direction are provided for one straightening wire 41. One end and the other end of each straightening wire 41 are fixed to these wire mounts 43.

The straightening wires 41 are strung in the state of being inclined with respect to the horizontal direction. In this manner, the straightening wires 41 are brought into oblique contact with the cables 22 hanging down in the vertical direction, which can reduce the resistance when the straightening wires 41 rub against the cables 22. As a result, wear of the cables 22 can be reduced and the cables 22 can be prevented from being irregularly wound.

Under the assumption that the spool 23 is divided into a semicircle on the side where the cables 22 hang down and the opposite semicircle, the straightening wires 41 are inclined in such a manner that the side where the cables 22 hang down is higher and the opposite side is lower. In this configuration, the angle at which the cables 22 contact the straightening wires 41 is made smaller, thereby the cables 22 are brought into gentle contact with the straightening wires 41, and consequently, the resistance when the straightening wires 41 rub against the cables 22 can be reduced.

Furthermore, each straightening wire 41 is provided at a position adjacent to the brim disk 26 and extends in a tangential direction of the periphery of the brim disk 26. In this configuration, the straightening wires 41 can guide the cables 22 at the portion where the cables 22 are no longer held by the brim disks 26. Hence, the cables 22 are not subjected to more friction or more tension than expected, and thus, the cables 22 are prevented from being irregularly wound.

The plurality of straightening plates 42 are provided in parallel in a stationary state at a position close to the spool 23. These straightening plates 42 are provided below the spool 23 in order to partition the plurality of cables 22 arranged in the axial direction (i.e., in the Z-axis direction). In this configuration, the straightening plates 42 individually partition the cables 22 in the axial direction, and consequently, the cables 22 are prevented from being irregularly wound.

Each straightening plate 42 is provided at a position corresponding to each brim disk 26, and is arranged in the direction in which the brim disks 26 are arranged. In this manner, the plurality of cables 22 arranged in the axial direction can be partitioned.

For example, as shown in FIG. 6, the plurality of straightening plates 42 are arranged in parallel with each other. The cables 22 are arranged between the respective straightening plates 42. The arrangement of the respective straightening plates 42 is set so as to match the arrangement of the brim disks 26. In other words, each bundle of the cables 22 to be disposed between the straightening plates 42 corresponds to the bundle of cables 22 to be accommodated in one lane 27. At the time of winding or unwinding the cables 22, the cables 22 are partitioned by the straightening plates. 42. Hence, unintentional contact between the cables 22 is suppressed, and thus, the cables 22 are prevented from being irregularly wound.

In the first embodiment as shown in FIG. 4, a specific range R in which the cables 22 hang down from the spool 23 is set in advance. For example, the cables 22 hang down from the end of the spool 23 in the X-axis direction, and a predetermined range including this hanging portion is set as the specific range R. This specific range R is the range in which the cables 22 hang down almost in the gravitational direction due to their own weight. The plurality of straightening plates 42 are disposed in this specific range R.

Figure 5:
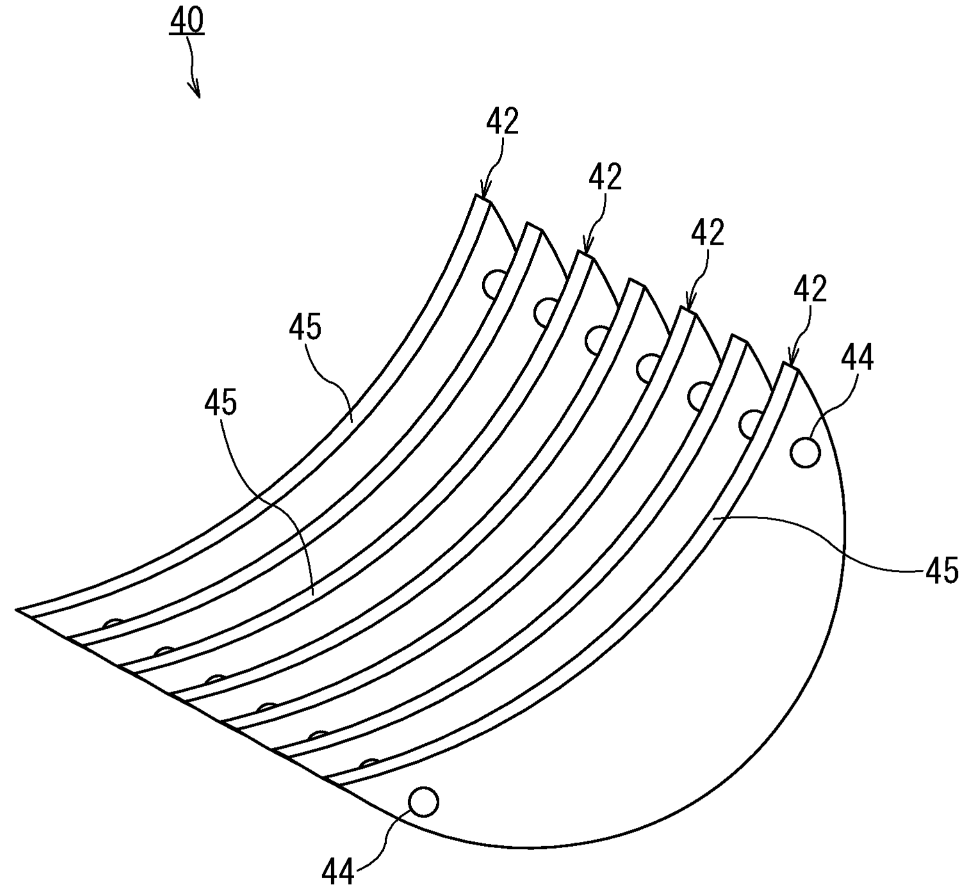
FIG. 5 is a perspective view illustrating straightening plates according to the first embodiment.

As shown in FIG. 5 and FIG. 6, each straightening plate 42 is a plate-shaped member that forms a crescent moon shape when viewed from the rear. The respective straightening plates 42 are connected to each other by connecting members 44 in the state of being spaced apart from each other. The connecting members 44 are rod-shaped members extending in the axial direction (i.e., in the Z-axis direction), and connect the straightening plates 42 with each other at one end and at the other end of the specific range R (FIG. 4) in the axial direction (i.e., in the Z-axis direction), for example. In this configuration, the connecting members 44 restrict the movement range of the cables 22 in the horizontal direction (i.e., in the X-axis direction), thereby, the cables 22 hanging down from the spool 23 are accommodated in the specific range R, and consequently, the cables 22 are prevented from being irregularly wound even if the cables 22 swing between one end and the other end of the specific range R.

Each straightening plate 42 has a curved edge 45 that is curved along the circumferential edge of the brim disk 26. These curved edges 45 are positioned closer to the brim disks 26 than the straightening wires 41. In this manner, at the position where the cables 22 enter and exit the lane 27 (FIG. 7) between the brim disks 26, the cables 22 are guided by the rigid straightening plates 42. Hence, unintended contact between the cables 22 is suppressed and swinging of the cables 22 is suppressed, which can prevent the cables 22 from being irregularly wound.

As shown in FIG. 4, plate mounts 46 extending upward from the bottom surface of the cable pit 24 are fixed to the structure 10 in which the cable pit 24 is formed. For example, a plurality of plate mounts 46 spaced apart in the X-axis direction are provided. The straightening plates 42 are fixed to the connecting members 44.

In the first embodiment as shown in FIG. 6, the straightening wires 41 are provided overlap (i.e., additionally) in the specific range R (FIG. 4) where the straightening plates 42 are provided. In other words, in a plan view, the straightening plates 42 and the straightening wires 41 are arranged alternately in the axial direction (i.e., in the Z-axis direction). For example, one cable 22 is disposed between one straightening plate 42 and one straightening wire 41, and the plurality of cables 22 arranged in the axial direction are partitioned by the straightening plates 42 and the straightening wires 41.

Although the straightening wires 41 are provided duplicately in the range where the straightening plates 42 are provided in the first embodiment, the embodiments of the present invention may take another form. For example, the arrangement range of the straightening wires 41 and the arrangement range of the straightening plates 42 may be differentiated in the axial direction (i.e., in the Z-axis direction) from each other. Further, it may configured in such a manner that some of the cables 22 arranged in the axial direction are partitioned by the straightening plates 42 and the remaining cables 22 are partitioned by the straightening wires 41.

Although the straightening wires 41 are provided duplicately at the height position where the straightening plates 42 are provided in the first embodiment, the embodiments of the present invention may take another form. For example, the height positions (i.e., positions in the Y-axis direction) of the straightening plates 42 may be different from the height positions of the straightening wires 41. In particular, it may configured in such a manner that the straightening plates 42 are provided in the vicinity of the brim disks 26 and the straightening wires 41 are strung below the straightening plates 42.

Figure 9:
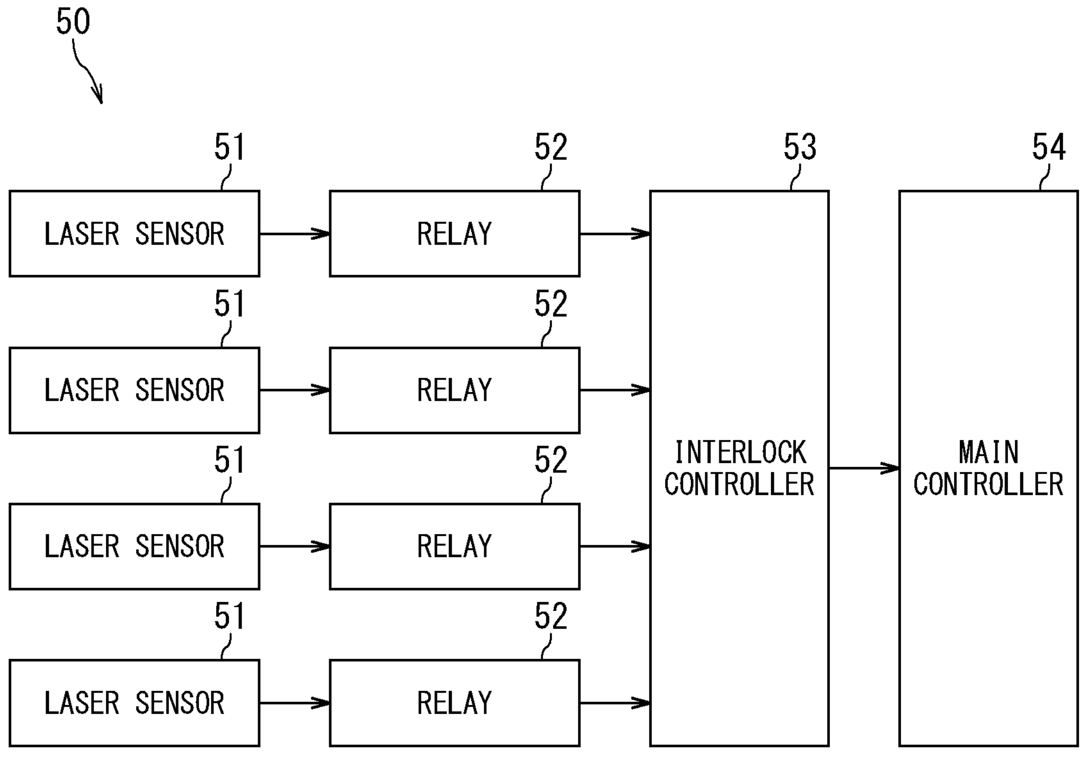
FIG. 9 is a block diagram illustrating a system configuration of a monitoring apparatus according to the first embodiment.

As shown in FIG. 9, the particle beam treatment system 1 according to the first embodiment is provided with a monitoring apparatus 50 for the rotating gantry 5. This monitoring apparatus 50 is provided in order to monitor the winding state of the cables 22.

The monitoring apparatus 50 of the first embodiment includes hardware resources such as a processor and a memory and includes a computer in which information processing by software is achieved with the use of the hardware resources by causing a Central Processing Unit (CPU) to execute various programs. Further, the monitoring method of the first embodiment is achieved by causing the computer to execute the various programs.

The system configuration of the monitoring apparatus 50 for the rotating gantry 5 will be described by referring to the block diagram shown in FIG. 9. The monitoring apparatus 50 according to the first embodiment includes laser sensors 51, relays 52, an interlock controller 53, and a main controller 54. The laser sensors 51 constitute a monitoring unit (or monitoring device) in the first embodiment for monitoring the state of the cables 22 in the spool 23.

The main controller 54 is a computer that centrally and integrally controls the rotating gantry 5 and the particle beam treatment system 1. For example, the main controller 54 controls the rotation of the rotating gantry 5 and the irradiation of the particle beam 7 in the particle beam treatment system 1.

The detection signals of the respective laser sensors 51 are inputted to the interlock controller 53 via the respective relays 52. If the state of the cables 22 in the spool 23 is abnormal, a stop signal is inputted from the interlock controller 53 to the main controller 54, and thereby, the operation of both the rotating gantry 5 and the particle beam treatment system 1 is stopped.

In other words, the interlock controller 53 stops driving the rotating gantry 5 when an abnormality in the cables 22 is detected on the basis of monitoring by the laser sensors 51 (i.e., the monitoring unit). In this manner, the drive of the rotating gantry 5 can be automatically stopped in the event of an abnormality in which the cables 22 are in an irregular winding state.

For example, in the particle beam treatment system 1, the particle beam 7 can be radiated only when an irradiation permission flag is set. The state in which the interlock is released is the state in which the irradiation permission flag is set. The state in which the interlock is activated is the state in which the irradiation permission flag is not set. When the stop signal is inputted from the interlock controller 53 to the main controller 54, the interlock is activated, the irradiation permission flag is cleared to switch the system into the state in which the irradiation permission flag is not set, and consequently, the system cannot radiate the particle beam 7.

As shown in FIG. 4, the laser sensors 51 are fixed to the plate mounts 46 that support the straightening plates 42. In other words, the laser sensors 51 are not affected by the rotation of the rotating gantry 5 and the spool 23, and are installed in a stationary state.

For example, two laser sensors 51 are provided in order to detect whether the winding state of the cables 22 of the first group G1 is irregular or normal. Although not illustrated in FIG. 4, two more laser sensors 51 are further provided in order to detect whether the winding state of the cables 22 of the second group G2 is irregular or normal. In other words, the monitoring apparatus 50 according to the first embodiment includes a total of four laser sensors 51. Note that five or more laser sensors 51 may be arranged along the circumferential direction of the spool 23.

The two laser sensors 51 (i.e., the monitoring unit) for detecting the winding state of the cables 22 of the first group G1 are disposed so as to correspond to one end (i.e., the left end) and the other end (i.e., the right end) of the specific range R in the X-axis direction. These laser sensors 51 are provided at positions corresponding to the straightening plates 42 in the circumferential direction of the spool 23. In this configuration, if the cables 22 are irregularly wound in the portion of the straightening plates 42, the protrusion of the cables 22 can be detected at the initial stage of the irregular winding.

Figure 8:
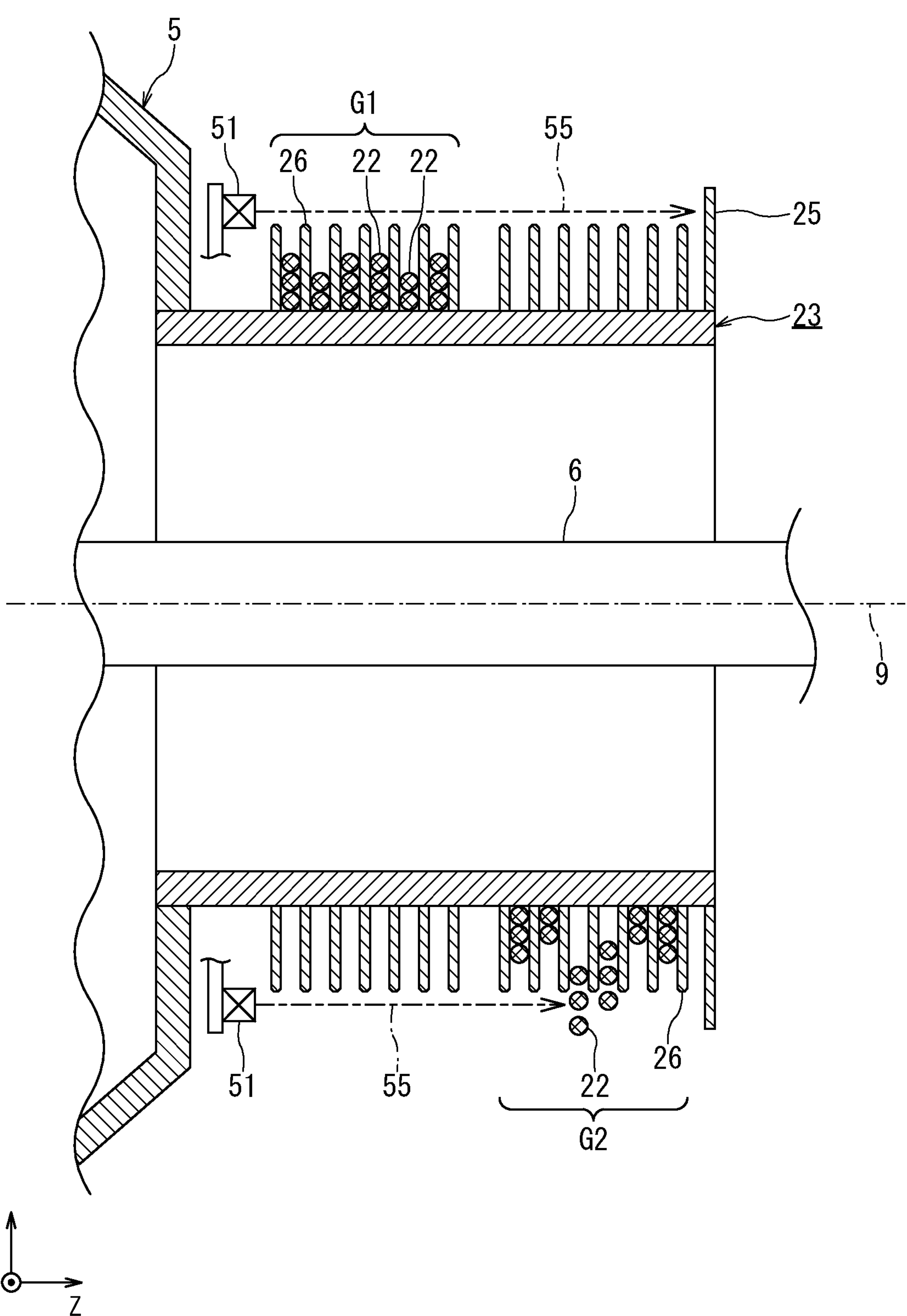
FIG. 8 is a plan view illustrating the spool of the rotating gantry according to the first embodiment.

As shown in FIG. 8, the laser sensors 51 are disposed in a stationary state near the rear portion of the rotating gantry 5, i.e., on the front-end side of spool 23. Each laser sensor 51 emits a laser beam 55 toward the rear. The irregular winding of the cables 22 often occurs on the rear end side of the spool 23 (i.e., on the side of the flange 25), and in that case, the cables 22 protruding from the spool 23 can be prevented from interfering with the laser sensors 51.

Note that the laser sensors 51 are reflective laser sensors 51. In other words, each laser sensor 51 includes an irradiation unit configured to radiate a laser beam 55 and a detection unit (i.e., light receiving unit) configured to detect the laser beam 55 having been radiated onto a predetermined object and then reflected. On the basis of this reflected laser beam 55, the distance from the laser sensor 51 to the object can be detected. On the basis of this detected distance, the system can determine whether the cables 22 are irregularly wound in the spool 23 or not.

If there is no abnormality in the spool 23, the laser beam 55 emitted from each laser sensor 51 is reflected by the flange 25 and detected by the laser sensor 51. Note that the detection distance of each laser sensor 51 may be set in advance to be equal to or shorter than the distance from the laser sensor 51 to the flange 25. In this case, in consideration of presence of the slightly concave and convex portions on the surface of the flanges 25, a distance slightly shorter than the distance from the laser sensor 51 to the flange 25 is set as the detection distance.

Conversely, if the cables 22 are irregularly wound in the spool 23 so as to protrude from the brim disks 26, the laser beams 55 emitted from the respective laser sensors 51 are reflected by the cables 22 and detected by the laser sensors 51. In other words, the laser sensors 51 detect the cables 22 protruding from the brim disks 26 on the basis of the reflection of the laser beams 55 radiated onto the cables 22.

In this configuration, it is sufficient if the laser sensor 51 is provided at one end portion of the spool 23. In addition, this configuration can prevent a situation where the cables 22 protruding from the spool 23 collide with the laser sensors 51 due to the irregular winding.

Each laser sensor 51 radiates the laser beam 55 along the periphery of the brim disk 26 in the axial direction (i.e., in the Z-axis direction) so as to detect the cables 22 protruding from the brim disk 26. In this manner, even if a plurality of cables 22 are provided, the protruding state of each cable 22 can be detected by at least one laser sensor 51, and thus, the installation number of the laser sensors 51 can be reduced.

As shown in FIG. 9, the laser sensors 51 are connected to the interlock controller 53 via the respective relays 52. The operation time of the relays 52 is set to a predetermined period of time. For example, the operation time of relays 52 is set to a range of 20 to 200 milliseconds. If the detection time length by the laser sensors 51 is equal to or longer than the operation time of the relays 52, the relays 52 operate and the detection signals of the respective laser sensors 51 are inputted to the interlock controller 53. Conversely, if the detection time length by the laser sensors 51 is shorter than the operation time of the relays 52, the relays 52 are not activated and the detection signals of the respective laser sensors 51 are not inputted to the interlock controller 53. In this configuration, for example, if the cables 22 momentarily quickly pass through the irradiation range of the laser beam(s) 55, there is no need to activate the interlock. In other words, this configuration can prevent erroneous activation of the interlock in the case where the winding state of the cables 22 is normal.

Figure 10:
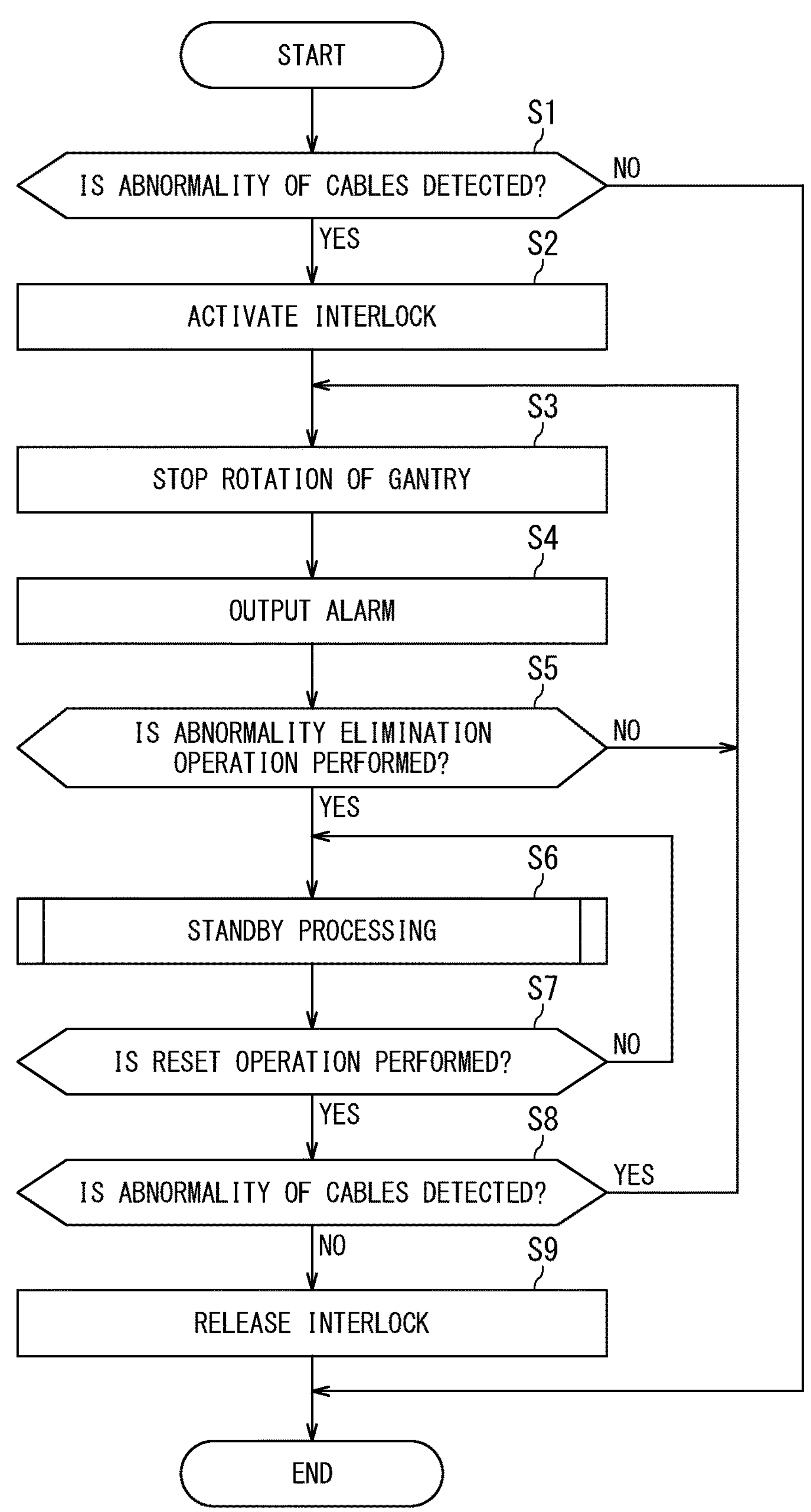
FIG. 10 is a flowchart illustrating a monitoring method for the rotating gantry according to the first embodiment.

Next, a description will be given of the method of monitoring the rotating gantry 5 (i.e., monitoring processing) to be executed by the monitoring apparatus 50 for the rotating gantry 5 on the basis of the flowchart of FIG. 10 by referring to the above-described figures as required. This processing is constantly executed when the rotating gantry 5 and the particle beam treatment system 1 are in operation. The monitoring apparatus 50 executes the monitoring method by repeating this processing.

In the first step S1, the state of the cables 22 in the spool 23 is monitored by the laser sensors 51. During normal operation, the rotating gantry 5 rotates, and the spool 23 winds or unwinds the plurality of cables 22 along with the rotation of the rotating gantry 5. Further, the main controller 54 determines whether the stop signal is inputted from the interlock controller 53 or not. In other words, the main controller 54 determines whether an abnormality in the cables 22 is detected or not. If there is no abnormality in the cables 22 (NO in the step S1), the processing is completed. Conversely, if there is an abnormality in the cables 22 (YES in the step S1), the processing proceeds to the step S2.

In the step S2, the main controller 54 activates the interlock, and the particle beam treatment system 1 stops irradiation of the particle beam 7.

In the next step S3, the main controller 54 stops the rotating gantry 5. In other words, the interlock controller 53 according to the first embodiment stops drive of the rotating gantry 5 via the main controller 54 when an abnormality in the cables 22 is detected on the basis of monitoring by the laser sensors 51 (i.e., the monitoring unit).

In the next step S4, the main controller 54 issues an alarm. An administrator can notice or grasp the occurrence of the abnormality by the issue of this alarm.

In the next step S5, the main controller 54 determines whether an abnormality elimination operation is received or not. If the abnormality elimination operation is not received (NO in the step S5), the processing returns to the step S4. Conversely, if the abnormality elimination operation is received (YES in the step S5), the processing proceeds to the step S6. For example, the administrator or maintenance worker manually presses a predetermined switch to stop the alarm as the abnormality elimination operation. This manual operation stops the alarm and allows the rotating gantry 5 to be rotated for maintenance.

In the step S6, the main controller 54 executes standby processing of waiting until completion of the maintenance work, which is the work of eliminating an abnormality. Here, the worker performs the work of straightening the irregularly wound cables 22 into a regular or normal winding state by rotating the rotating gantry 5, for example.

In the next step S7, the main controller 54 determines whether reset operation is received or not. For example, the administrator or the maintenance worker presses a reset switch as the reset operation when the maintenance work is completed. If the reset operation is not received (NO in the step S7), the processing returns to the step S6. Conversely, if the reset operation is received (YES in the step S7), the processing proceeds to the step S8.

In the step S8, the main controller 54 determines whether the stop signal is inputted from the interlock controller 53 or not. In other words, it is determined whether an abnormality in the cables 22 is detected or not. If there is an abnormality in the cables 22 (YES in the step S8), the processing returns to the step S3. Conversely, if there is no abnormality in the cables 22 (NO in the step S8), the processing proceeds to the step S9.

In the step S9, the main controller 54 releases the interlock, which allows the particle beam treatment system 1 to resume irradiation of the particle beam 7.

Thereafter, the processing is completed. Note that the above-described steps are at least part of the processing included in the monitoring method, and other steps may be included in the monitoring method.

In the first embodiment, the laser sensors 51 can monitor the winding state of the cables 22. For example, in the case where hollow flexible hoses are used to supply the coolant as the cables 22, if these flexible hoses are twisted due to the irregular winding, the supply of the coolant to the superconducting electromagnets 15 is interrupted. For this reason, the configuration of the first embodiment causes the monitoring apparatus 50 to monitor whether the winding state is normal or irregular, and thereby enables a countermeasure for the irregular winding state before the supply of the coolant is interrupted.

Although it is assumed in the first embodiment that the main controller 54 is part of the configuration of the monitoring apparatus 50, another aspect may be adopted. For example, the main controller 54 may not be included in the monitoring apparatus 50. In that case, the interlock controller 53 performs various determination processes or interlock controls.

Although each reflective laser sensor 51 configured as the integration of the irradiation unit and the detection unit (i.e., light receiving unit) is used in the first embodiment, another aspect may be adopted. For example, transmission-type laser sensors, in each of which the irradiation unit and the detection unit are configured as separate units, may also be used.

Although the cable straightening apparatus 40 includes both the straightening wires 41 and the straightening plates 42 in the first embodiment, another aspect may be adopted. For example, the cable straightening apparatus 40 may include either the straightening wires 41 or the straightening plates 42. In other words, it may configured in such a manner that the straightening plates 42 are omitted and the cable straightening apparatus 40 includes only the straightening wires 41. Additionally, or alternatively, it may configured in such a manner that the straightening wires 41 are omitted and the cable straightening apparatus 40 includes only the straightening plates 42.

Note that the straightening wires 41 or the straightening plates 42 may be provided only in the portion (range) where the cables 22 protrude from the spool 23. In addition, depending on the cable straightening apparatus 40, the cables 22 may be grouped by diameter or the cables 22 maybe grouped by type. Since the flexible hoses are different in bending degree from the power lines, both the flexible hoses and the power lines are preferably separated and grouped depending on their types.

Because installing the straightening wires 41 is easier than installing the straightening plates 42 in terms of construction, the construction period and the manufacturing cost can be reduced. In addition, one end of each of the straightening wires 41 may be fixed to the bottom portion of the cable pit 24.

In the particle beam treatment system 1, though the rotating gantry 5 can be downsized by using the superconducting electromagnets 15, hoses for flowing the liquid helium to be used for cooling down the superconducting electromagnets 15 are also required. As a result, the number of the cables 22 increases and the thickness and rigidity of each type of the cables 22 also differ, which increases the difficulty of straightening the cables 22. However, in the first embodiment, the straightening wires 41 or the straightening plates 42 can be provided in an appropriate manner for each type of the cables 22, which facilitates the work of straightening the cables 22.

Figure 11:
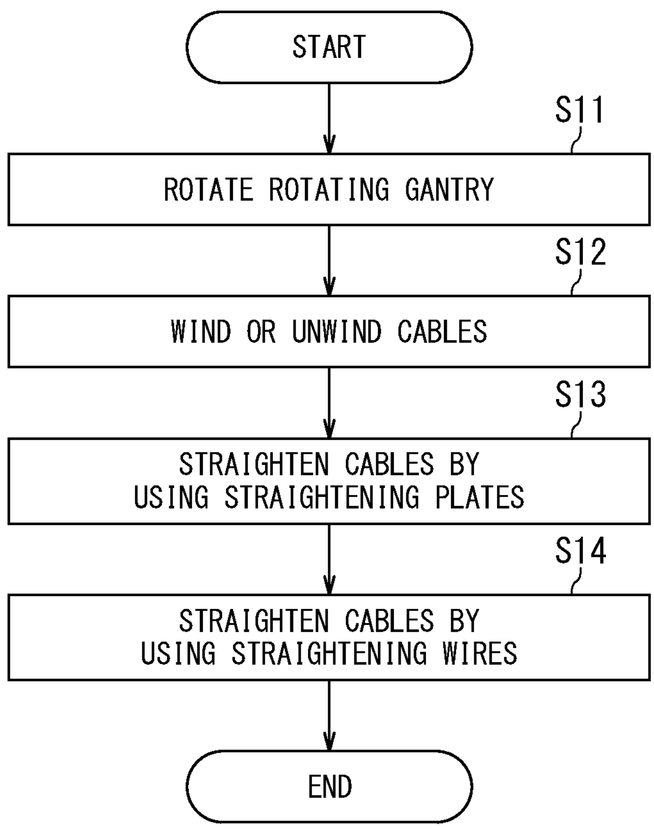
FIG. 11 is a flowchart illustrating a cable straightening method for the rotating gantry according to the first embodiment.

Next, a description will be given of the straightening method for the rotating gantry 5 to be executed by using the cable straightening apparatus 40 on the basis of the flowchart of FIG. 11 by referring to the above-described figures as required.

In the first step S11, the rotating gantry 5 configured to support both the irradiation nozzle 13 for radiating the particle beam 7 and the transport unit 14 for transporting the particle beam 7 to the irradiation nozzle 13 rotates around the horizontal axis 9 directed in the horizontal direction.

In the next step S12, the spool 23 provided on the rotating gantry 5 winds or unwinds the plurality of cables 22, each of which is connected at one end to the rotating gantry 5 and is connected at the other end to the stationary fixing device 30.

In the next step S13, the plurality of straightening plates 42 installed in parallel in a stationary state near the spool 23 partition the plurality of cables 22 arranged in the axial direction.

In the next step S14, the plurality of straightening wires 41, which are laid or bridged laterally below the spool 23 and are provided in a stationary state, partition the plurality of cables 22 that hang down from the spool 23.

Thereafter, the cable straightening method is completed. This cable straightening method is constantly executed and repeated while the rotating gantry 5 is in operation. Note that the above-described steps are at least part of the cable straightening method and other steps may be included in the cable straightening method.

In the first embodiment, the straightening wires 41 of the cable straightening apparatus 40 can suppress wear of the cables 22 while preventing the cables 22 from being irregularly wound. For example, in the case where hollow flexible hoses are used to supply the coolant as the cables 22, if these flexible hoses are twisted due to the irregular winding, the supply of the coolant to the superconducting electromagnets 15 is interrupted. For this reason, the configuration of the first embodiment prevents the flexible hoses from being irregularly wound, and consequently, the supply of the coolant to the superconducting electromagnets 15 is prevented from being interrupted.

Although the cable straightening apparatus 40 includes both the straightening wires 41 and the straightening plates 42 in the first embodiment, another aspect may be adopted. For example, the cable straightening apparatus 40 may include either the straightening wires 41 or the straightening plates 42. In other words, it may configured in such a manner that the cable straightening apparatus 40 includes only the straightening wires 41 and the straightening plates 42 are omitted. Additionally, or alternatively, it may configured in such a manner that the cable straightening apparatus 40 includes only the straightening plates 42 and the straightening wires 41 are omitted.

Note that the straightening wires 41 or the straightening plates 42 may be provided only in the portion (range) where the cables 22 protrude from the spool 23. In addition, depending on the cable straightening apparatus 40, the cables 22 may be grouped by diameter or the cables 22 maybe grouped by type. Since the flexible hoses are different in bending degree from the power lines, both the flexible hoses and the power lines are preferably separated and grouped depending on their types.

Because installing the straightening wires 41 is easier than installing the straightening plates 42 in terms of construction, the construction period and the manufacturing cost can be reduced. In addition, one end of each of the straightening wires 41 may be fixed to the bottom portion of the cable pit 24.

Second Embodiment

Next, the second embodiment will be described by using FIG. 12 to FIG. 14. The same components as those shown in the above-described embodiment are denoted by the same reference signs, and duplicate descriptions are omitted.

Figure 14:
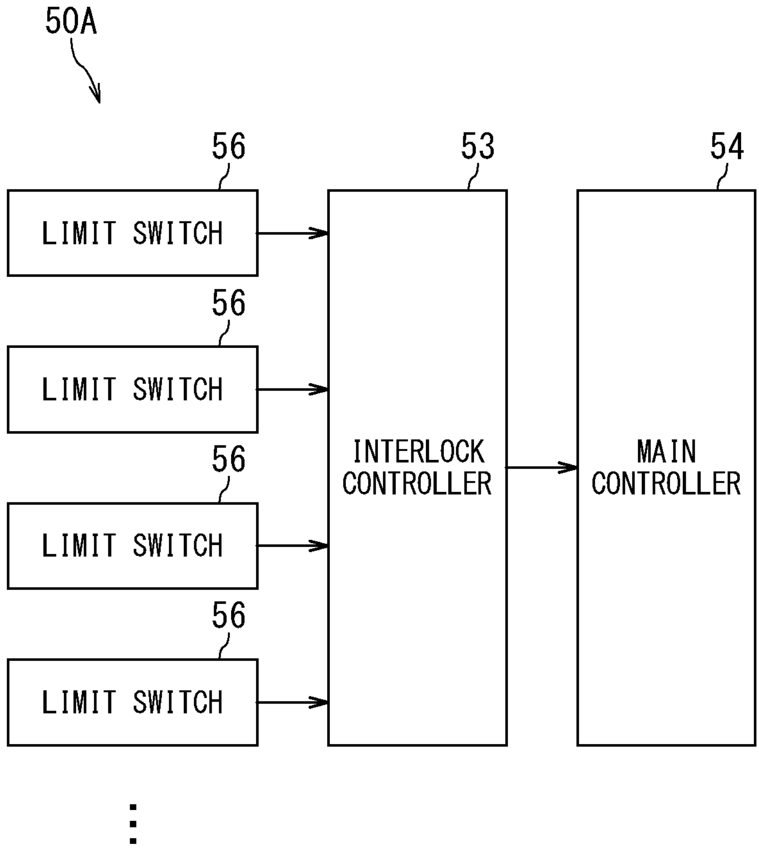
FIG. 14 is a block diagram illustrating a system configuration of the monitoring apparatus according to the second embodiment.

As shown in FIG. 14, the monitoring apparatus 50A for the rotating gantry 5 according to the second embodiment includes limit switches 56, the interlock controller 53, and the main controller 54. Note that the limit switches 56 constitute the monitoring unit (or monitoring device) in the second embodiment for monitoring the state of the cables 22 in the spool 23.

Figure 12:
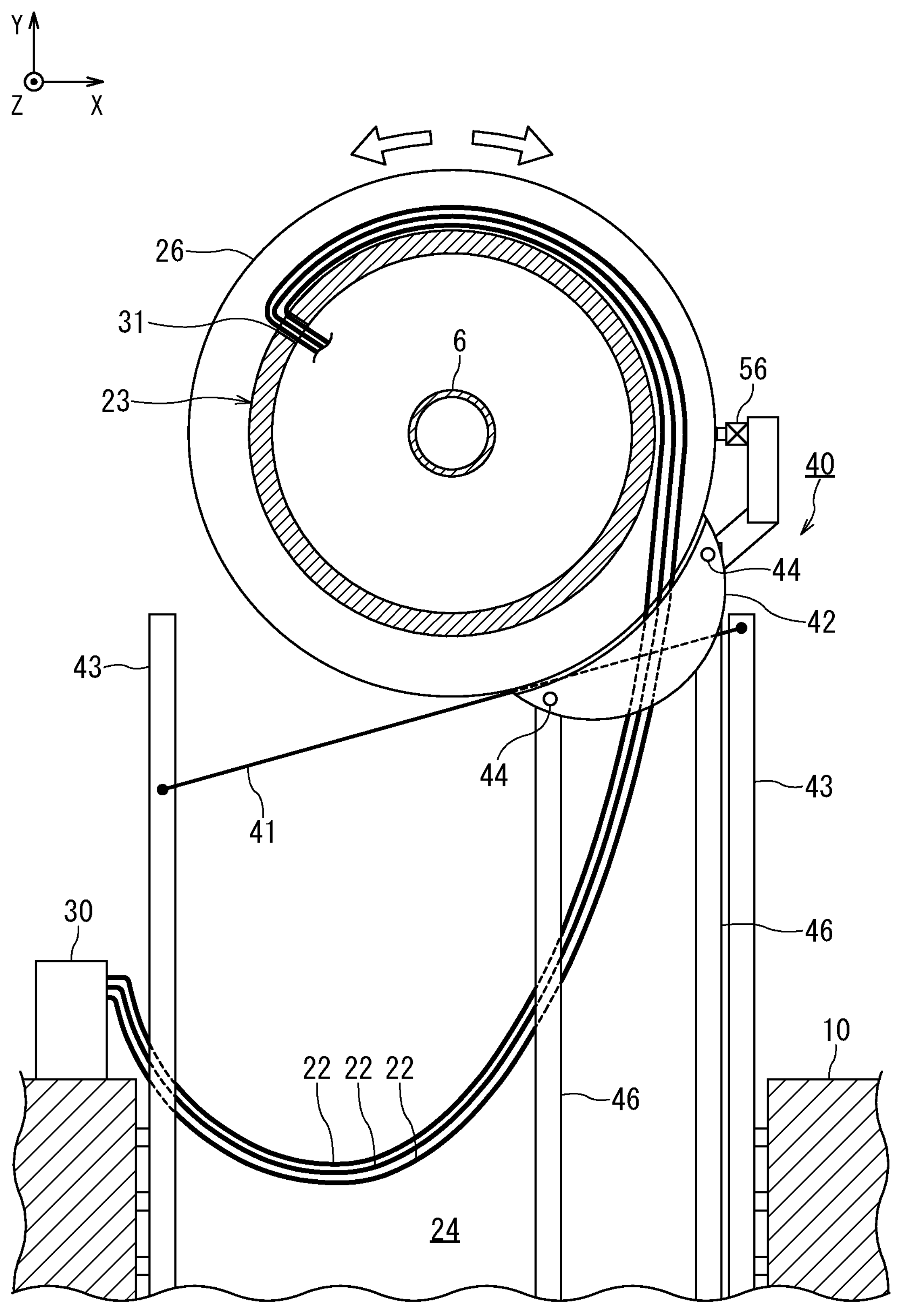
FIG. 12 is a rear view of the rotating gantry according to the second embodiment.

As shown in FIG. 12, the limit switches 56 are fixed to the plate mounts 46 that support the straightening plates 42. In other words, the limit switches 56 are installed in a stationary state without being affected by the rotation of the rotating gantry 5 and the spool 23.

Figure 13:
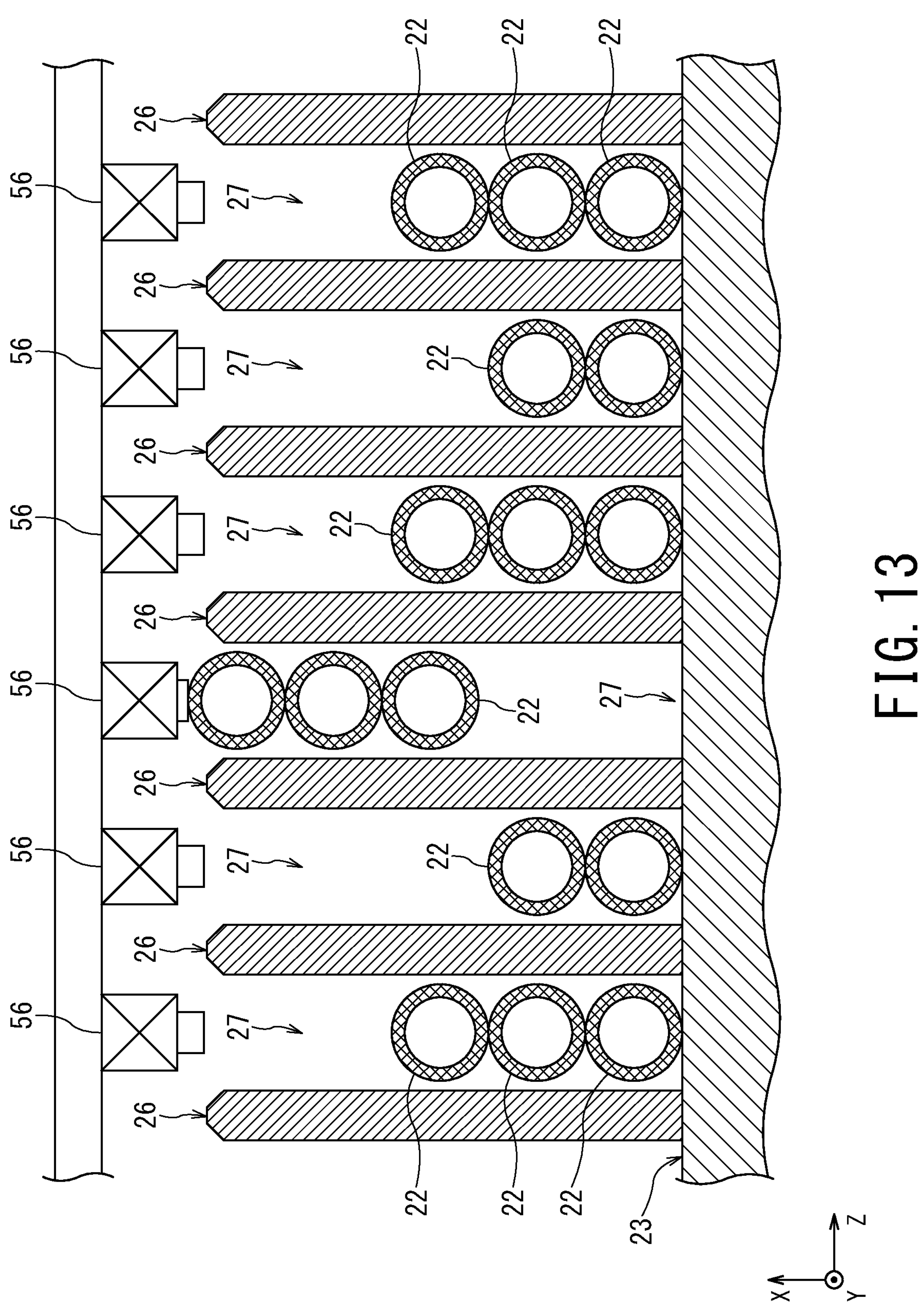
FIG. 13 is a plan view illustrating the brim disks provided with limit switches according to the second embodiment.

As shown in FIG. 13, for example, the limit switches 56 are provided so as to correspond to the respective lanes 27 in order to detect whether the winding state of the cables 22 is normal or irregular. For example, between the brim disks 26, each limit switch 56 is provided at the inlet or entrance of the lane 27. In other words, the number of the installed limit switches 56 is the same as the number of the lanes 27. If the cables 22 are irregularly wound in the spool 23 and the cables 22 held in the lanes 27 protrude from the lanes 27, this protrusion state can be detected by the limit switches 56.

As shown in FIG. 14, the detection signals of the respective limit switches 56 are inputted to the interlock controller 53. If the state of cables 22 in the spool 23 is abnormal, the stop signal is inputted from the interlock controller 53 to the main controller 54, and the operation of both the rotating gantry 5 and the particle beam treatment system 1 is stopped.

In the second embodiment, the winding state of the cables 22 can be monitored by using the limit switches 56. In this configuration, the protruding state of the cables 22 is detected by contact of the cables 22 with the limit switch(es) 56, and consequently, erroneous detection is less likely to occur. In addition, the lane 27 where the cables 22 are protruding can be accurately specified.

Third Embodiment

Next, the third embodiment will be described by using FIG. 15 and FIG. 16. The same components as those shown in the above-described embodiments are denoted by the same reference signs, and duplicate descriptions are omitted.

Figure 16:
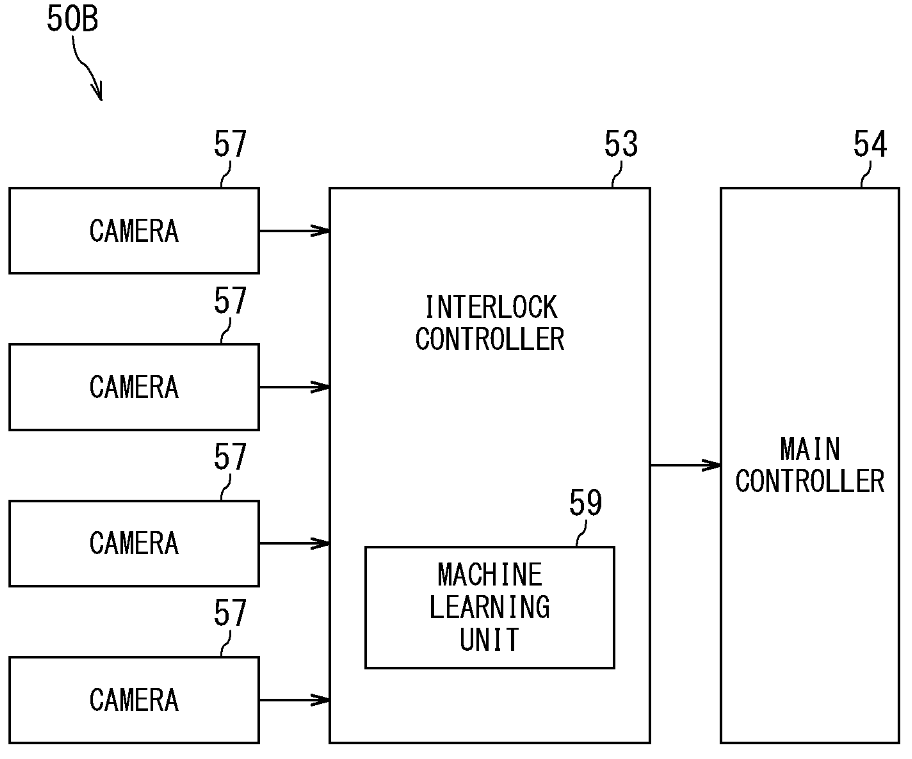
FIG. 16 is a block diagram illustrating a system configuration of the monitoring apparatus according to the third embodiment.

As shown in FIG. 16, the monitoring apparatus 50B for the rotating gantry 5 according to the third embodiment includes cameras 57, the interlock controller 53, and the main controller 54. Note that the cameras 57 constitute the monitoring unit (or monitoring device) in the third embodiment for monitoring the state of the cables 22 in the spool 23.

Figure 15:
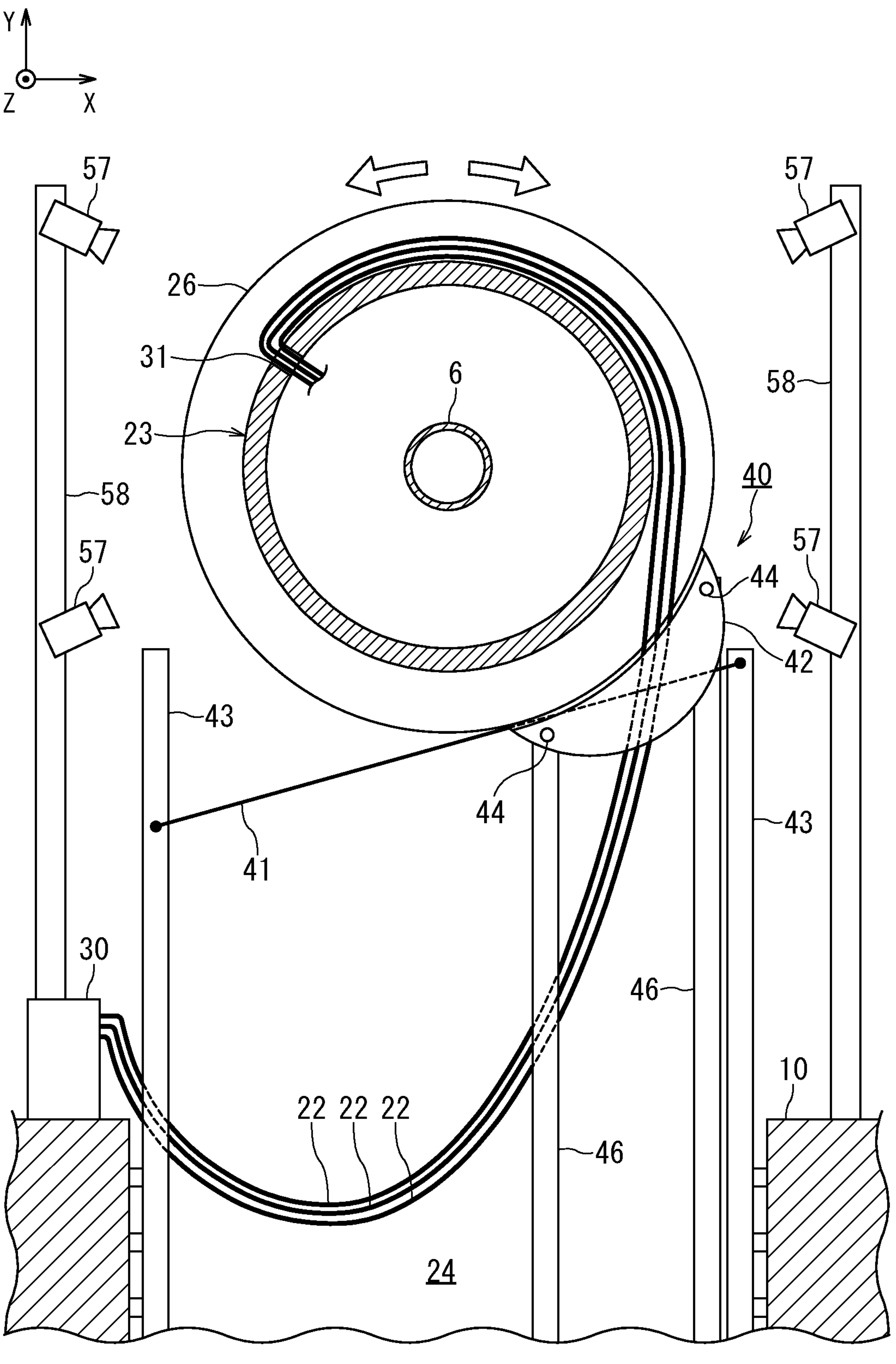
FIG. 15 is a rear view of the rotating gantry according to the third embodiment.

As shown in FIG. 15, camera mounts 58 extending upward are fixed to the structure 10 of the building. For example, on both sides of the spool 23, the plurality of camera mounts 58 spaced apart in the X-axis direction are provided. The plurality of cameras 57 are fixed to these camera mounts 58. Further, the cameras 57 image the spool 23 from the side. Note that the cameras 57 may image the spool 23 from above or from. below. In addition, the cameras 57 may image the spool 23 from the back side.

As shown in FIG. 16, the images of the spool 23 generated by the respective cameras 57 are inputted to the interlock controller 53. Further, on the basis of these images, the interlock controller 53 determines whether the cables 22 are irregularly wound or not. If the cables 22 are irregularly wound, the interlock controller 53 outputs the stop signal to the main controller 54, and thereby stops the operation of both the rotating gantry 5 and the particle beam treatment system 1.

The interlock controller 53 of the third embodiment includes hardware resources such as a Central Processing Unit (CPU), a Read Only Memory (ROM), a Random. Access Memory (RAM) and/or a Hard Disk Drive (HDD) and is configured as a computer in which information processing by software is achieved with the use of the hardware resources by causing the CPU to execute various programs.

The interlock controller 53 includes a machine learning unit 59. In other words, the interlock controller 53 includes a computer having an artificial intelligence (AI) that performs machine learning. Further, the machine learning unit 59 may include a deep learning unit that extracts a specific pattern from a plurality of patterns on the basis of deep learning. The machine learning unit 59 is implemented by causing the CPU to execute the programs stored in the memory or the HDD.

In the third embodiment, machine learning is performed in advance by using the images of the spool 23. The images depicting the spool 23 to be used for the machine learning may be images actually generated by the cameras 57 or may be CG (computer graphics) images that are generated by imitating the images acquired from the cameras 57 on the basis of computer graphics. In addition, the images obtained by the cameras 57 may be edited manually or automatically to generate a wide variety of learning images.

In this manner, on the basis of both the learning images of the normal spool 23 without the irregular winding and the learning images of the abnormal spool 23 on which the cables 22 are irregularly wound, the machine learning unit 59 is constructed as a discriminator that can determine whether the winding state of the cables 22 is normal or abnormal. Further, during actual treatment in which the rotating gantry 5 is in operation, determination images generated by the cameras 57 are inputted to the machine learning unit 59 and are used for determining whether the current winding state of the cables 22 is normal or irregular.

In the analysis using the computer of the third embodiment, an analysis technique based on learning of AI can be used. For example, a learning model generated by machine learning using a neural network, a learning model generated by other machine learning, a deep learning algorithm, or a mathematical algorithm such as regression analysis can be used. In addition, forms of machine learning include forms such as clustering and deep learning.

For example, the interlock controller 53 may be configured by a single computer that includes a neural network or may be configured by a plurality of computers including the neural network.

The above-described neural network is a mathematical model that expresses the characteristics of brain functions by computer simulation. For example, artificial neurons (nodes) that form a network through synaptic connections change the synaptic connection strength through learning and show a model that has acquired problem-solving ability. Furthermore, the neural network acquires problem-solving ability by deep learning.

For example, the neural network is provided with intermediate layers composed of six layers. Each layer of the intermediate layers is composed of, for example, 300 units. In addition, feature amount in a pattern of change in state of a circuit or system can be automatically extracted by causing a multilayer neural network to learn in advance with the use of learning data. On the user interface, the multilayer neural network can set arbitrary number of intermediate layers, arbitrary number of units, arbitrary learning rate, arbitrary number of times of learning, and arbitrary activation function.

The neural network may use deep reinforcement learning in which a reward function is set for each of various information items to be learned and the information item with the highest value is extracted from the various information items on the basis of the reward function.

For example, a Convolution Neural Network (CNN) that has a proven performance in image recognition is used. In this CNN, the intermediate layer is composed of a convolution layer and a pooling layer. The convolution layer obtains a feature map by applying filtering processing to nearby nodes in the previous layer. The pooling layer further reduces the feature map outputted from the convolution layer so as to generate a new feature map. A slight positional shift in feature amount can be absorbed by acquiring the maximum pixel value in the pixels of a target region of the feature map.

The convolution layer extracts local features of the image, and the pooling layer performs processing of integrating or aggregating the local features. In the processing to be executed by the convolution layer and the pooling layer, the image is reduced in size while maintaining the features of the input image. That is, the CNN can greatly compress (abstract) the amount of information that an image has.

Further, the input image can be recognized and the image can be classified by using the abstracted image stored in the neural network.

In deep learning, there are various methods such as an auto encoder, a Recurrent Neural Network (RNN), a Long Short-Term Memory (LSTM), and a Generative Adversarial Network (GAN). These methods may be applied to the deep learning of the third embodiment.

In the third embodiment, the winding state of the cables 22 can be monitored by using the cameras 57. In this configuration, the state of the spool 23 can be obtained as one or more images, which makes it easier to determine whether the current winding state of the cables 22 is normal or irregular.

On the basis of the images of the spool 23 generated by the cameras 57, the administrator can determine whether the cables 22 are irregularly wound or not. Further, the administrator may press an emergency stop button so as to manually stop operation of both the rotating gantry 5 and the particle beam treatment system 1.

Fourth Embodiment

Next, the fourth embodiment will be described by using FIG. 17 to FIG. 20. The same components as those shown in the above-described embodiments are denoted by the same reference signs, and duplicate descriptions are omitted.

The particle beam treatment system 1 according to the fourth embodiment includes a cable straightening apparatus 60 for the rotating gantry 5. The cable straightening apparatus 60 includes cable straightening units 61 (or cable straightening devices 61). The plurality of cables 22 pass through one of the cable straightening units 61. Further, the cable straightening apparatus 60 is provided in order to straighten the plurality of cables 22 and suppress wear of the cables 22 while preventing the cables 22 from being irregularly wound.

Figure 17:
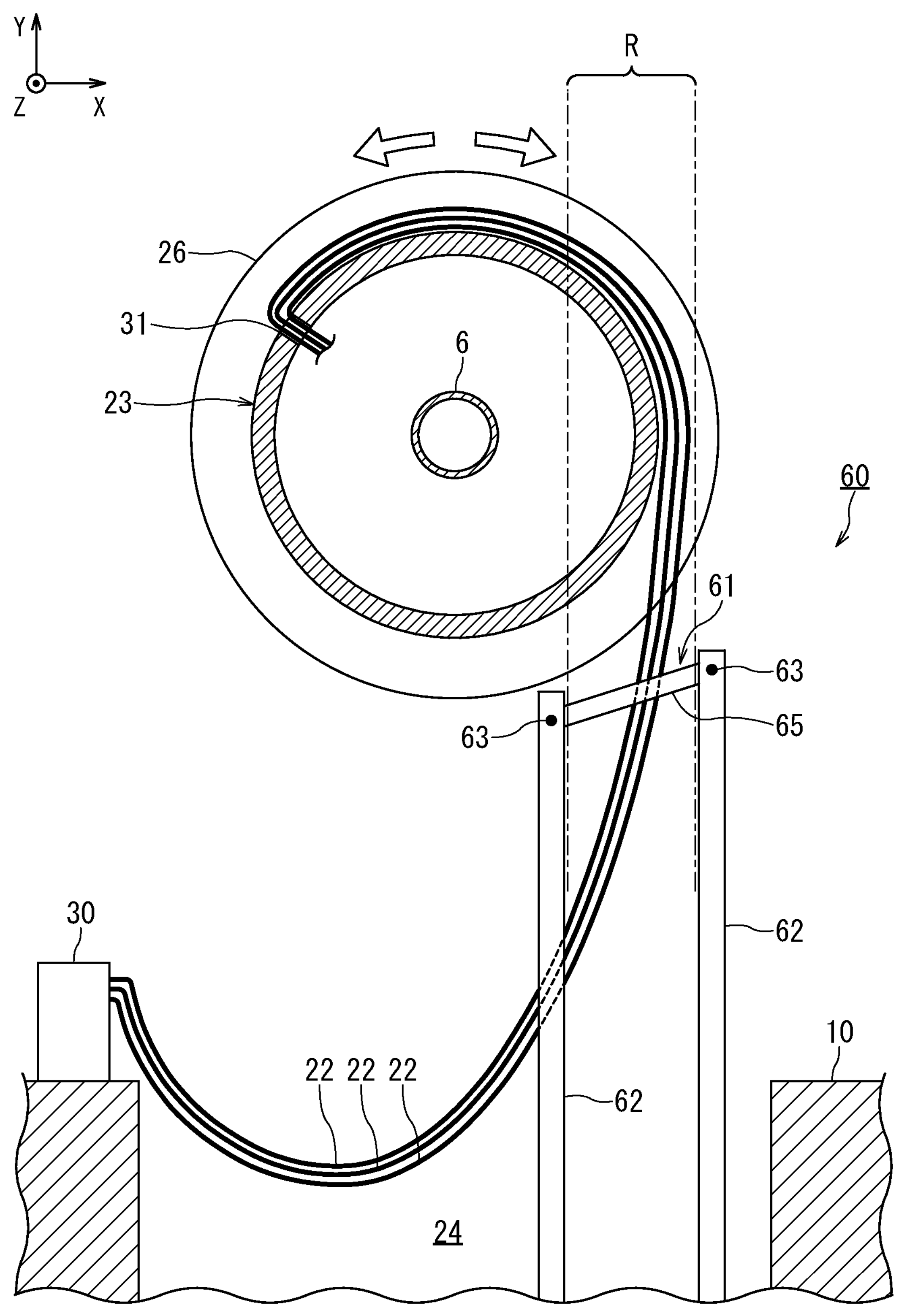
FIG. 17 is a rear view of the rotating gantry according to the fourth embodiment.

One of the cable straightening units 61 is provided for straightening the cables 22 of the first group G1, and the other of the cable straightening units 61 is provided for straightening the cables 22 of the second group G2. In FIG. 17, in order to avoid complicated illustration and prompt understanding, only the cable straightening unit 61 for the first group G1 is illustrated, and illustration of the cable straightening unit 61 for the second group G2 is omitted. Both the cable straightening unit 61 for the first group G1 and the cable straightening unit 61 for the second group G2 are the same in terms of configuration, and are arranged to be bilaterally symmetrical with respect to the rotating gantry 5.

In FIG. 17, in order to facilitate understanding, the width dimension of the cable straightening unit 61 is exaggerated compared to the actual size. Each of the actual cable straightening units 61 is a smaller device than the one shown in FIG. 17. In terms of width dimension, it is sufficient that the width of each cable straightening unit 61 is wide enough to allow at least the plurality of cables 22 to pass through. The width dimension of each cable straightening unit 61 is set as an appropriate width depending on the thickness and number of the cables 22 that pass through it.

Onto the structure 10 in which the cable pit 24 is formed, unit mounts 62 extending upward from the bottom surface of the cable pit 24 are fixed. For example, each cable straightening unit 61 is provided with a pair of left and right unit mounts 62 spaced apart in the X-axis direction. The respective cable straightening units 61 are supported near the top of these unit mounts 62. In the fourth embodiment, connecting portions 63 (FIG. 18) of each cable straightening unit 61 are fixed to the unit mounts 62. In other words, each cable straightening unit 61 is installed in a stationary state in the vicinity of the spool 23.

In addition, each cable straightening unit 61 is provided in an inclined state with respect to the horizontal direction. For example, each cable straightening unit 61 is fixed to the unit mounts 62 in such a manner that one connecting portion 63 of this cable straightening unit 61 is higher than the other connecting portion 63 of this cable straightening unit 61. In the fourth embodiment, each cable straightening unit 61 is provided on the outer circumferential surface of the spool 23 so as to extend to the position directly below the center of the spool 23 from the position where the cables 22 hang down. Further, each cable straightening unit 61 is inclined in such a manner that the end portion closer to the position directly below the center of the spool 23 is lower than the opposite end portion.

Figure 18:
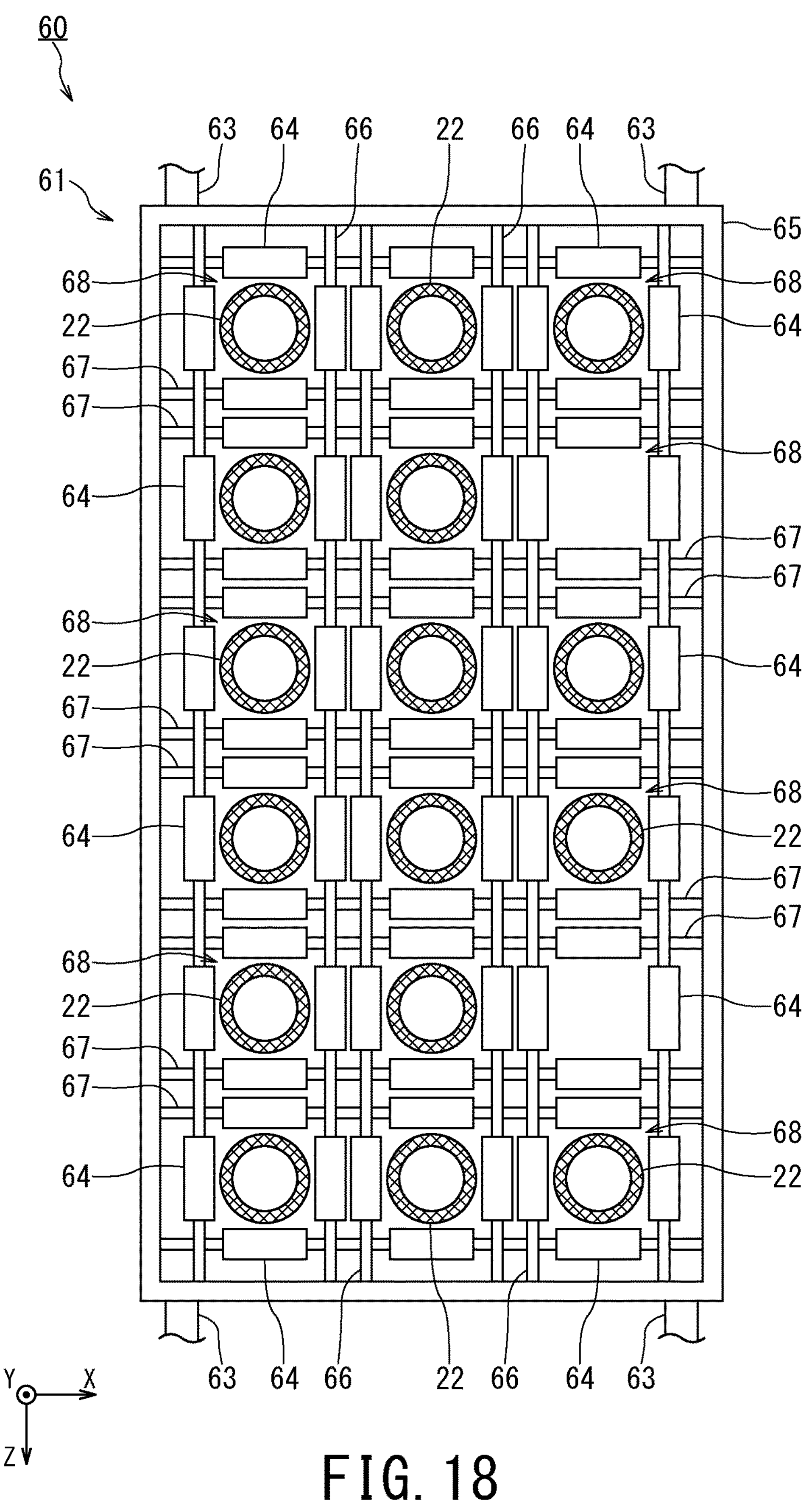
FIG. 18 is a plan view illustrating each cable straightening unit according to the fourth embodiment.

As shown in FIG. 18, each cable straightening unit 61 includes a plurality of rotating bodies 64 and a frame 65. Each rotating body 64 is a cylindrical member. These rotating bodies 64 constitute guide wheels for guiding the cables 22. These rotating bodies 64 are supported in a rotatable state with respect to the frame 65. In other words, these rotating bodies 64 are members that partition the plurality of cables 22, contact the cables 22 at their outer circumferential surfaces, and are rotatable in conjunction with the movement of the cables 22.

The rotating bodies 64 partition the plurality of cables 22 arranged in the radial direction and the axial direction of the rotating gantry 5. In this configuration, the cables 22 are partitioned in the radial direction and the axial direction of the rotating gantry 5, and thus, the cables 22 are sufficiently prevented from being irregularly wound. As to arrangement of the rotating bodies 64, it is sufficient that the rotating bodies 64 partition the plurality of cables 22 arranged in at least one of the radial direction or the axial direction of the rotating gantry 5.

The frame 65 is a member in a lattice shape. For example, the frame 65 is provided with a plurality of rod-shaped shaft portions 66 and 67 that rotatably support the rotating bodies 64. The frame 65 includes: the plurality of shaft portions 66 that extend in the axial direction of the rotating gantry 5 (i.e., in the Z-axis direction) and are arranged in the radial direction (i.e., in the X-axis direction); and the plurality of shaft portions 67 that extend in the radial direction of the rotating gantry 5 (i.e., in the X-axis direction) and are arranged in the axial direction (i.e., in the Z-axis direction). These shaft portions 66 and 67 intersect each other at right angles so as to form a plurality of squares 68.

The respective cables 22 individually pass through the squares 68 in such a manner that one cable 22 passes through one square 68. In addition, the rotating bodies 64 are rotatably supported by the shaft portions 66 and 67 corresponding to the respective four sides of the squares 68. The outer circumferential surface of one cable 22 can be contacted by four rotating bodies 64. In this configuration, the squares 68 separate the plurality of cables 22, and the cables 22 can be slid by the rotating bodies 64. Further, the cables 22 are partitioned, thereby unintentional contact between the cables 22 is suppressed, and thus, the cables 22 are sufficiently prevented from being irregularly wound.

In other words, the cable straightening unit 61 has the frame 65 (shaft portions 66 and 67) on which the rotating bodies 64 partitioning the cables 22 in the radial direction of the rotating gantry 5 (i.e., in the X-axis direction) are rotatably supported. In this configuration, the plurality of cables 22 are partitioned in the radial direction by the frame 65, and the rotating bodies 64 allow the cables 22 to slide while sufficiently preventing the cables 22 from being irregularly wound.

In the fourth embodiment as shown in FIG. 17, the specific range R in which the cables 22 hang down from the spool 23 is set in advance. For example, the cables 22 hang down from the end portion of the spool 23 in the X-axis direction, and a predetermined range including this portion is set as the specific range R. This specific range R is the range in which the cables 22 hang down almost in the gravitational direction due to their own weight. The cable straightening unit 61 is disposed in this specific range R.

Figure 19:
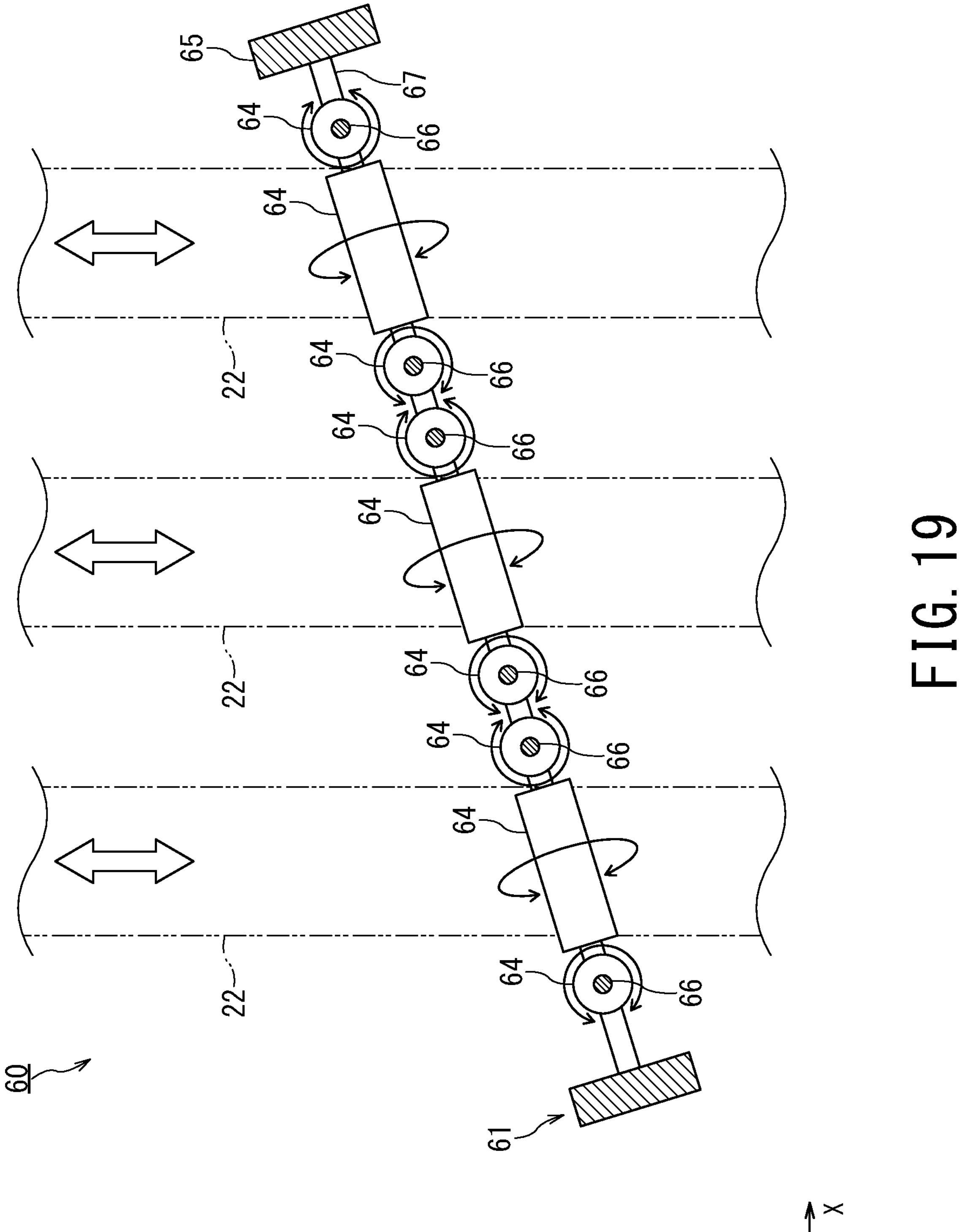
FIG. 19 is a rear view illustrating the cable straightening unit according to the fourth embodiment.

As shown in FIG. 19, the cables 22 hanging down from the spool 23 pass vertically between the rotating bodies 64 that are arranged in the directions of intersecting the extending direction of the cables 22 (i.e., the X-axis direction and the Z-axis direction). In this configuration, the plurality of cables 22 hanging down from the spool 23 can be partitioned.

In addition, the frame 65 is installed in an inclined state with respect to the horizontal direction. Further, when viewed from the rear, the positions at which the respective rotating bodies 64 are installed are different in height. In other words, the positions of the plurality of rotating bodies 64 partitioning the plurality of cables 22 arranged in the radial direction of the rotating gantry 5 are different in height from each other. In this configuration, the cables 22 pass through the cable straightening unit 61 while smoothly contacting the rotating bodies 64.

Figure 20:
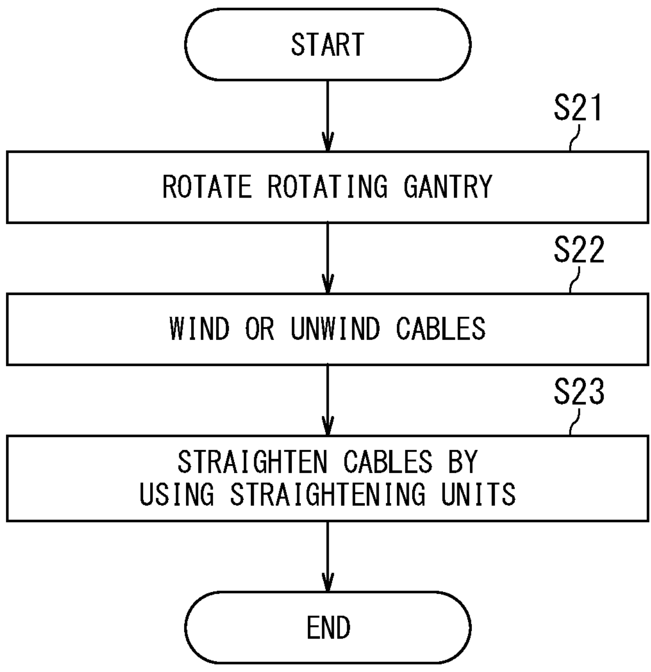
FIG. 20 is a flowchart illustrating the cable straightening method for the rotating gantry according to the fourth embodiment.

Next, a description will be given of the cable straightening method for the rotating gantry 5 to be performed by using the cable straightening apparatus 60 on the basis of the flowchart of FIG. 20 by referring to the above-described figures as required.

In the first step S21, the rotating gantry 5 configured to support both the irradiation nozzle 13 for radiating the particle beam 7 and the transport unit 14 for transporting the particle beam 7 to the irradiation nozzle 13 rotates around the horizontal axis 9 directed in the horizontal direction.

In the next step S22, the spool 23 provided on the rotating gantry 5 winds or unwinds the plurality of cables 22, which are connected at one end to the rotating gantry 5 and are connected at the other end to the stationary fixing device 30.

In the next step S23, the plurality of cables 22 are partitioned by each cable straightening unit 61, which is installed in a stationary state near the spool 23 and includes the plurality of cylindrical rotatable rotating bodies 64 to be brought into contact with the cables 22 at their outer circumferential surfaces.

Thereafter, the cable straightening method is completed. This cable straightening method is constantly executed and repeated while the rotating gantry 5 is in operation. Note that the above-described steps are at least part of the processing included in the cable straightening method, and other steps may be included in the cable straightening method.

The configuration of the fourth embodiment using the cable straightening apparatus 60 can suppress wear of the cables 22 while preventing the cables 22 from being irregularly wound. For example, in the case where hollow flexible hoses are used to supply the coolant as the cables 22, if these flexible hoses are twisted due to the irregular winding, the supply of the coolant to the superconducting electromagnets 15 is interrupted. For this reason, the configuration of the fourth embodiment prevents the flexible hoses from being irregularly wound, and consequently, the supply of the coolant to superconducting electromagnets 15 is prevented from being interrupted.

Although each cable straightening unit 61 in the fourth embodiment is inclined in such a manner that the end portion closer to the position directly below the center of the spool 23 is lower than the opposite end portion, another aspect may be adopted. For example, the cable straightening unit 61 may be inclined in such a manner that the end portion closer to the position directly below the center of the spool 23 is higher than the opposite end portion.

Fifth Embodiment

Next, the fifth embodiment will be described by using FIG. 21 to FIG. 23. The same components as those shown in the above-described embodiments are denoted by the same reference signs, and duplicate descriptions are omitted.

Figure 21:
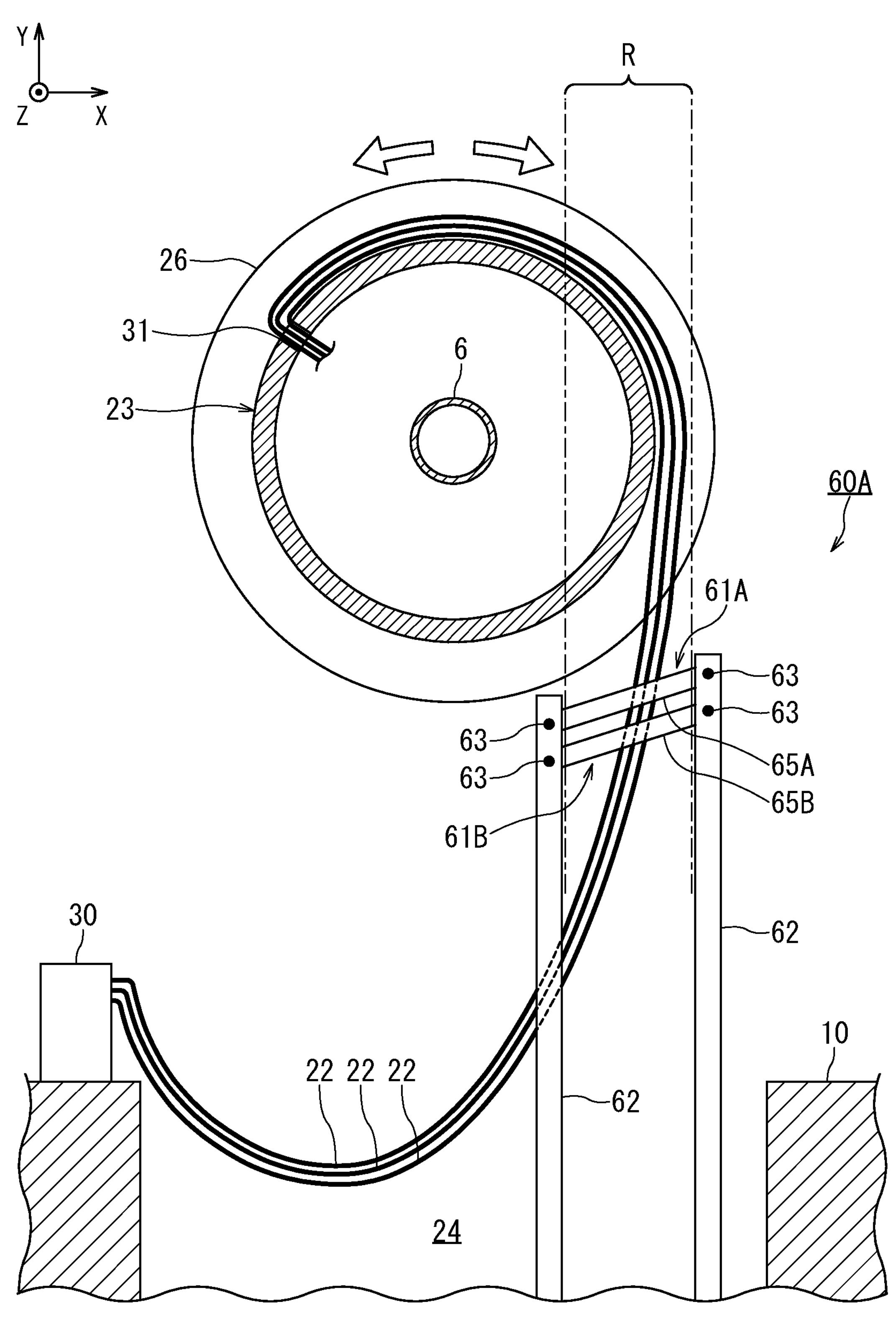
FIG. 21 is a rear view of the rotating gantry according to the fifth embodiment.

As shown in FIG. 21, the cable straightening apparatus 60A according to the fifth embodiment includes an upper cable straightening unit 61A and a lower cable straightening unit 61B that are configured as a pair or double-stage structure. Both connecting portions 63 of each of the cable straightening units 61A and 61B are fixed to both unit mounts 62. In other words, both the cable straightening units 61A and 61B are installed in a stationary state at positions close to the spool 23. The inclinations of both the cable straightening units 61A and 61B are the same as each other.

Figure 22:
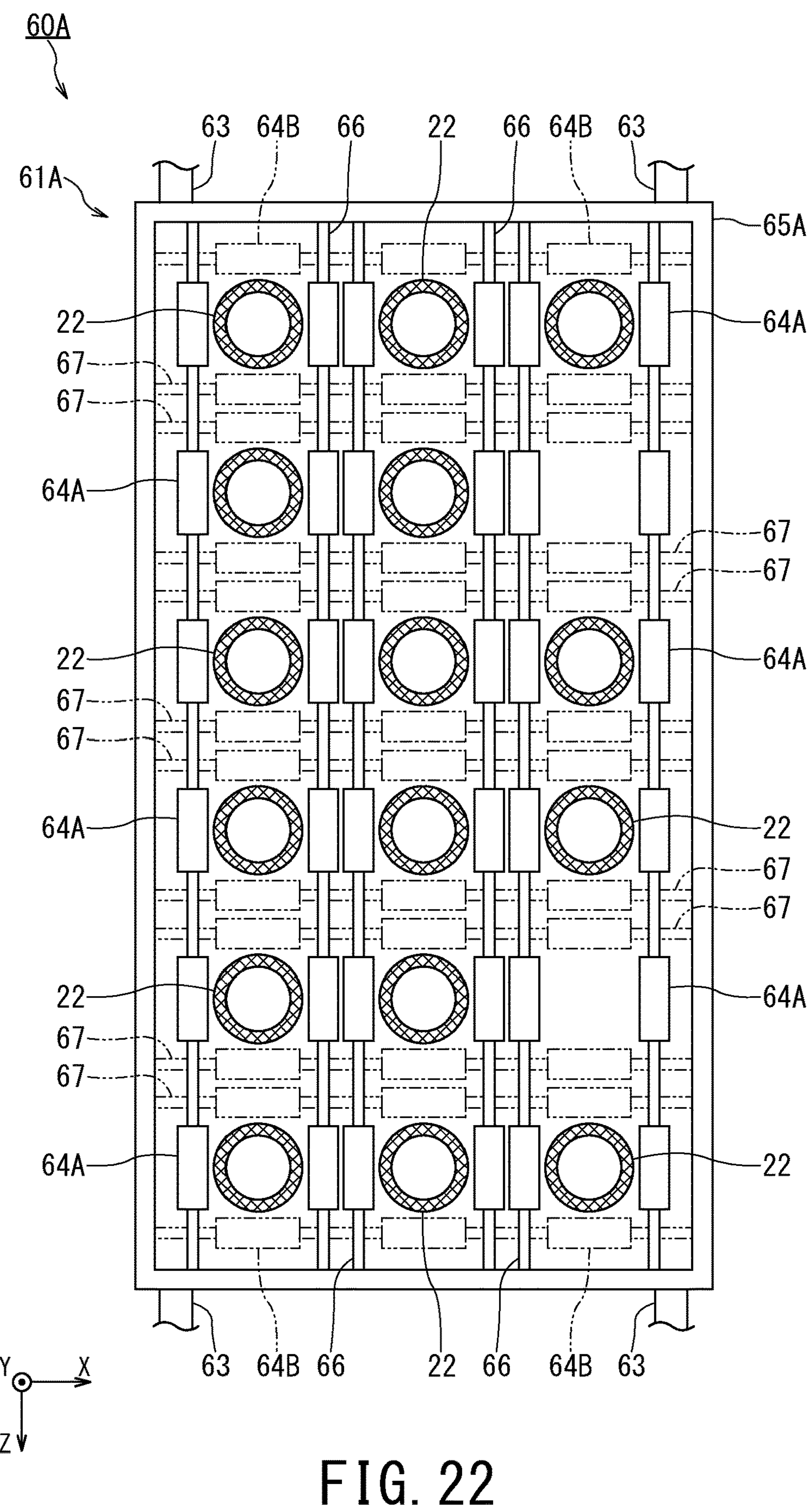
FIG. 22 is a plan view illustrating the cable straightening unit according to the fifth embodiment.
Figure 23:
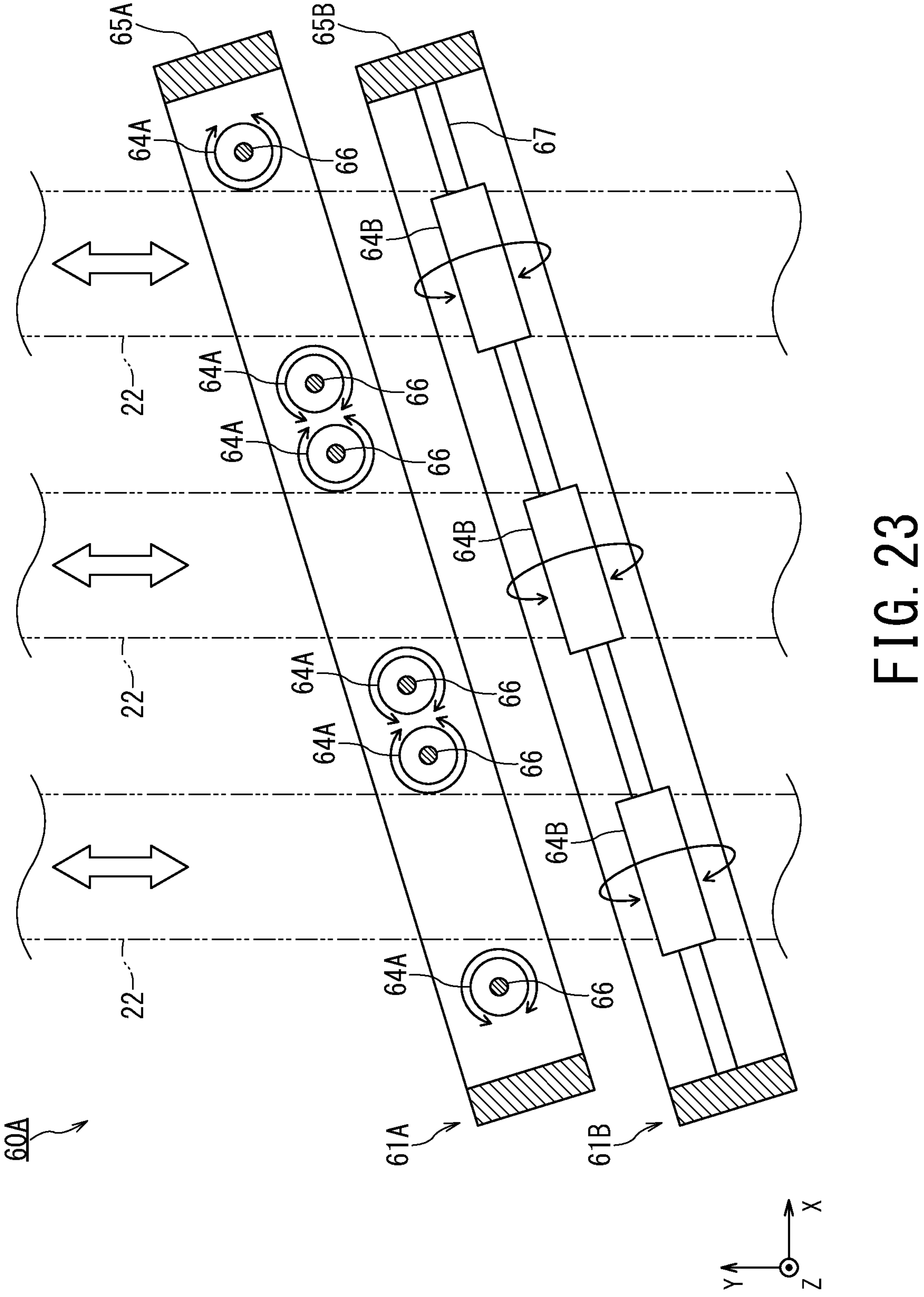
FIG. 23 is a rear view illustrating the cable straightening unit according to the fifth embodiment.

As shown in FIG. 22 and FIG. 23, an upper frame 65A and a lower frame 65B, which are configured as a pair (multiple) or double-stage structure and constitute the respective cable straightening units 61A and 61B, are stacked in the direction in which the cables 22 extend. The separation width of these frames 65A and 65B is appropriately set depending on the type, thickness, and hardness (rigidity) of the cables 22. For example, in the case of guiding the cables 22 that are hard and difficult to be bent, the separation width of these frames 65A and 65B is set to be large enough to prevent the cables 22 from being bent too much at the portions of the cable straightening units 61A and 61B.

In addition, the lower frame 65B is provided directly below the upper frame 65A. Note that the lower frame 65B may be disposed so as to be horizontally shifted from the position directly below the upper frame 65A. For example, the lower frame 65B maybe disposed in the direction in which the cables 22 bend.

The upper frame 65A is provided with a plurality of shaft portions 66 that extend in the axial direction (i.e., in the Z-axis direction) and are arranged in the radial direction (i.e., in the X-axis direction). Rotating bodies 64A are rotatably supported by these shaft portions 66. Similarly, the lower frame 65B is provided with a plurality of shaft portions 67 that extend in the radial direction (i.e., in the X-axis direction) and are arranged in the axial direction (i.e., in the Z-axis direction). Rotating bodies 64B are rotatably supported by these shaft portions 67.

These frames 65A and 65B are stacked in the up-and-down direction, and thereby, the shaft portions 66 and 67 as a whole form lattice arrangement in a plan view. Further, the cables 22 are partitioned both in the axial direction and in the radial direction by the rotating bodies 64A and 64B that are supported by the shaft portions 66 and 67. The outer circumferential surface of each cable 22 can be brought into contact with four rotating bodies 64A and 64B.

In the fifth embodiment, the upper frame 65A is provided with the rotating bodies 64A that partition the cables 22 in the radial direction of the rotating gantry 5 (i.e., in the X-axis direction), and the lower frame 65B is provided with the rotating bodies 64B that partition the cables 22 in the axial direction of the rotating gantry (i.e., in the Z-axis direction). In this configuration, the plurality of rotating bodies 64A and 64B are compactly configured, and thus, the vertical and horizontal dimensions of the cable straightening units 61A and 61B can be reduced.

Since the upper and lower cable straightening units 61A and 61B are provided as the double-stage structure, the cables 22 are not bent suddenly at the portions to be guided by the cable straightening units 61A and 61B, and consequently, wear of the cables 22 can be suppressed.

Although the upper and lower cable straightening units 61A and 61B are provided in the fifth embodiment, another aspect may be adopted. For example, three or more cable straightening units may be arranged in a stacked manner.

Although the inclinations of the upper and lower cable straightening units 61A and 61B are the same as each other in the fifth embodiment, another aspect may be adopted. For example, the respective inclinations of the upper and lower cable straightening units 61A and 61B may be different from each other. In particular, when viewed from the rear, the upper and lower cable straightening units 61A and 61B may be inclined so as to intersect perpendicularly with respect to the direction in which the cables 22 extend.

Sixth Embodiment

Next, the sixth embodiment will be described by using FIG. 24 and FIG. 25. The same components as those shown in the above-described embodiments are denoted by the same reference signs, and duplicate descriptions are omitted.

Figure 24:
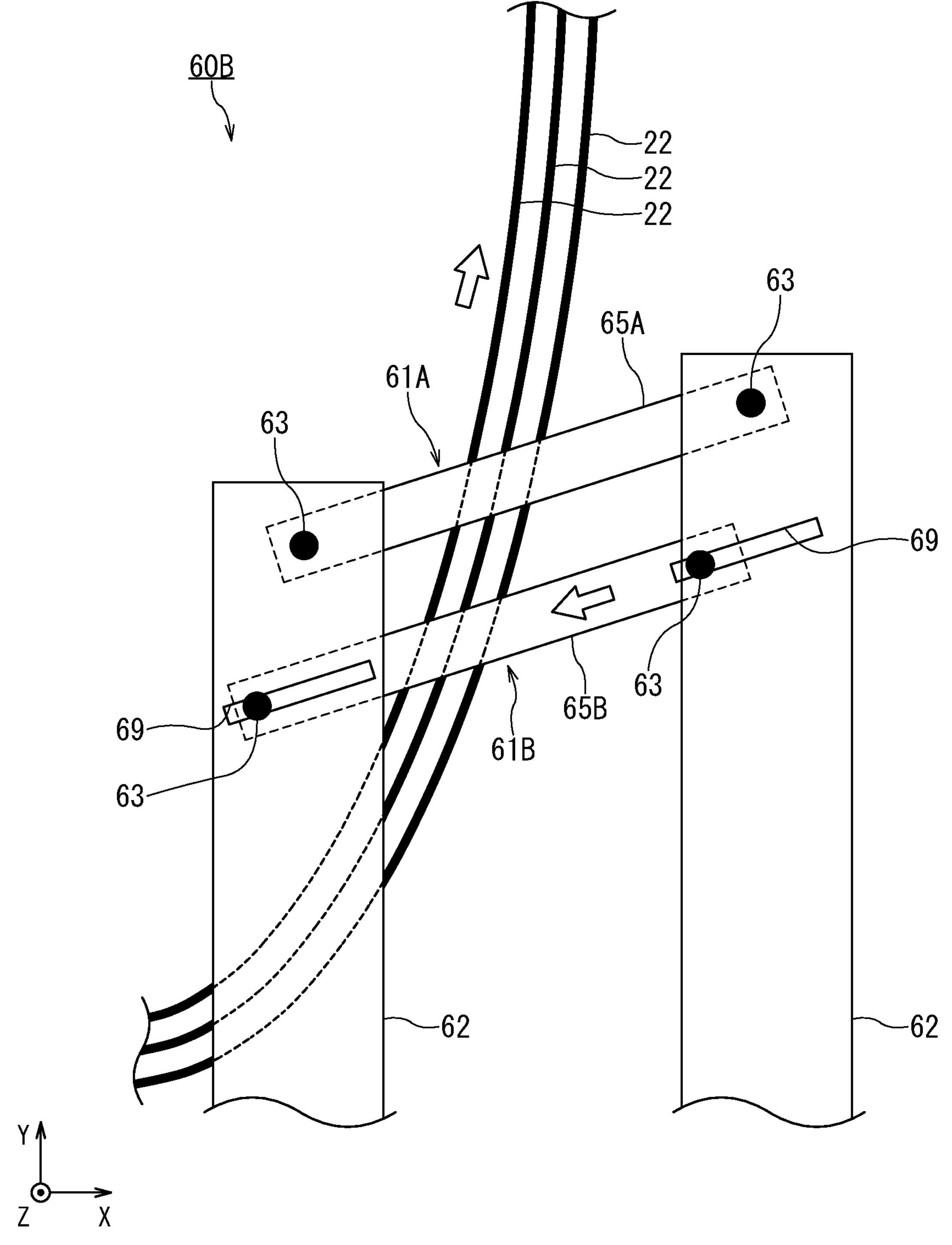
FIG. 24 is a rear view illustrating the cable straightening units according to the sixth embodiment at the time of winding the cables.

As shown in FIG. 24, the cable straightening apparatus 60B according to the sixth embodiment includes an upper cable straightening unit 61A and a lower cable straightening unit 61B that are configured as a pair or double-stage structure. The upper cable straightening unit 61A is fixed to unit mounts 62, whereas the lower cable straightening unit 61B is movably supported on the unit mounts 62. In each of the cable straightening units 61A and 61B, the arrangement of the rotating bodies 64A and 64B is similar to the arrangement in the fifth embodiment (as illustrated in FIGS. 22 and FIG. 23, for example).

For example, the connecting portions 63 of the upper frame 65A are fixed to the unit mounts 62, whereas the connecting portions 63 of the lower frame 65B are supported through slit holes 69 formed in the respective unit mounts 62. The slit holes 69 extend laterally and serve as guide portions that guide the lower frame 65B laterally.

The slit holes 69 are formed so as to be inclined with respect to the horizontal direction. This inclination is the same as the inclination of the cable straightening units 61A and 61B. For example, when no load is applied to the lower frame 65B, the lower frame 65B is moved diagonally downward (to the left in FIG. 24) by its own weight.

Figure 25:
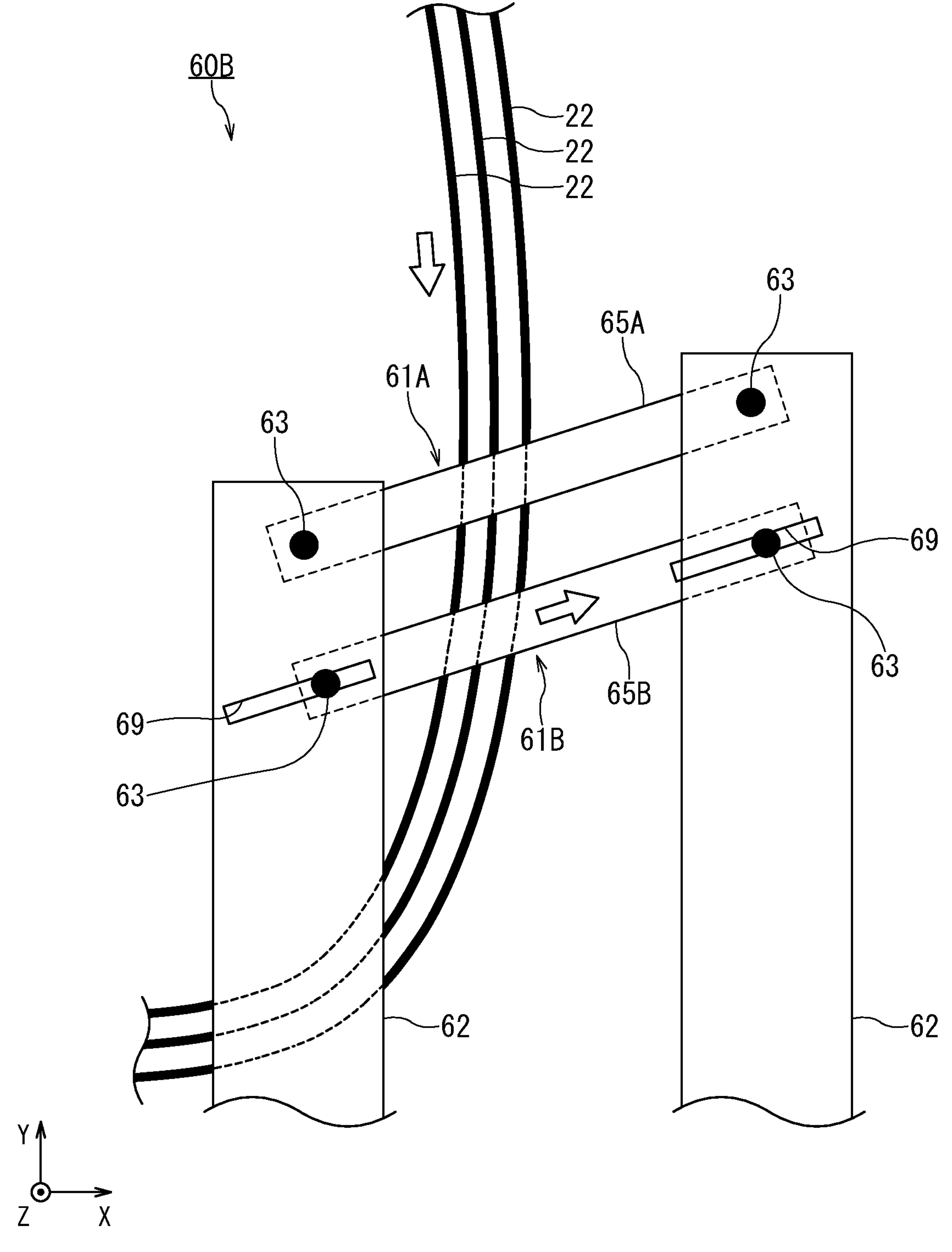
FIG. 25 is a rear view illustrating the cable straightening units according to the sixth embodiment at the time of unwinding the cables.

As shown in FIG. 25, in the case of unwinding the cables 22 from the spool 23 (FIG. 17), the lower frame 65B is moved diagonally upward (to the right in FIG. 25) in accordance with the direction in which the cables 22 extend. For example, when the cables 22 are unwound from the spool 23, the cables 22 are bent so as to bulge away from the spool 23, and thereby, the lower frame 65B moves in accordance with this bending degree.

As shown in FIG. 24, when the cables 22 are wound onto the spool 23 (FIG. 17), the lower frame 65B is moved diagonally downward (to the left in FIG. 24) in accordance with the direction in which the cables 22 extend. For example, when the cables 22 are wound onto the spool 23, the cables 22 are bent in the direction in which the cables 22 are pulled toward the spool 23, and thereby, the lower frame 65B moves in accordance with this bending degree.

In the sixth embodiment, the upper frame 65A is fixed, and the lower frame 65B is movable. Hence, the positional relationship between the double-stage frames 65A and 65B is adjusted in the direction in which the cables 22 extend, and thus, each of the frames 65A and 65B is moved to an appropriate position with respect to the cables 22. In this configuration, the cables 22 pass between the rotating bodies 64A and 64B (FIG. 22 and FIG. 23) at an appropriate angle. In particular, the lower frame 65B is movable in the direction of intersecting the extending direction of the cables 22. In this configuration, the frame 65B moves in accordance with the movement of the cables 22, and thus, any load is not applied to the cables 22 at the respective portions of the cable straightening units 61A and 61B.

Although the upper frame 65A is fixed and the lower frame 65B is movable in the sixth embodiment, another aspect may be adopted. For example, it may be configured in such a manner that the lower frame 65B is fixed and the upper frame 65A is movable. In addition, it may be configured in such a manner that both the upper and lower frames 65A and 65B are movable.

Although the unit mounts 62 are provided with the slit holes 69 as the configuration for moving the lower frame 65B (the cable straightening unit 61B) in the sixth embodiment, another aspect may be adopted. For example, the unit mounts 62 may be provided with rails (i.e., convex rails) for moving the lower frame 65B.

Seventh Embodiment

Next, the seventh embodiment will be described by using FIG. 26 and FIG. 27. The same components as those shown in the above-described embodiments are denoted by the same reference signs, and duplicate descriptions are omitted.

Figure 26:
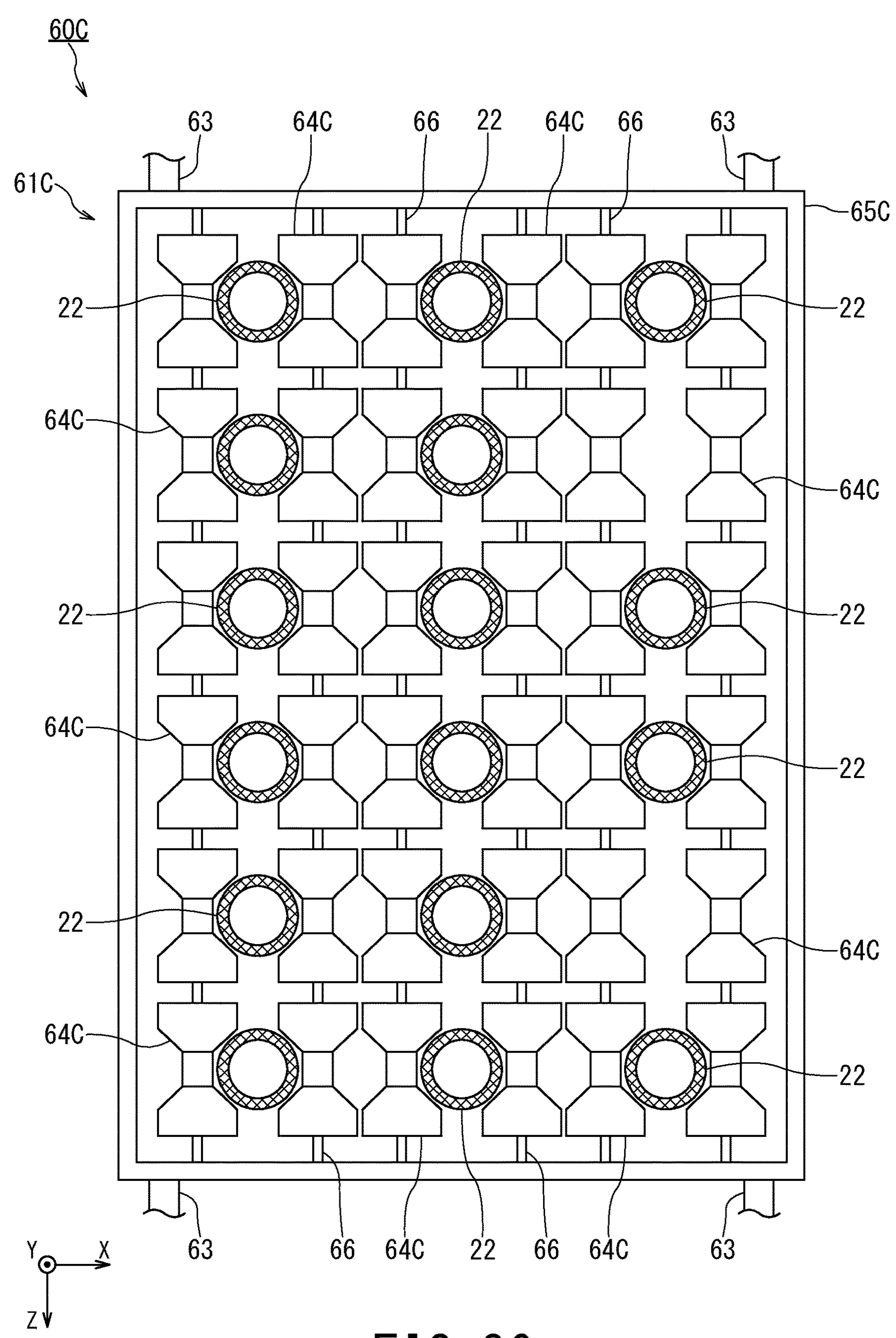
FIG. 26 is a plan view illustrating the cable straightening unit according to the seventh embodiment.

As shown in FIG. 26, the cable straightening apparatus 60C according to the seventh embodiment includes a single-stage cable straightening unit 61C. The disposition of the cable straightening unit 61C with respect to the spool 23 is the same as that of the above-described fourth embodiment (as illustrated in FIG. 17).

The frame 65C of the cable straightening unit 61C is provided with a plurality of shaft portions 66 that extend in the axial direction (i.e., in the Z-axis direction) and are arranged in the radial direction (i.e., in the X-axis direction). These rotating bodies 64C are rotatably supported by these shaft portions 66.

Figure 27:
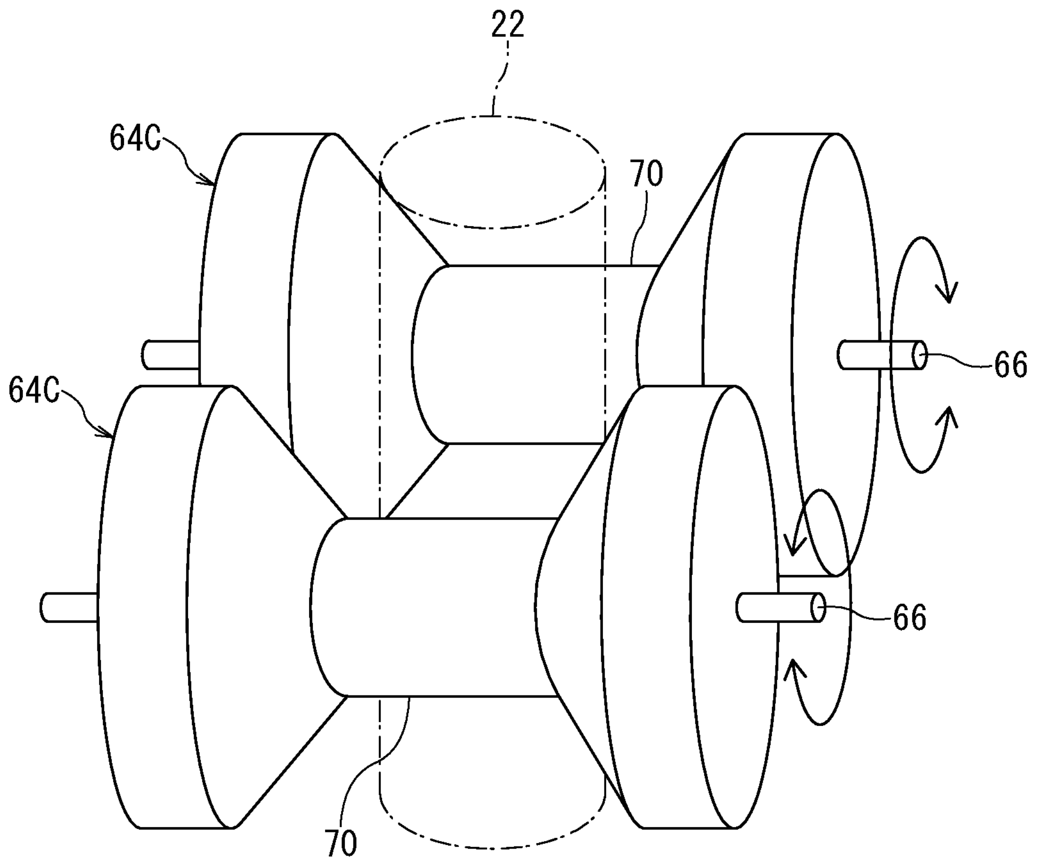
FIG. 27 is a perspective view illustrating rotating bodies according to the seventh embodiment.

As shown in FIG. 27, on the outer circumferential surface of each rotating body 64C, a recessed portion 70 is formed so as to be brought into contact with the cable 22. In other words, these rotating bodies 64C constitute saddle-shaped guide wheels for guiding the cables 22. For example, one rotating body 64C has a shape obtained by joining respective tips of two truncated cones to both ends of the central cylindrical portion. Further, one cable 22 can be held by at least two rotating bodies 64C so as to be sandwiched therebetween from the radial direction (i.e., in the X-axis direction).

Since the recessed portion 70 is formed on the outer circumferential surface of each rotating body 64C in the seventh embodiment, the cables 22 can be prevented from being shifted from the positions where the cables 22 are in contact with the rotating bodies 64C. For example, a portion of the outer circumference of the cable 22 is loosely fitted between the recessed portion 70 of the rotating body 64C, and thereby, the cable 22 is not shifted laterally (i.e., in the direction in which the shaft portions 66 extends).

In order to hold one cable 22, it is sufficient that only two rotating bodies 64C are disposed so as to sandwich the cable 22 therebetween in the radial direction (i.e., in the X-axis direction). Hence, the number of the rotating bodies 64C installed for one cable straightening unit 61C can be reduced.

Eighth Embodiment

Next, the eighth embodiment will be described by using FIG. 28 and FIG. 29. The same components as those shown in the above-described embodiments are denoted by the same reference signs, and duplicate descriptions are omitted.

Figure 28:
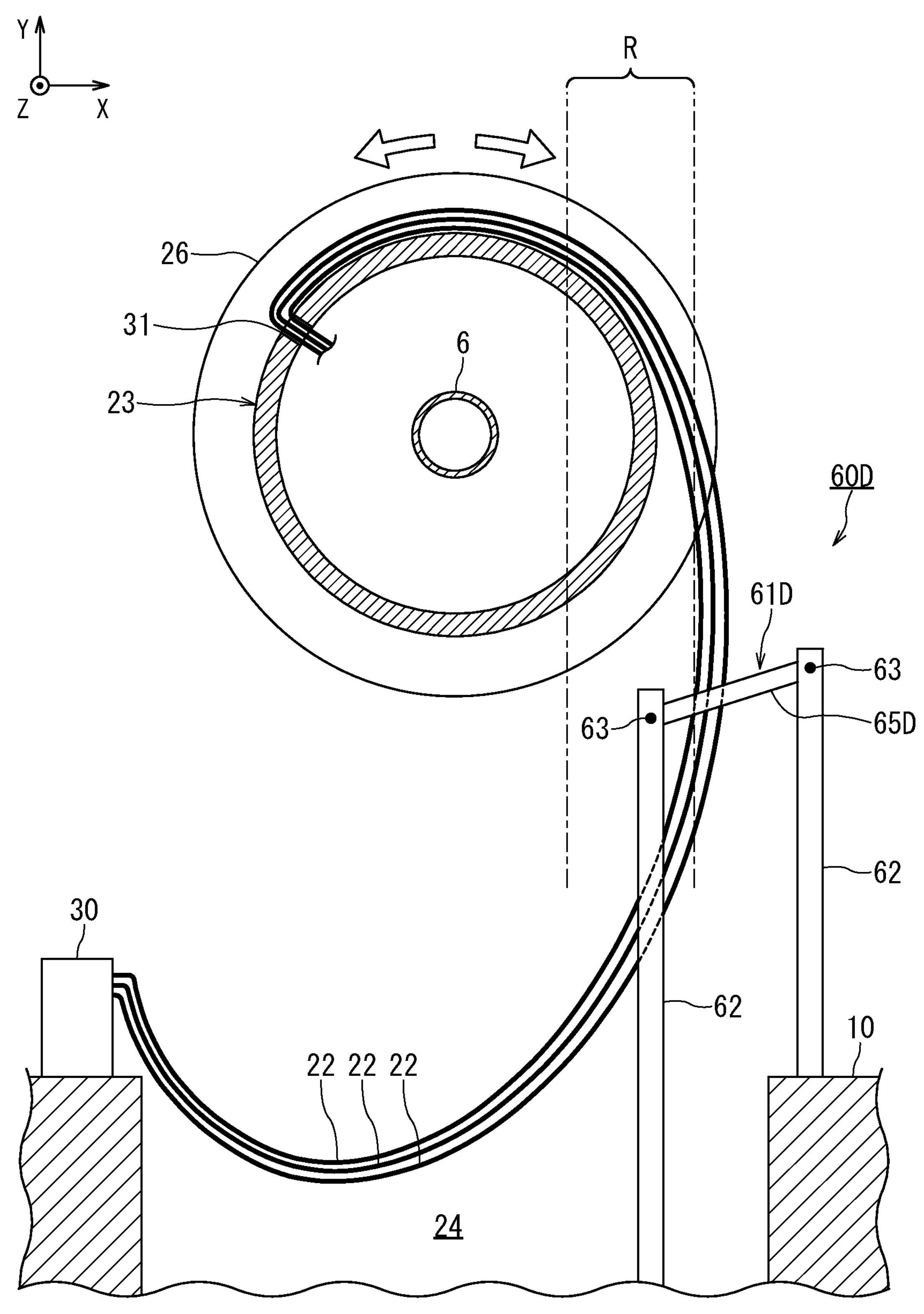
FIG. 28 is a rear view of the rotating gantry according to the eighth embodiment.

As shown in FIG. 28, the cable straightening apparatus 60D according to the eighth embodiment includes a single-stage cable straightening unit 61D. This cable straightening unit 61D is fixed to the unit mounts 62.

In the eighth embodiment, the cable straightening unit 61D is disposed so as to be horizontally displaced from the specific range R where the cables 22 hang down from the spool 23. For example, the cable straightening unit 61D is disposed so as to be displaced in the direction away from the spool 23 in the radial direction (i.e., in the X-axis direction). In other words, the cable straightening unit 61D is disposed so as to be displaced in the direction away from the fixing device 30.

Figure 29:
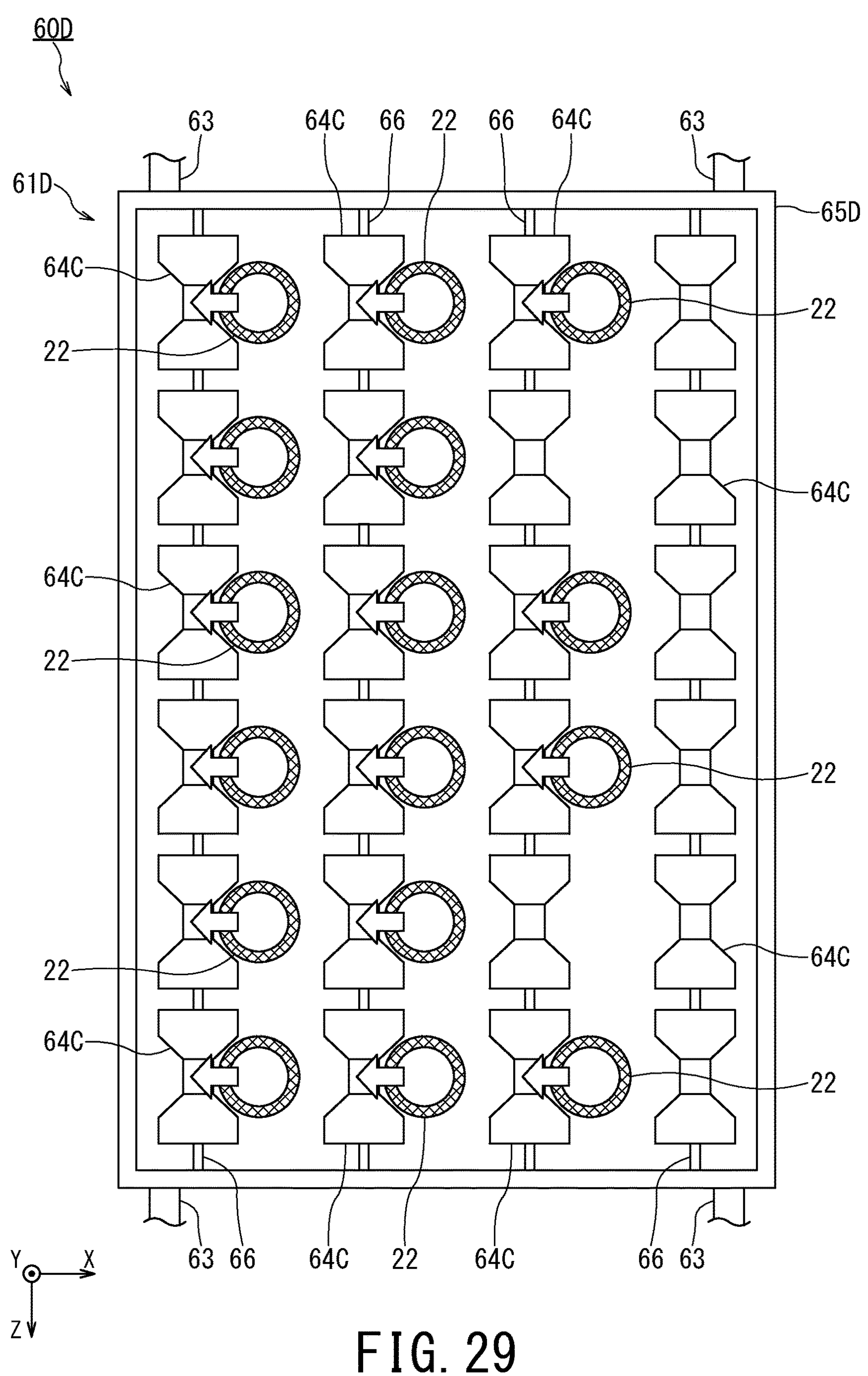
FIG. 29 is a plan view illustrating the cable straightening unit according to the eighth embodiment.

As shown in FIG. 29, the frame 65D of the cable straightening unit 61D is provided with a plurality of shaft portions 66 that extend in the axial direction (i.e., in the Z-axis direction) and are arranged in the radial direction (i.e., in the X-axis direction). These rotating bodies 64C are rotatably supported by these shaft portions 66. On the outer circumferential surface of each rotating body 64C, the recessed portion 70 (FIG. 27) is formed so as to be brought into contact with the cable 22 in a manner similar to the seventh embodiment. These rotating bodies 64C are saddle-shaped guide wheels.

As shown in FIG. 28 and FIG. 29, because the frame 65D of the cable straightening unit 61D is disposed so as to be horizontally displaced from the specific range R, the cables 22 are wound onto the spool 23 from diagonally below. In addition, the cables 22 are unwound diagonally downward from the spool 23. Each rotating body 64C is constantly brought into contact with the cable 22 from one direction.

If the frame 65D is displaced away from the spool 23, a load is applied to the cables 22 in the direction toward the spool 23 due to their own weight. For example, the force to move the cables 22 toward the left side of the sheet of FIG. 29 acts on the cables 22. Thus, each cable 22 is constantly brought into contact with the same portion of the outer circumferential surface of each rotating body 64C.

In the eighth embodiment, the cables 22 hanging down from the spool 23 pass vertically between the rotating bodies 64C arranged in the direction of intersecting the extending direction of the cables 22, and the cables 22 are brought into contact with the rotating bodies 64C from one direction in both cases of being wound and being unwound. In this configuration, each cable 22 is brought into contact with one side of the rotating body 64C in both cases of being wound and being unwound, and thus, the installation number of the rotating bodies 64C can be reduced. In other words, in order to guide one cable 22, it is sufficient that only one rotating body 64C is provided. Hence, the configuration of the cable straightening unit 61D can be simplified and made compact.

In addition, the cables 22 extend from the spool 23 to the fixing device 30 via the cable straightening unit 61D. When the cable straightening unit 61D is displaced in the direction away from the fixing device 30, the cables 22 are made to detour and extend from the spool 23 to the fixing device 30. Thus, the cables 22 disposed in the cable pit 24 are moved to upper positions, i.e., are lifted, and as a result, the depth dimension of the cable pit 24 can be set to be shallow.

The displacement amount (distance) when the cable straightening unit 61D is displaced from the specific range R in the horizontal direction is appropriately set depending on the configuration of the cables 22, i.e., depending on the type, thickness, and hardness (rigidity) of the cables 22. For example, for the cable straightening unit 61D, the displacement amount (distance) is set on the basis of the curvature of the cables 22 when the cables 22 bend while hanging down from the spool 23 in such a manner that the cables 22 do not ride on the cable straightening unit 61D by being buckled. In addition, a plurality of different cable straightening units 61D may be used to straighten the cables 22 depending on the type of cables 22. In that case, the displacement amount (distance) of each cable straightening unit 61D may be adjusted to an appropriate value depending on the type of cables 22.

Ninth Embodiment

Next, the ninth embodiment will be described by using FIG. 30 to FIG. 33. The same components as those shown in the above-described embodiments are denoted by the same reference signs, and duplicate descriptions are omitted.

The particle beam treatment system 1 according to the ninth embodiment is provided with a coolant supply apparatus 80 for the rotating gantry 5. This coolant supply apparatus 80 includes at least the cables 22. The cables 22 of the coolant supply apparatus 80 are provided in order to supply the coolant via the spool 23 to the superconducting electromagnets 15 of the transport unit 14 provided in the rotating gantry 5.

Figure 33:
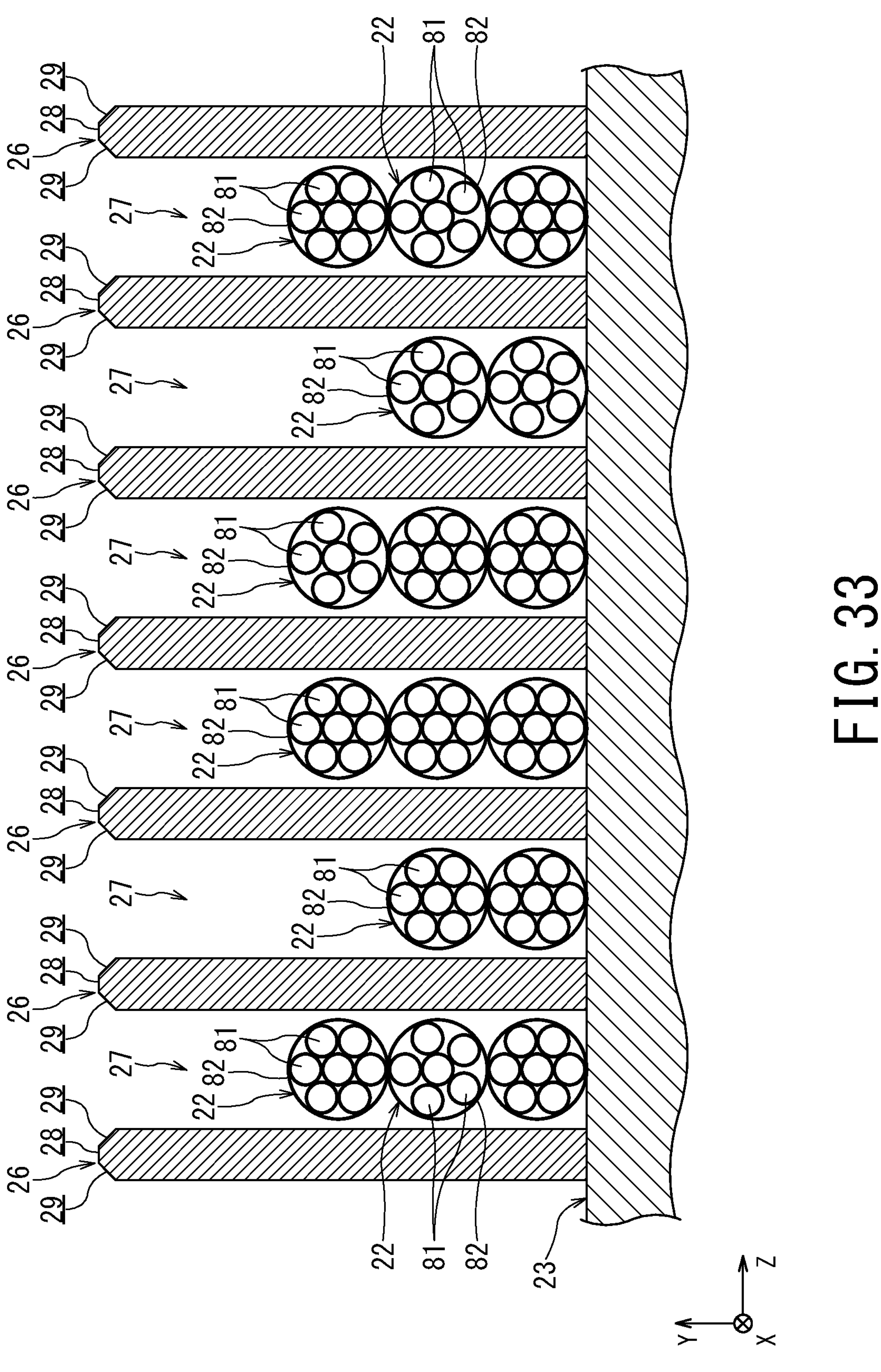
FIG. 33 is a side view illustrating the brim disks and the cables according to the ninth embodiment.

As shown in the cross-sectional view of FIG. 33, each cable 22 is formed by bundling a plurality of flexible hoses 81 so as to form a circular shape in a cross-sectional view. For example, five or six flexible hoses 81 are bundled, and a protective tape 82 is spirally wrapped around the outer circumference of this bundle in such a manner that these flexible hoses 81 and the protective tape 82 covering the surface form one cable 22. In addition, a plurality of flexible hoses 81 may be bundled and accommodated in one large-diameter tube (not shown) so as to form one cable 22.

The flexible hoses 81 are hollow inside (FIG. 33) and are provided in order to supply the coolant such as liquid helium and liquid nitrogen to the superconducting electromagnets 15 (FIG. 2). Each flexible hose 81 is configured as a pressure-resistant hose in which metal wires are woven to increase its pressure resistance, and can supply the coolant at a predetermined pressure.

In addition, the plurality of flexible hoses 81 to be bundled together as one cable 22 are the same as each other in type, thickness, and hardness (rigidity). In this configuration, the flexible hoses 81 bundled as one cable 22 can be bent to the same degree, which makes it easier to wind this cable 22 onto the spool 23. Note that the plurality of flexible hoses 81 to be bundled together as one cable 22 may be different from each other in terms of type, thicknesses, and rigidity.

Figure 30:
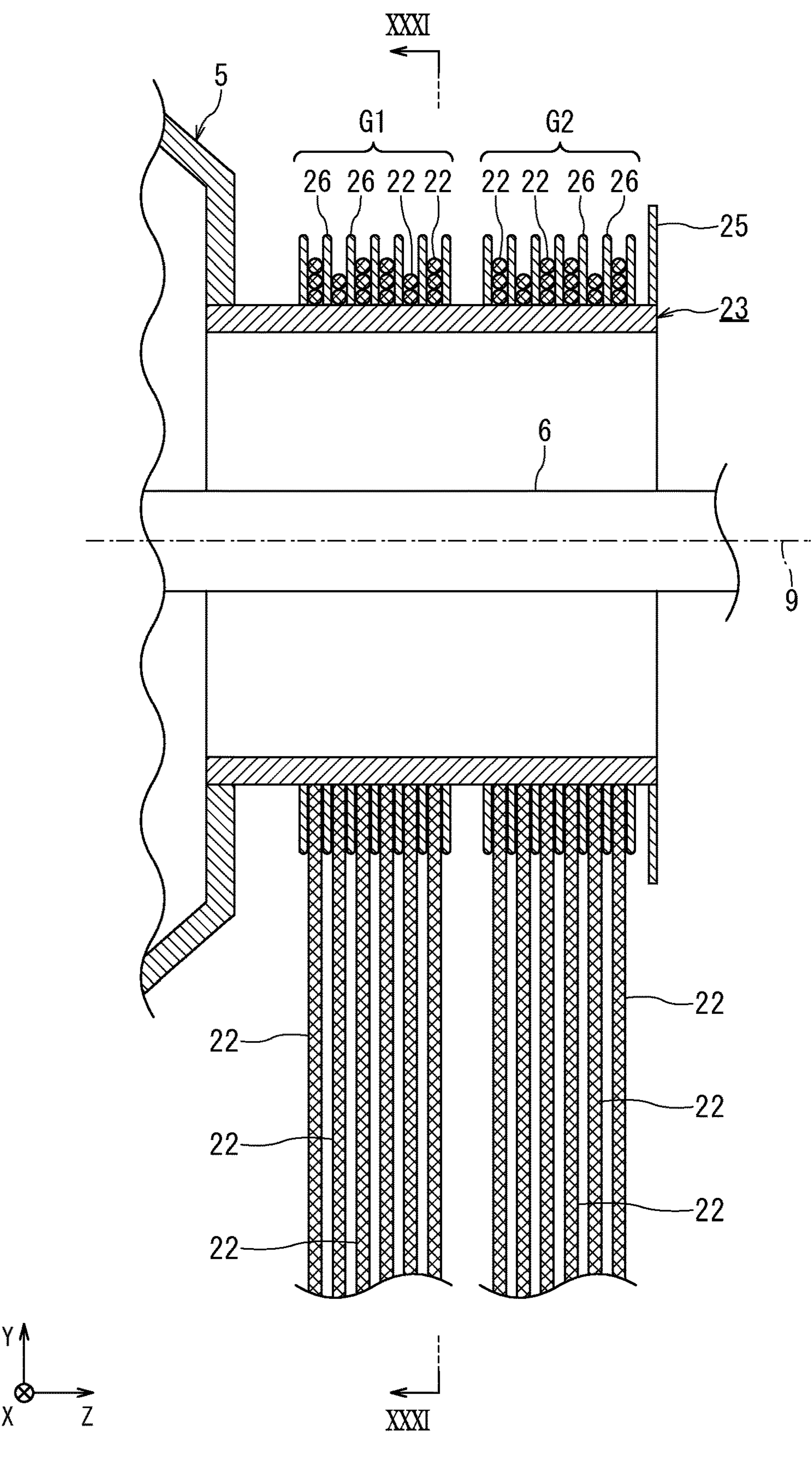
FIG. 30 is a side view illustrating the spool of the rotating gantry according to the ninth embodiment.
Figure 31:
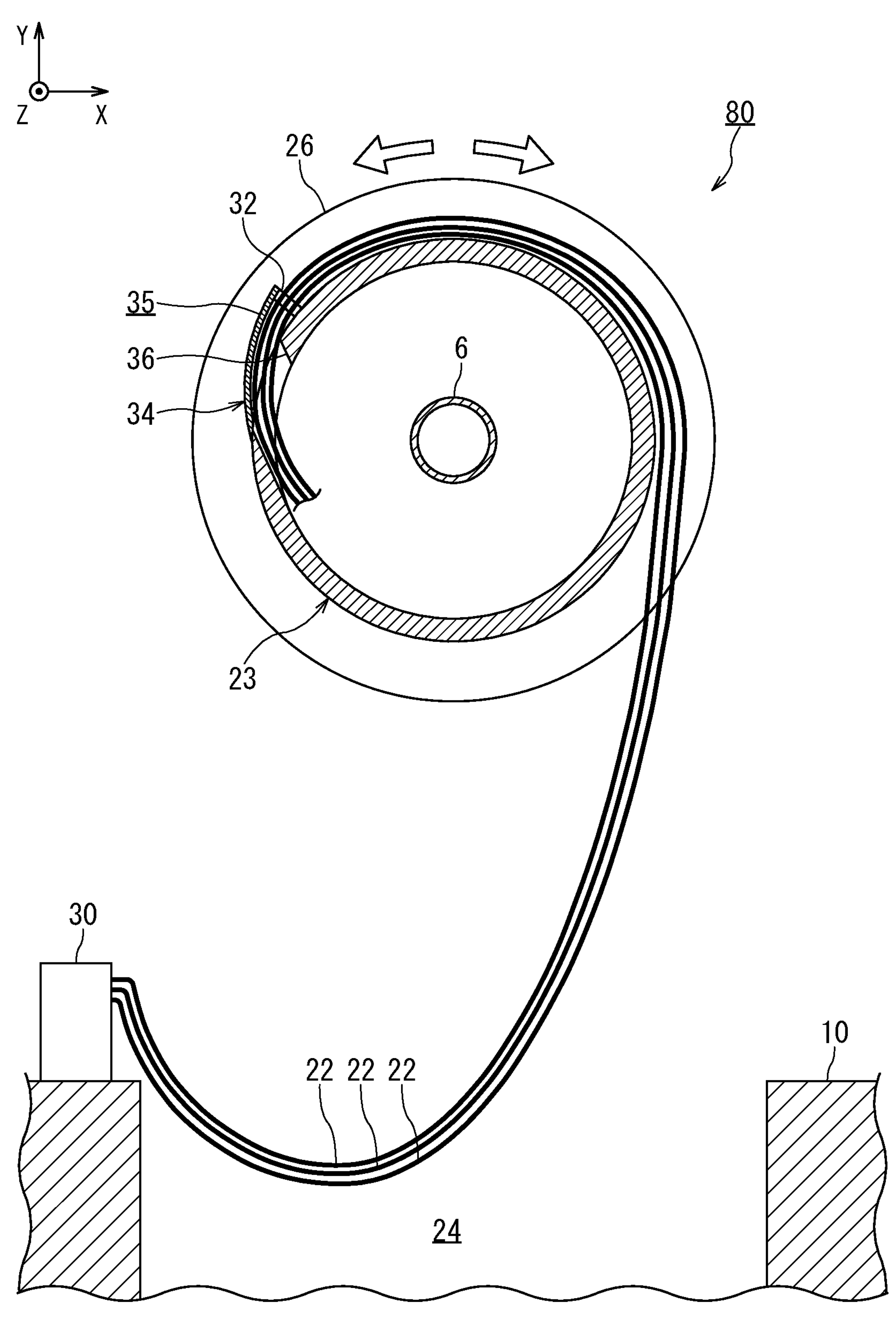
FIG. 31 is a rear view of the rotating gantry corresponding to the cross-section taken along the line XXXI-XXXI of FIG. 30.

As shown in FIG. 30 and FIG. 31, the plurality of cables 22 are divided or classified into the first group G1 and the second group G2. This division or classification into the first group G1 and the second group G2 may be performed by type of the cables 22 or by the device to which the cables 22 are connected. In accordance with this division, a plurality of brim disks 26 around which the plurality of cables 22 of the first group G1 are wound are provided, and a plurality of brim disks 26 around which the plurality of cables 22 of the second group G2 are wound are provided.

The cables 22 of the first group G1 are different from the cables 22 of the second group G2 in the direction of being wound around spool 23. For example, when the rotating gantry 5 rotates counterclockwise in a rear view, the cables 22 of the first group G1 are wound onto the spool 23, whereas the cables 22 of the second group G2 are unwound from the spool 23. Conversely, when the rotating gantry 5 rotates clockwise, the cables 22 of the first group G1 are unwound from the spool 23, whereas the cables 22 of the second group G2 are wound onto the spool 23.

In FIG. 31, for the sake of facilitating understanding, only the cables 22 of the first group G1 are illustrated and the cables 22 of the second group G2 are omitted. In the actual rear view, the cables 22 of the first group G1 and the cables 22 of the second group G2 hanging down from the spool 23 appear to intersect each other at the cable pit 24.

Figure 32:
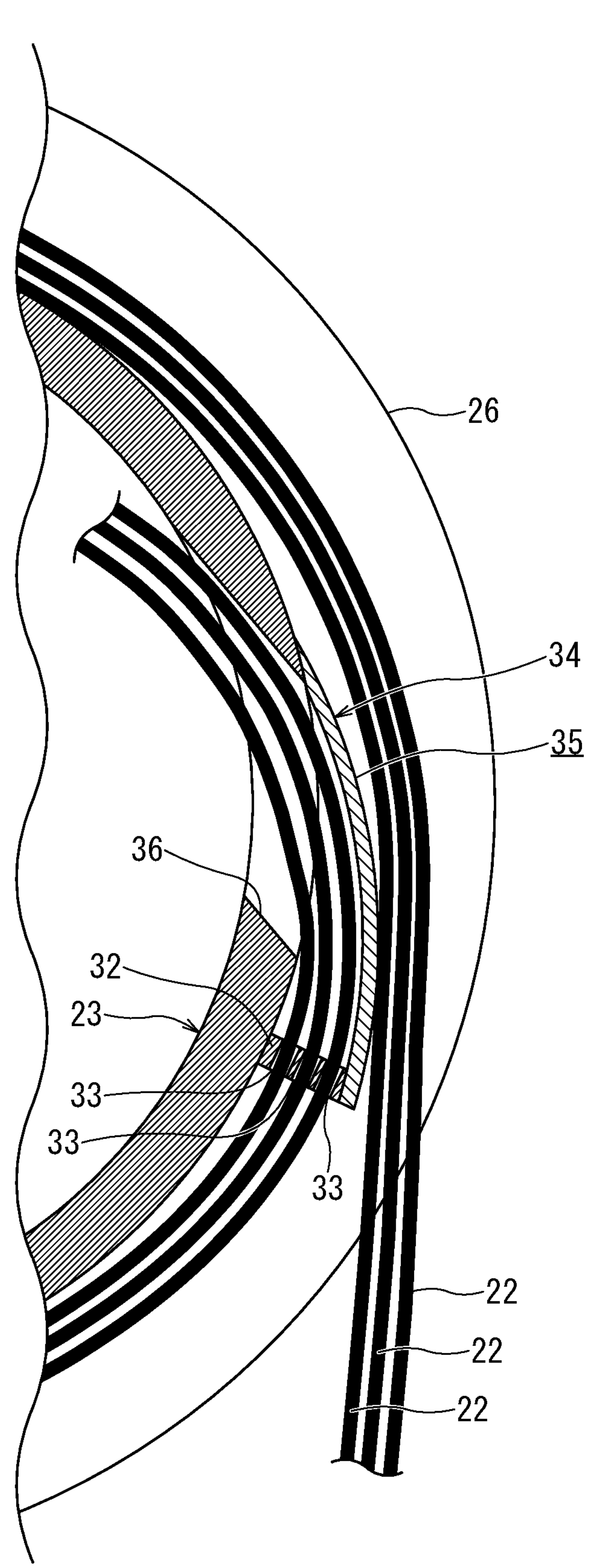
FIG. 32 is a rear view illustrating a cover of the spool according to the ninth embodiment.

As shown in FIG. 31 and FIG. 32, the coolant supply apparatus 80 further includes connector portions 32, penetration portions 33, and a cover 34. Note that the configuration of the coolant supply apparatus 80 may include all or any one of the rotating gantry 5, the spool 23, and the brim disks 26.

The connector portions 32 are provided so as to correspond to the lanes 27 (FIG. 33) that hold the cables 22 in the spool 23, and protrude in the radial direction of the spool 23. For example, one connector portion 32 is provided so as to correspond to the plurality of lanes 27 of the first group G1. The connector portions 32 are, for example, plate members or blocks that are provided so as to protrude in the radial direction from the outer circumferential surface of the spool 23.

The penetration portions 33 are through holes formed in each of the connector portions 32, and are portions that penetrate the connector portions 32 in the circumferential direction and pass the cables 22 from the outside to the inside of the spool 23. Of the spool 23, the portion corresponding to the penetration portions 33 is provided with a penetration window 36. The cables 22 are introduced into the rotating gantry 5 through the penetration portions 33 and the penetration window 36. Further, the cables 22 are connected to devices such as the superconducting electromagnets 15 (FIG. 2) provided in the rotating gantry 5. Note that cables 22 are fixed to the positions of the penetration portions 33. Each cable 22 is wound circumferentially from the fixed penetration portions 33 along the outer circumference of the spool 23 (lanes 27).

The cover 34 extends from the lanes 27 to the tips of the connector portions 32. This cover 34 is a member having an inclined surface 35 that is inclined with respect to the outer circumferential surface of the spool 23. The portion around the penetration window 36 of the spool 23 is covered with this cover 34. In this configuration, the cables 22 can be wound gently from the lanes 27 to the tips of connector portions 32, and thus, buckling of the cables 22 can be prevented. The above-described "buckling of the cables 22" means that the cables 22 are bent significantly to the extent that the inside of the cables 22 is crushed or the function of the cables 22 is impaired.

In the ninth embodiment, the cables 22 are not bent significantly at the portion around the penetration portions 33, which can prevent reduction in ability to supply the coolant to the superconducting electromagnets 15.

Since the cables 22 are fixed by using the connector portions 32, even if one cable 22 is partially twisted inside the spool 23, this twisting is not transmitted to the other portion of this cable 22 outside the spool 23. Thus, twisting of the cables 22 to be wound onto the spool 23 can be prevented.

When the connector portions 32 are provided, at the time of replacing the cables 22, this replacement maintenance can be performed separately for the inside of the spool 23 (i.e., inside of the connector portions 32) and for the outside of the spool 23 (i.e., outside of the connector portions 32). For example, a connection potion is provided at the region around the connector portions 32 in such a manner that one cable 22 can be attached and detached at this connection portion, and maintenance of this one cable 22 is performed separately for the inside of the spool 23 and for the outside of the spool 23. In this configuration, the burden of the maintenance work can be reduced.

Since the plurality of flexible hoses 81 are bundled into one cable 22 in the ninth embodiment, the respective flexible hoses 81 are prevented from being twisted due to irregular winding, which can achieve smooth supply of the coolant to the superconducting electromagnets 15 without interruption.

Although the plurality of flexible hoses 81 are bundled together to form one cable 22, another aspect may be adopted. For example, a plurality of power lines or a plurality of signal lines may be bundled together to form one cable 22. In addition, the flexible hoses 81, the power lines, and the signal lines may be bundled together to form one cable 22.

Tenth Embodiment

Figure 34:
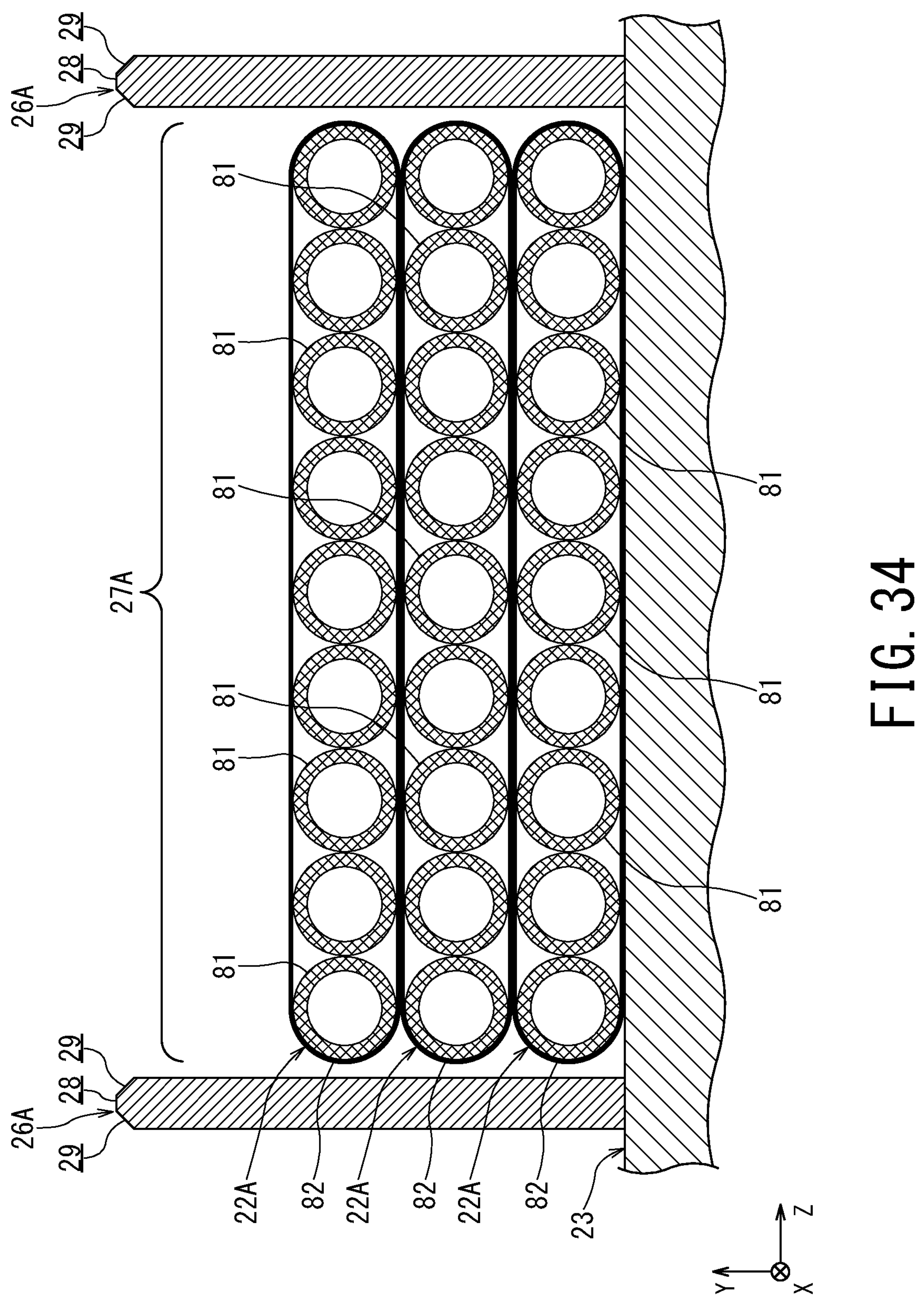
FIG. 34 is a side view illustrating the brim disks and the cables according to the tenth embodiment.

Next, the tenth embodiment will be described by using FIG. 34. The same components as those shown in the above-described embodiments are denoted by the same reference signs, and duplicate descriptions are omitted.

Each cable 22A of the tenth embodiment is in a band shape (i.e., a flat plate shape) formed by integrating a plurality of flexible hoses 81 in parallel with each other. In other words, one cable 22A is formed by flattening and integrating the plurality of flexible hoses 81 to form an oval shape in a cross-sectional view.

For example, nine flexible hoses 81 are aligned in a straight line in a cross-sectional view, and the outer peripheries of the aligned flexible hoses 81 are spirally wrapped with the protective tape 82 in such a manner that these flexible hoses 81 and this protective tape 82 covering the surface form one cable 22 as a whole. In addition, the plurality of flexible hoses 81 may be accommodated in one tube (not shown) in the state of being aligned so as to form one cable 22.

The spool 23 is provided with at least two brim disks 26A. Between these brim disks 26A, a concave lane 27A having an inlet dimension larger than the width dimension of each cable 22 is formed.

Note that the plurality of cables 22A are held for one lane 27A in the state of being stacked in the radial direction of the spool 23. In other words, the spool 23 can wind or unwind the plurality of cables 22A in the state where these cables 22A are stacked in the radial direction. In this configuration, the plurality of cables 22A can be orderly wound onto the spool 23 without causing irregular winding.

Since the cables 22A are band-shaped in the tenth embodiment, the cables 22A are unlikely to be irregularly wound, thereby, each flexible hose 81 is prevented from being twisted, which achieves smooth supply of the coolant to the superconducting electromagnets 15 (FIG. 2) without interruption. In addition, the installation number of the brim disks 26A can be reduced by flattening and integrating the cables 22A.

Eleventh Embodiment

Figure 35:
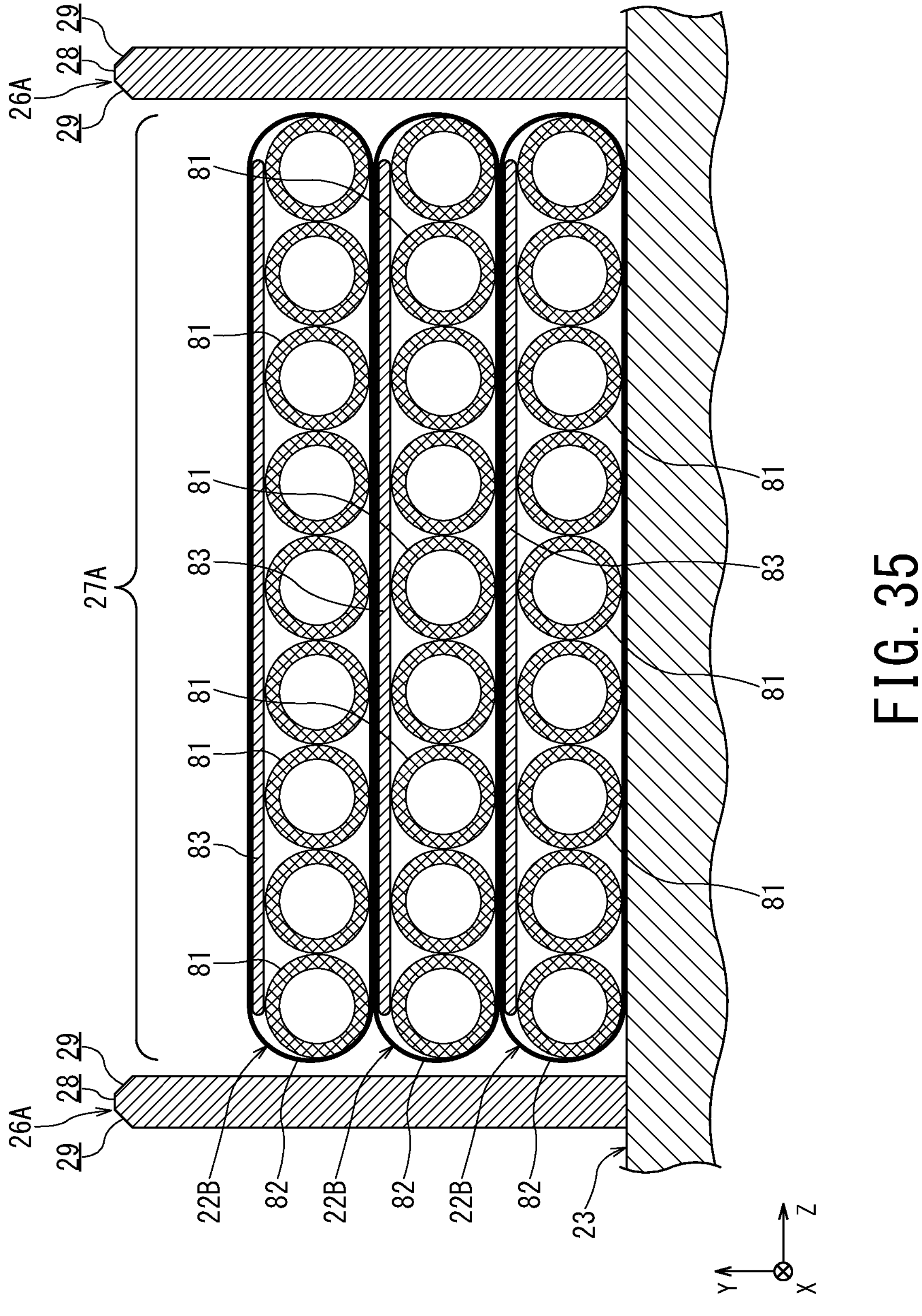
FIG. 35 is a side view illustrating the brim disks and the cables according to the eleventh embodiment.

Next, the eleventh embodiment will be described by using FIG. 35. The same components as those shown in the above-described embodiments are denoted by the same reference signs, and duplicate descriptions are omitted.

Each cable 22B of the eleventh embodiment is in a band shape (i.e., a flat plate shape) formed by integrating the plurality of flexible hoses 81 in parallel with each other. Furthermore, each cable 22B includes a band-shaped reinforcement member 83.

For example, nine flexible hoses 81 are aligned along one reinforcement member 83, and the outer peripheries of the aligned flexible hoses 81 and the reinforcement member 83 are spirally wrapped with the protective tape 82. In other words, the plurality of flexible hoses 81 are integrated together with the reinforcement member 83 by using the protective tape 82. Further, these flexible hoses 81, the reinforcement member 83, and the protective tape 82 form one cable 22B as a whole.

The reinforcement member 83 is provided at the portion that is the outer peripheral side of each band-shaped cable 22B when the cables 22B are wound around the spool 23. This configuration makes it easier to stack the cables 22B in the radial direction of the spool 23.

In the eleventh embodiment, the reinforcement member 83 makes each cable 22B insusceptible to twisting, and thus, twisting of the flexible hoses 81 can be suppressed. Further, in manufacture of the cables 22B, it becomes easier to arrange the flexible hoses 81 in a straight line in a cross-sectional view, which facilitates manufacture of the cables 22B.

Twelfth Embodiment

Figure 36:
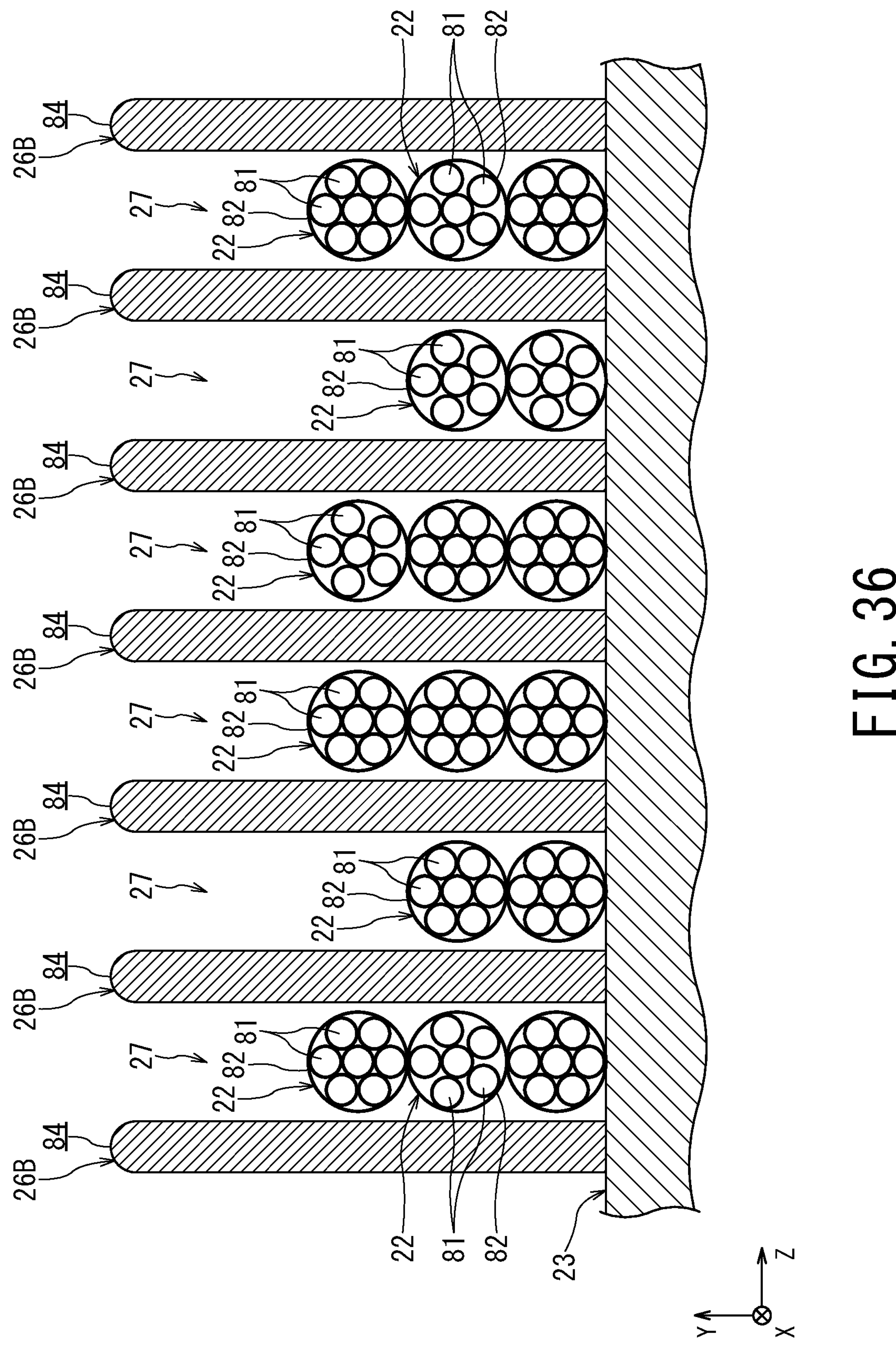
FIG. 36 is a side view illustrating the brim disks and the cables according to the twelfth embodiment.

Next, the twelfth embodiment will be described by using FIG. 36. The same components as those shown in the above-described embodiments are denoted by the same reference signs, and duplicate descriptions are omitted.

Each brim disk 26B of the twelfth embodiment has a semicircular periphery in a cross-sectional view. In other words, the circumferential surface of each brim disk 26B forms a curved surface 84. This curved surface 84 constitutes a chamfered portion of the twelfth embodiment. In addition, on the circumferential surface of each of the brim disk 26B, both corners may be curved to form so-called round chamfering portions.

Since the circumferential surface of each brim disk 26B is the curved surface 84 in the twelfth embodiment, each cable 22 is less likely to be caught in the brim disk 26B when being accommodated in the lane 27, thereby, the friction or tension on the cables 22 being caught on the brim disks 26 can be reduced, and consequently, the cables 22 are prevented from being irregularly wound. Even if the cable 22 is caught on the brim disk 26, the above-described configuration prevents the cable 22 from being cut or being worn out.

Thirteenth Embodiment

Figure 37:
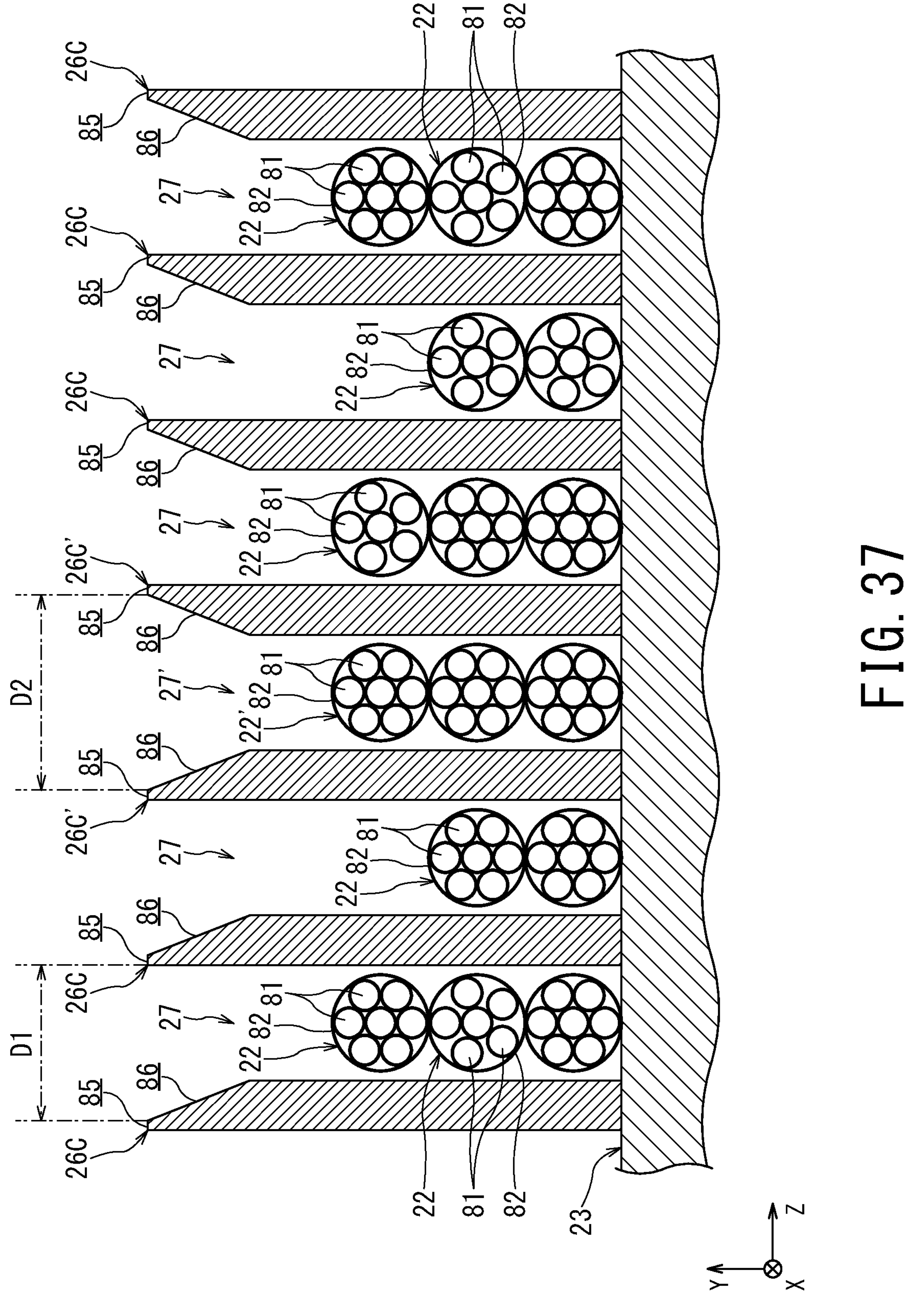
FIG. 37 is a side view illustrating the brim disks and the cables according to the thirteenth embodiment.

Next, the thirteenth embodiment will be described by using FIG. 37. The same components as those shown in the above-described embodiments are denoted by the same reference signs, and duplicate descriptions are omitted.

On the peripheral surface 85 of each brim disk 26C in the thirteenth embodiment, a chamfered portion 86 is formed by cutting out one corner. In other words, the chamfered portion 86 is formed on only one side of each brim disk 26C. For example, the chamfered portion 86 is an inclined surface having an inclination of about 30° with respect to the protruding direction of the brim disk 26C.

Of the two brim disks 26C arranged on both sides of one lane 27, one brim disks 26C is disposed so as to direct its surface formed as the chamfered portion 86 to the lane 27, and the other brim disks 26C is disposed so as to direct the surface without being formed as the chamfered portion 86 to the lane 27. In this configuration, the inlet dimension D1 of each lane 27 can be made wider than at least the case where the chamfered portion 86 is not formed.

For a specific lane 27', both brim disks 26C' on both sides of this lane 27' are arranged in such a manner that both surfaces formed as the chamfered portions 86 face this lane 27'. In this configuration, the inlet dimension D2 can be at least wider than the inlet dimension D1 of the other lanes 27. For example, when the lane 27' that is more difficult for the cable 22' to enter than the other lanes 27 can be specified in advance, the chamfered portions 86 are arranged on both sides of this lane 27' so as to create a wide inlet dimension D2. This configuration makes the cable 22' easier to enter the lane 27', and thus, the cables 22 are prevented from being irregularly wound.

Fourteenth Embodiment

Figure 38:
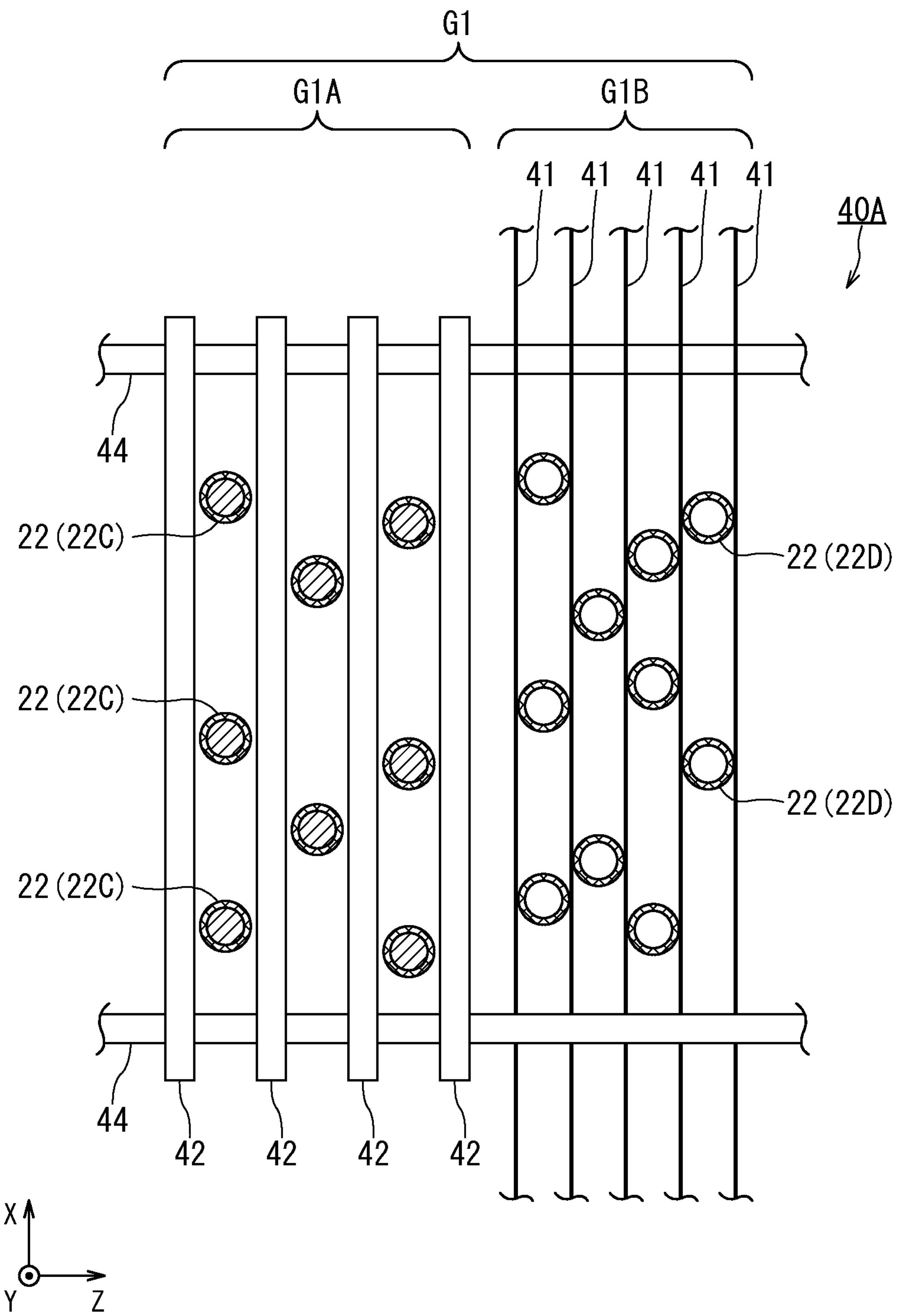
FIG. 38 is a plan view illustrating the cable straightening apparatus for the rotating gantry according to the fourteenth embodiment.

Next, the fourteenth embodiment will be described by using FIG. 38. The same components as those shown in the above-described embodiments are denoted by the same reference signs, and duplicate descriptions are omitted.

In the cable straightening apparatus 40A according to the fourteenth embodiment, in the axial direction (i.e., in the Z-axis direction), the range where the straightening wires 41 are arranged is different from the range where the straightening plates 42 are arranged. For example, the plurality of straightening plates 42 are arranged in a predetermined range along the axial direction, and the straightening wires 41 are arranged in another range different from the arrangement range of the straightening plates 42. Further, some of the cables 22 arranged in the axial direction are partitioned by the straightening plates 42, and the other cables 22 are partitioned by the straightening wires 41.

For example, it is assumed that the first group G1 composed of the plurality of cables 22 is divided into a group-A G1A consisting of a plurality of power lines 22C and a group-B G1B consisting of a plurality of flexible hoses 22D. Further, it is also assumed that the group-A G1A and the group-B G1B are arranged in the axial direction. The plurality of power lines 22C of the group-A G1A are partitioned by the straightening plates 42, whereas the plurality of flexible hoses 22D of the group-B G1B are partitioned by the straightening wires 41.

In the fourteenth embodiment, each cable 22 can be partitioned by using the members suitable for each type of cable 22. For example, the cables 22 suitable for being partitioned by flexible members are partitioned by the straightening wires 41. Conversely, the cables 22 suitable for being partitioned by rigid members are partitioned by the straightening plates 42.

Although the power lines 22C are partitioned by the straightening plates 42 and the flexible hoses 22D are partitioned by the straightening wires 41 in the fourteenth embodiment, another aspect may be adopted. For example, it may be configured in such a manner that the flexible hoses 22D are partitioned by the straightening plates 42 and the power lines 22C are partitioned by the straightening wires 41.

Fifteenth Embodiment

Figure 39:
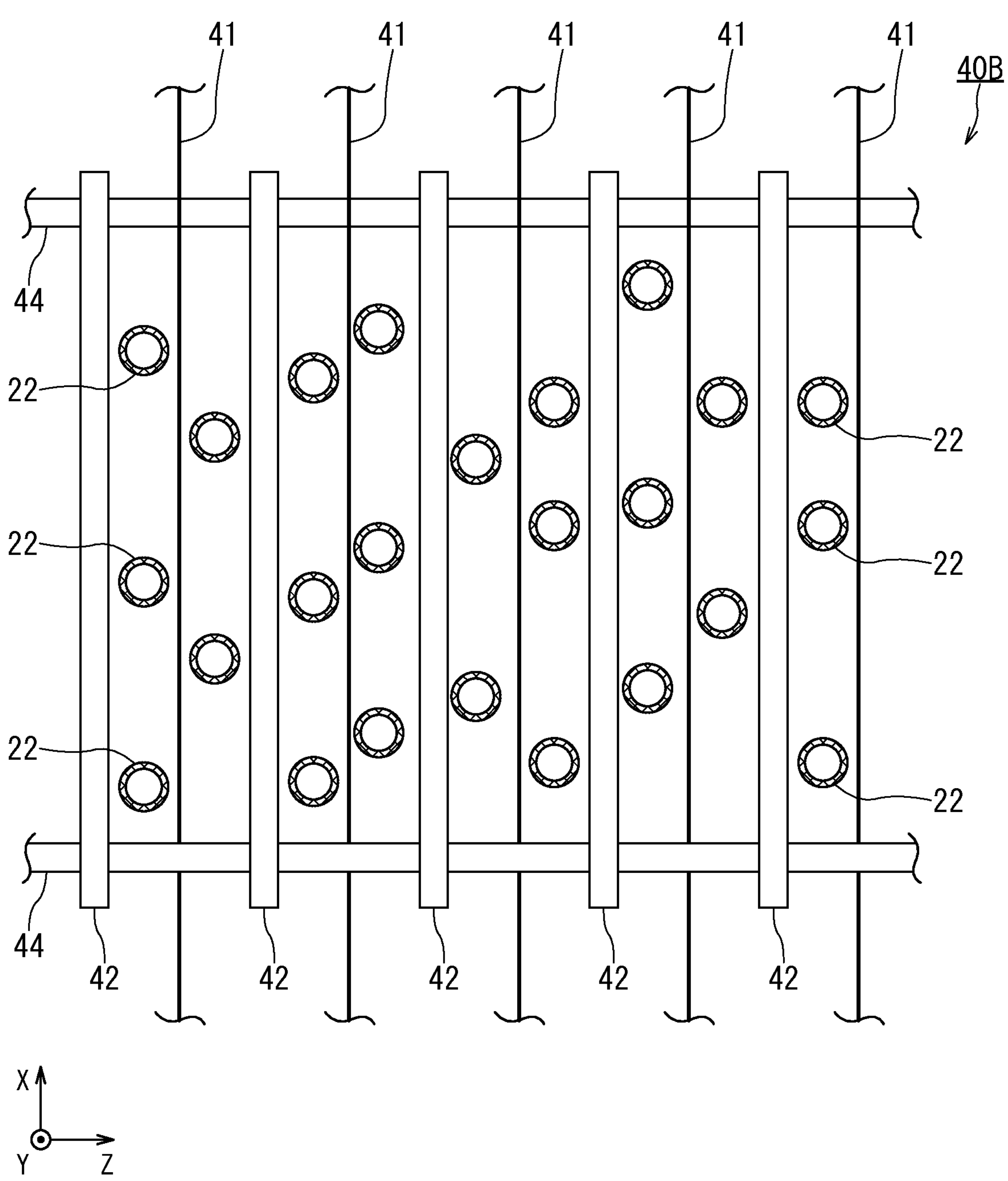
FIG. 39 is a plan view illustrating the cable straightening apparatus for the rotating gantry according to the fifteenth embodiment.

Next, the fifteenth embodiment will be described by using FIG. 39. The same components as those shown in the above-described embodiments are denoted by the same reference signs, and duplicate descriptions are omitted.

In the description of the fifteenth embodiment, a plurality of cables 22 arranged in the X-axis direction are referred to as one row of the cables 22. In the cable straightening apparatus 40B according to the fifteenth embodiment, the range where the straightening wires 41 are provided partially or entirely overlaps the range where the straightening plates 42 are provided. For example, one straightening wire 41 is strung between two straightening plates 42.

Further, one row of the cables 22 is provided on each of both sides of one straightening wire 41, and two rows of the cables 22 are provided between two straightening plates 42. In other words, the width between the respective straightening plates 42 is set in such a manner that two rows of the cables 22 can be disposed with one straightening wire 41 sandwiched therebetween. The total number of the installed straightening wires 41 and the installed straightening plates 42 is equal to the number of the brim disks 26.

In the fifteenth embodiment, the plurality of cables 22 arranged in the axial direction (i.e., in the Z-axis direction) are partitioned by either or both of the straightening wires 41 and the straightening plates 42. Each cable 22 is held in the state of being sandwiched between the straightening wire 41 and straightening plate 42.

Since the plurality of cables 22 are partitioned by the straightening plates 42 configured as rigid members in the fifteenth embodiment, swinging of the cables 22 can be suppressed. Further, on the outer circumferential surface of each cable 22, the side opposite to the surface in contact with the straightening plate 42 is in contact with the straightening wire 41 configured as a flexible member, and thus, wear of the cables 22 can be suppressed. In addition, the straightening wires 41 can absorb the vibration of the cables 22.

In the fifteenth embodiment, when the straightening wires 41 and the straightening plates 42 are installed over a predetermined range, the installation number of the straightening wires 41 and the straightening plates 42 can be reduced. For example, it is sufficient that the installation number of the straightening wires 41 is approximately half the installation number of the brim disks 26. Furthermore, it is sufficient that the installation number of the straightening plates 42 is approximately half the installation number of the brim disks 26.

Sixteenth Embodiment

Figure 40:
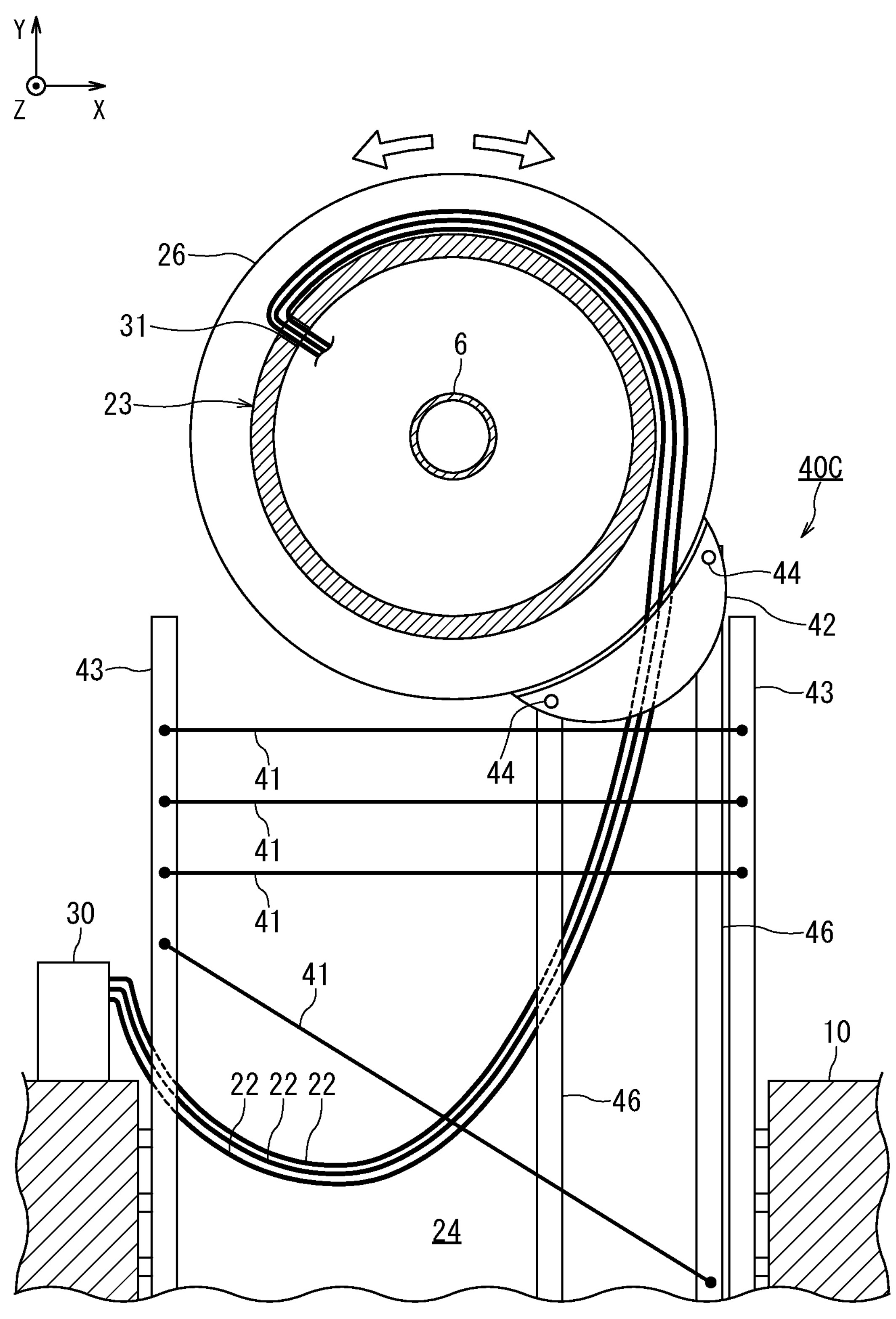
FIG. 40 is a plan view illustrating the cable straightening apparatus for the rotating gantry according to the sixteenth embodiment.

Next, the sixteenth embodiment will be described by using FIG. 40. The same components as those shown in the above-described embodiments are denoted by the same reference signs, and duplicate descriptions are omitted.

In the cable straightening apparatus 40C according to the sixteenth embodiment, the plurality of straightening wires 41 are strung at different height positions. For example, four straightening wires 41 with different height positions (i.e., with different Y-axis positions) are strung at the same position in the axial direction (i.e., at the same Z-axis position). These four straightening wires 41 are arranged side by side in the axial direction so as to partition the cables 22 arranged in the axial direction.

In addition, the cables 22 hanging down from the spool 23 are held at the respective positions of the four straightening wires 41 at different heights. Thus, swinging of the cables 22 can be suppressed. Furthermore, application of the force in the direction of twisting the cables 22 can be suppressed, which makes the cables 22 more insusceptible to irregular winding ascribable to swinging or twisting.

Of the four straightening wires 41, the three straightening wires 41 on the upper side are strung horizontally, whereas the remaining one bottommost straightening wire 41 is strung in an inclined state with respect to the horizontal direction. For example, under the assumption that the spool 23 is divided into a semicircle on the side where cables 22 hang down and the opposite semicircle, the bottommost straightening wire 41 is inclined in such a manner that the side where the cables 22 hang down is lower and the opposite side is higher. The three straightening wires 41 on the upper side and the one bottommost straightening wire 41 are both strung almost perpendicularly to the direction in which the straightening wires 41 extend.

In the sixteenth embodiment, the plurality of straightening plates 42 are provided at positions close to the brim disks 26, and the plurality of straightening wires 41 are strung at positions lower than the positions where these straightening plates 42 are provided. For example, the topmost straightening wire 41 is provided at a position close to the straightening plates 42 and extends in the tangential direction of the periphery of the lower end of the straightening plates 42. In this configuration, the straightening wires 41 can guide the cables 22 at the portion where the cables 22 are no longer held by the straightening plates 42, thereby, swinging of the cables 22 can be suppressed, and consequently, the cables 22 are prevented from being irregularly wound.

In the particle beam treatment system 1, though the rotating gantry 5 can be downsized by using the superconducting electromagnets 15, hoses for flowing the liquid helium to be used for cooling down the superconducting electromagnets 15 are also required. As a result, the number of the cables 22 increases and the thickness and rigidity of each type of the cables 22 also differ, which increases the difficulty of straightening the cables 22. However, in the above-described embodiments, the straightening wires 41 or the straightening plates 42 can be provided in an appropriate manner for each type of the cables 22, which facilitates the work of straightening the cables 22.

As above, although the particle beam treatment system 1 and the rotating gantry 5 have been described on the basis of the first to sixteenth embodiments, the configuration applied in any one of the embodiments may be applied to other embodiments or the configurations in the respective embodiments may be applied in combination.

For example, when the band-shaped cables 22A and 22B of the tenth or the eleventh embodiment are held by the brim disks 26C of the thirteenth embodiment, the brim disks 26C are provided in such a manner that the chamfered portions 86 of both brim disks 26C sandwiching the cables 22A and 22B are directed toward these cables 22A and 22B and thereby the inlet width is widened.

Although a mode in which each step is executed in series is illustrated in the flowcharts of the above-described embodiments, the execution order of the respective steps is not necessarily fixed and the execution order of part of the steps may be changed. Additionally, some steps may be executed in parallel with another step.

The monitoring apparatus 50 (50A, 50B) in the above-described embodiments include a storage device such as a Read Only Memory (ROM) and a Random Access Memory (RAM), an external storage device such as a Hard Disk Drive (HDD) and a Solid State Drive (SSD), a display device such as a display panel, an input device such as a mouse and a keyboard, a communication interface, and a control device which has a highly integrated processor such as a Central Processing Unit (CPU), a Graphics Processing Unit (GPU), a Field Programmable Gate Array (FPGA), and a special-purpose chip. The monitoring apparatus 50 (50A, 50B) can be achieved by hardware configuration with the use of normal computer.

Note that the program executed in the monitoring apparatus 50 (50A, 50B) of the above-described embodiment are provided by being incorporated in a memory such as the ROM in advance. Additionally, or alternatively, the program may be provided by being stored as a file of installable or executable format in a non-transitory computer-readable storage medium such as a CD-ROM, a CD-R, a memory card, a DVD and a flexible disk (FD).

In addition, the program executed in the monitoring apparatus 50 (50A, 50B) maybe stored on a computer connected to a network such as the Internet and be provided by being downloaded via a network. Further, the monitoring apparatus 50 (50A, 50B) can also be configured by interconnecting and combining separate modules, which independently exhibit respective functions of the components, via a network or a dedicated line.

Although a facility configured to perform heavy-ion-beam cancer treatment is exemplified in the above-described embodiments, the above-described embodiments can also be applied to other facilities. For example, the above-described embodiments may be applied to a facility that performs proton-beam cancer treatment.

According to at least one embodiment described above, the winding state of the plurality of cables in the spool can be monitored by providing the monitoring unit that monitors the state of the cables.

Since the configuration of each of the above-described embodiments includes the cable straightening unit having the plurality of rotatable cylindrical rotating bodies that partition the plurality of cables and contact the cables at their outer circumferential surfaces, the cables are prevented from being irregularly wound, and wear of the cables can be suppressed.

In addition, buckling of the cables for suppling the coolant to the superconducting electromagnets can be prevented by providing the penetration portion that penetrates the spool in the circumferential direction of the spool and causes the cables to pass from the outside to the inside of the spool.

Moreover, smooth supply of the coolant to the superconducting electromagnets of the transport unit can be achieved without any interruption by forming each cable into the band-shaped cable in which the plurality of flexible hoses for supplying the coolant to the superconducting electromagnets are arranged in parallel with each other and integrated.

Furthermore, the plurality of cables can be prevented from being irregularly wound and being unnecessarily worn away by providing the plurality of straightening wires that are laid or bridged below the spool in a stationary state and partition the cables hanging down from the spool.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A monitoring apparatus for a rotating gantry comprising:

a rotating gantry that supports both an irradiation nozzle configured to radiate a particle beam and a transport unit configured to transport the particle beam to the irradiation nozzle and rotates around a horizontal axis directed in a horizontal direction;

a plurality of cables, each of which is connected at one end to the rotating gantry and is connected at another end to a stationary device;

a spool that is provided on the rotating gantry and performs winding or unwinding of the plurality of cables;

a monitoring unit that monitors a state of the plurality of cables in the spool;

a connector portion that is provided corresponding to at least one lane configured to hold at least one of the plurality of cables in the spool and is protruded in a radial direction of the spool; and a penetration portion that is formed in the connector portion, penetrates the connector portion in a circumferential direction of the spool, and passes at least one of the plurality of cables from outside to inside of the spool, wherein;

the transport unit includes a superconducting electromagnet configured to generate a magnetic field that forms a path for transporting the particle beam; and at least one of the cables is configured as a flexible hose that supplies a coolant to the superconducting electromagnet.

2. The monitoring apparatus for the rotating gantry according to claim 1, further comprising a cable straightening unit that is installed in a stationary state at a position close to the spool, partitions the plurality of cables, and includes a plurality of rotatable cylindrical rotating bodies, wherein each of the rotatable cylindrical rotating bodies is brought into contact with at least one of the plurality of cables at an outer circumferential surface.

3. The monitoring apparatus for the rotating gantry according to claim 1, further comprising an interlock controller configured to stop drive of the rotating gantry when an abnormality in at least one of the plurality of cables is detected based on monitoring by the monitoring unit.

4. The monitoring apparatus for the rotating gantry according to claim 1, wherein the monitoring unit is a camera configured to image the spool.

5. The monitoring apparatus for the rotating gantry according to claim 1, wherein:

the transport unit includes a superconducting electromagnet configured to generate a magnetic field that forms a path for transporting the particle beam.

6. A monitoring apparatus for a rotating gantry comprising:

a rotating gantry that supports both an irradiation nozzle configured to radiate a particle beam and a transport unit configured to transport the particle beam to the irradiation nozzle and rotates around a horizontal axis directed in a horizontal direction;

a plurality of cables, each of which is connected at one end to the rotating gantry and is connected at another end to a stationary device;

a spool that is provided on the rotating gantry and performs winding or unwinding of the plurality of cables;

a monitoring unit that monitors a state of the plurality of cables in the spool; and a plurality of straightening wires that are bridged laterally below the spool, are provided in a stationary state, and partition the plurality of cables hanging down from the spool.

7. A monitoring apparatus for a rotating gantry comprising:

a rotating gantry that supports both an irradiation nozzle configured to radiate a particle beam and a transport unit configured to transport the particle beam to the irradiation nozzle and rotates around a horizontal axis directed in a horizontal direction;

a plurality of cables, each of which is connected at one end to the rotating gantry and is connected at another end to a stationary device;

a spool that is provided on the rotating gantry and performs winding or unwinding of the plurality of cables; and a monitoring unit that monitors a state of the plurality of cables in the spool, wherein:

the spool includes a plurality of disc-shaped brim disks and a plurality of concave lanes that hold at least one of the plurality of cables between respective brim disks; and the monitoring unit is configured as a laser sensor that radiates a laser beam along a peripheral edge of the plurality of brim disks in an axial direction and detects at least one of the plurality of cables protruding from the plurality of brim disks.

8. The monitoring apparatus for the rotating gantry according to claim 7, wherein:

the spool is provided to protrude rearward from a rear portion of the rotating gantry; and the laser sensor is configured to radiate the laser beam rearward from a position close to the rear portion of the rotating gantry.

9. The monitoring apparatus for the rotating gantry according to claim 7, wherein the laser sensor is configured as a reflective laser sensor that detects at least one of the plurality of cables protruding from the plurality of brim disks based on reflection of the laser beam radiated to the at least one of the plurality of cables.

10. The monitoring apparatus for the rotating gantry according to claim 7, further comprising a plurality of straightening plates that partition the plurality of cables arranged in the axial direction and are arranged in parallel in a stationary state at a position close to the spool, wherein the laser sensor is provided at a position corresponding to the plurality of straightening plates in a circumferential direction of the spool.

11. A monitoring apparatus for a rotating gantry comprising:

a rotating gantry that supports both an irradiation nozzle configured to radiate a particle beam and a transport unit configured to transport the particle beam to the irradiation nozzle and rotates around a horizontal axis directed in a horizontal direction;

a plurality of cables, each of which is connected at one end to the rotating gantry and is connected at another end to a stationary device;

a spool that is provided on the rotating gantry and performs winding or unwinding of the plurality of cables; and a monitoring unit that monitors a state of the plurality of cables in the spool, wherein:

the spool includes a plurality of disc-shaped brim disks and a plurality of concave lanes that hold at least one of the plurality of cables between respective brim disks; and the monitoring unit is configured as a limit switch that detects a protruding state of at least one of the plurality of cables held by the plurality of concave lanes.

* * * * *